(12) United States Patent
Frey et al.

(10) Patent No.: US 8,637,585 B2
(45) Date of Patent: Jan. 28, 2014

(54) SILSESQUIOXANE PHOTOINITIATORS

(75) Inventors: Markus Frey, Rheinfelden (CH);
Christophe Frossard, Granges-Paccot (CH); Katia Studer, Rixheim (FR); Karin Powell, Lörrach (DE); Jean-Luc Birbaum, Binningen (CH); Martin Müller, Lörrach (DE)

(73) Assignee: BASF SE, Ludwigshafen (DE)

( * ) Notice: Subject to any disclaimer, the term of this patent is extended or adjusted under 35 U.S.C. 154(b) by 97 days.

(21) Appl. No.: 13/130,796

(22) PCT Filed: Nov. 24, 2009

(86) PCT No.: PCT/EP2009/065695
§ 371 (c)(1),
(2), (4) Date: Jun. 21, 2011

(87) PCT Pub. No.: WO2010/063612
PCT Pub. Date: Jun. 10, 2010

(65) Prior Publication Data
US 2012/0142793 A1 Jun. 7, 2012

(30) Foreign Application Priority Data
Dec. 1, 2008 (EP) .................................. 08170335

(51) Int. Cl.
*C08F 2/50* (2006.01)
*C08J 3/28* (2006.01)
*C08F 283/12* (2006.01)
*C08F 283/00* (2006.01)

(52) U.S. Cl.
USPC .................. 522/6; 522/35; 522/99; 522/172; 522/148; 522/7; 525/474; 525/479

(58) Field of Classification Search
USPC ..................... 522/6, 7, 35, 99, 148, 172, 904; 525/474, 479
See application file for complete search history.

(56) References Cited

U.S. PATENT DOCUMENTS

| 5,021,478 | A | 6/1991 | Ravichandran | |
|---|---|---|---|---|
| 2004/0089842 | A1 | 5/2004 | Sutherland | |
| 2004/0198859 | A1 | 10/2004 | Nguyen | |
| 2005/0250925 | A1* | 11/2005 | Oikawa et al. | 528/25 |
| 2007/0045619 | A1 | 3/2007 | Park | |
| 2010/0162494 | A1 | 7/2010 | Mueller | |
| 2012/0052296 | A1* | 3/2012 | Ikeno et al. | 428/396 |

FOREIGN PATENT DOCUMENTS

| CN | 1803809 | | 7/2006 |
|---|---|---|---|
| CN | 1990547 | | 7/2007 |
| EP | 1650214 | A | 4/2006 |
| EP | 1810993 | | 7/2007 |
| JP | 2005041963 | A * | 2/2005 |
| WO | 2008/118254 | A | 10/2008 |
| WO | WO 2010119903 | A1 * | 10/2010 |

OTHER PUBLICATIONS

J. Chem. Soc. Dalton. Trans., (1999) pp. 1491-1497.
J. Polymer Science_vol. 40, (2002) pp. 3858-3872.
Crivello et al., Photoinitiators for free radical cationic and anionic photopolymerisation, 2nd Edition, (1998) pp. 83-86.
Macromol Chem. Phys. 197, (1996) pp. 4045-4060.
Macromolecules 28 (1995) pp. 8028-8034.
English-language partial translation for CN1803809 (5 pages); 2006.

* cited by examiner

*Primary Examiner* — Sanza McClendon
(74) *Attorney, Agent, or Firm* — Shruti Costales

(57) ABSTRACT

Photoinitiator compounds comprising both a photoactive moiety and an amine functionality, bonded to a polyhedral oligomeric silsesquioxane, which photoinitiator is represented by formula (1) or (1') wherein n is 2m; m is an integer of 2 to 30; the sum of n'+a is an integer 4-60; n' is an even-numbered integer; a is an even- or uneven-numbered integer; and for example different A $C_1$-$C_{12}$alkyl, or a photoactive moiety Q1, or a group of formula (2); E for example is a direct bond, L is linear or branched $C_1$-$C_3$alkylene, preferably propylene; $R_1$ and $R_2$ for example are a photoactive moiety Q, or $C_{2-20}$alkyl; Q is for example a group of formula (4); $Z_2$ is for example $C_1$-$C_6$alkylene which is unsubstituted or substituted by one or more $OR_6$; and $R_6$, $R_{12}$, $R_{13}$ and $R_{14}$ for example are hydrogen; are especially suitable as low-migrating photoinitiators.

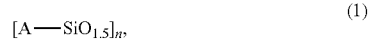

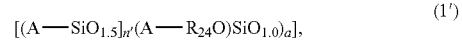

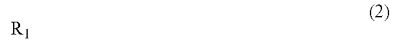

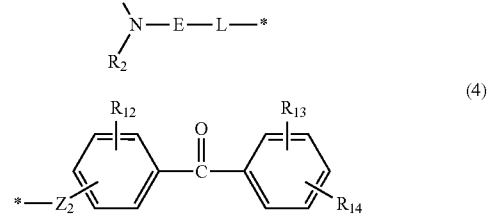

13 Claims, No Drawings

SILSESQUIOXANE PHOTOINITIATORS

The present invention pertains to photoinitiators which are grafted to polyhedral silsequioxane structures and which additionally comprise amine functionalities. Further, mixtures of corresponding compounds as well as their use as photoinitiators is subject of the invention.

Grafting of alpha-hydroxy ketone-type photoinitiators (PI) to fully condensed cage-type polyhedral oligomeric silsesquioxanes (POSS) has been demonstrated by D. Holzinger et al. in *J. Chem. Soc., Dalton Trans.*, 1999, 1491-1497 and in *J. of Polym. Science: Part A: Polymer Chemistry*, 40, 3858-3872, 2002 to afford macroinitiators in which the PI is bonded to the edges of i.e. a cubic cage, thus rendering the PI highly accessible for monomer polymerization by virtue of its unique starlike arrangement. Amines on the other hand are often used together with alpha-hydroxy ketones in order to increase cure speed by virtue of reducing oxygen inhibition (see for example J. V. Crivello, K. Dietliker in *Photoinitiators for Free Radical Cationic & Anionic Photopolymerisation*, G. Bradley (Ed.), John Wiley, New York 1998, pp. 83-86).

Grafting of benzophenones and thioxanthones together with amine-type co-initiators to polymers, i.e. linear polysiloxanes, has been published by X. Coqueret et al. in *Macromol. Chem. Phys.* 197, 4045-4060 (1996) and in *Macromolecules* 1995, 28, 8028-8034 to afford macroinitiators in which the photoactive moieties are randomly bonded to a flexible backbone, thus potentially reducing the accessibility of the photoinitiator for monomer polymerization by virtue of entanglement.

Usually increasing the molecular weight of photoinitiators (e.g. WO 03/033452 or WO 03/033492) affects their reactivity.

Therefore and in particular in printing applications, high molecular weight photoinitiators which are reactive, easy accessible and have a low emission and a low ability to be extracted from the cured ink are attractive, especially if they generate photodecomposition products which also show a low emission and a low ability to migrate.

It has now been found, that photoinitiators grafted together with amine-type co-initiators or synergists (amine functionality) to fully condensed cage-type polyhedral oligomeric silsesquioxanes are useful in such applications, where low migration and low emission of photoinitiator and its photodecomposition products is crucial.

Subject of the invention therefore is a photoinitiator compound comprising both a photoactive moiety and an amine functionality, preferably a tertiary amino group, bonded to a polyhedral oligomeric silsesquioxane.

These photoinitiators provide excellent reactivity in spite of their high molecular weight (MW) and also exhibit low migration and emission properties due to higher MW. The star-like macroinitiators further have reduced sensitivity towards oxygen inhibition, a feature especially useful in thin film applications. Due to the star-like arrangement also the through-cure is excellent through high accessability of the photoinitiator. Further, the photoinitiators provide improved surface-cure properties. This applies in particular for initiators comprising benzophenone or thioxanthone photoactive moieties. Also the yellowing properties of the initiators are satisfactory.

As a photoactive moiety in the above compounds for example corresponding moieties of alpha-hydroxy ketones, benzophenones, thioxanthones, phenylglyoxylates and ketocoumarines are suitable, which are linked to the polyhedral oligomeric silsesquioxane via appropriate linker groups. Examples for such linker groups are the definitions given below for E, $Z_1$-$Z_5$. Specific examples for suitable photoactive moieties including the linker groups are the definitions of $Q_1$ and Q given below.

Interesting are for example compounds which are represented by formula (1) or (1')

wherein
n is 2m;
m is an integer of 2 to 30;
the sum of n'+a is an integer 4-60;
n' is an even-numbered integer, except zero;
a is an even-numbered integer or uneven-numbered integer, except zero;
different A independently of each other are linear or branched $C_1$-$C_{12}$alkyl, $C_2$-$C_{20}$alkyl interrupted by one or more O, cyclopentyl, cyclohexyl, vinyl,

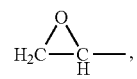

glycidyl-O-L-, $CH_2$=$C(R_5)$—(CO)O-L-,

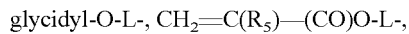

phenyl, halogen-L-, NC-L-, HS-L-, phenyl-L-, $C_5$-$C_6$cycloalkenyl-L-, $C_5$-$C_6$cycloalkyl-L-,

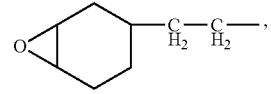

$C(R'_{24})_2$=$C(R_{24})$-L-, $R_{24}O(CO)$-L-, $OR_{24}$ or a photoactive moiety Q1,
or different A independently of each other are a group of formula (2)

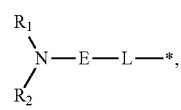

wherein the asterisk * denotes the bond to the silicon;
E is a direct bond, linear or branched $C_2$-$C_6$alkylene-O or linear or branched $C_2$-$C_6$alkylene-S which $C_2$-$C_6$alkylene-O and $C_2$-$C_6$alkylene-S are unsubstituted or substituted by one or more $OR_6$,
or E is linear or branched $C_1$-$C_6$alkylene(CO)O, or E is

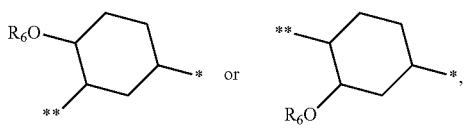

wherein the asterisk * denotes the bond to L and the double asterix ** denotes the bond to the N-atom, or E is linear or branched $C_2$-$C_6$alkyleneN($R_3$) or linear or branched $C_2$-$C_6$alkylene($NR_3$)$C_2$-$C_6$alkyleneN($R_4$);

L is linear or branched $C_1$-$C_4$alkylene, preferably propylene, or is linear or branched $C_2$-$C_4$alkylene which is substituted by $OR_6$;

or L, if E is a direct bond or linear or branched $C_2$-$C_6$alkyleneN($R_3$), additionally is linear or branched $C_2$-$C_4$alkylene which is interrupted by phenylene;

or L, if E is a direct bond, additionally is phenylene;

$R_1$ and $R_2$ independently of each other are a photoactive moiety Q, hydrogen, $C_6$-$C_{14}$aryl which is unsubstituted or is substituted by one or more $R_{32}$, or $R_1$ and $R_2$ are linear or branched $C_1$-$C_6$alkyl which is unsubstituted or substituted by one or more $OR_6$, $SR_{29}$, $NR_7R_8$, (CO)$R_{24}$, (CO)$OR_{24}$, (CO)N($R_{16}$)($R'_{16}$), CN, C($R_{24}$)=C($R'_{24}$)$_2$ or by $C_6$-$C_{14}$aryl or by O $C_6$-$C_{14}$aryl both of which aryl are unsubstituted or substituted by $R_{32}$;

or $R_1$ and $R_2$ independently of each other are linear or branched $C_2$-$C_{26}$alkyl which is interrupted by one or more O, O(CO), (CO)O, C($R_{24}$)=C($R'_{24}$), or $R_{16}$N(CO) and which interrupted $C_2$-$C_{26}$alkyl is unsubstituted or substituted by one or more $OR_6$, $SR_{29}$, $NR_7R_8$, (CO)$R_{24}$, (CO)$OR_{24}$, (CO)N($R_{16}$)($R'_{16}$), C($R_{24}$)=C($R'_{24}$)$_2$ or by CN;

or $R_1$ and $R_2$ independently of each other are $C_5$-$C_6$cycloalkyl which is unsubstituted or substituted by one or more $OR_6$ or $SR_{29}$;

or $R_1$ and $R_2$ independently of each other are (CO)$C_1$-$C_3$alkylene-$OR_{25}$,

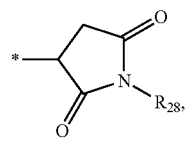

(CO)$R_{16}$, (CO)N($R_{16}$)($R_{30}$), (CO)$OR_{30}$, (PO)($OR_{30}$)$_2$ or $R_{30}$(SO$_2$);

or $R_1$ and $R_2$ together with the nitrogen atom to which they are bonded form a group

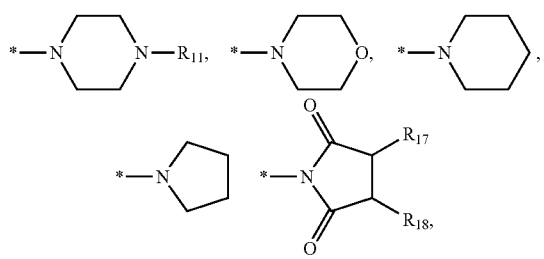

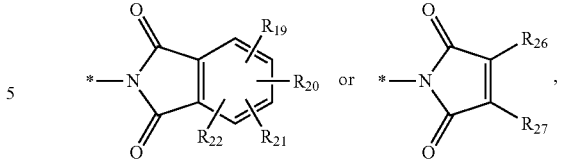

wherein the asterisk * denotes the bond to E;

$R_3$ and $R_4$ independently of each other are a photoactive moiety Q, hydrogen, $C_6$-$C_{14}$aryl which is unsubstituted or is substituted by one or more $R_{32}$, linear or branched $C_1$-$C_6$alkyl which is unsubstituted or substituted by one or more $OR_6$, $SR_{29}$, $NR_7R_8$, (CO)$R_{24}$, (CO)$OR_{24}$, (CO)N($R_{16}$)($R'_{16}$), C($R_{24}$)=C($R'_{24}$)$_2$, CN or by $C_6$-$C_{14}$aryl which optionally is substituted by $R_{32}$; or $R_3$ and $R_4$ independently of each other are linear or branched $C_2$-$C_{26}$alkyl which is interrupted by one or more O, O(CO), (CO)O, C($R_{24}$)=C($R_{24}$) or $R_{16}$N(CO) and which interrupted $C_2$-$C_{26}$alkyl is unsubstituted or substituted by one or more $OR_6$, $SR_{29}$, $NR_7R_8$, (CO)$R_{24}$, (CO)$OR_{24}$, (CO)N($R_{16}$)($R'_{16}$), C($R_{24}$)=C($R'_{24}$)$_2$ or by CN;

or $R_3$ and $R_4$ independently of each other are $C_6$-$C_6$cycloalkyl which is unsubstituted or substituted by one or more $OR_6$ or $SR_{29}$;

or $R_3$ and $R_4$ independently of each other are (CO)$C_1$-$C_3$alkylene-$OR_{25}$,

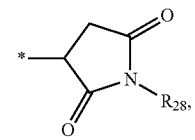

(CO)$R_{16}$, (CO)N($R_{16}$)($R'_{16}$), (CO)$OR_{30}$, (PO)($OR_{30}$)$_2$ or $R_{30}$(SO$_2$);

$R_5$ is hydrogen or linear or branched $C_1$-$C_6$alkyl;

$R_6$ is hydrogen, $C_1$-$C_8$alkyl, Si(CH$_3$)$_3$, (CO)$R_{15}$, (CO)N($R_{16}$)($R_{30}$),

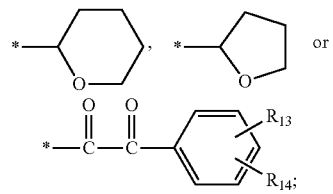

$R_7$ and $R_8$ independently of each other are linear or branched $C_1$-$C_6$alkyl or phenyl, or $R_7$ and $R_8$ together with the nitrogen atom to which they are bonded form a group

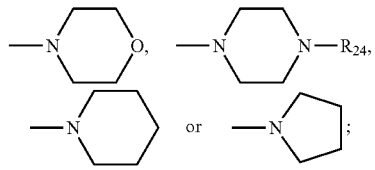

Q is a group of formula (3), (4), (5), (6), (6a) or (7)

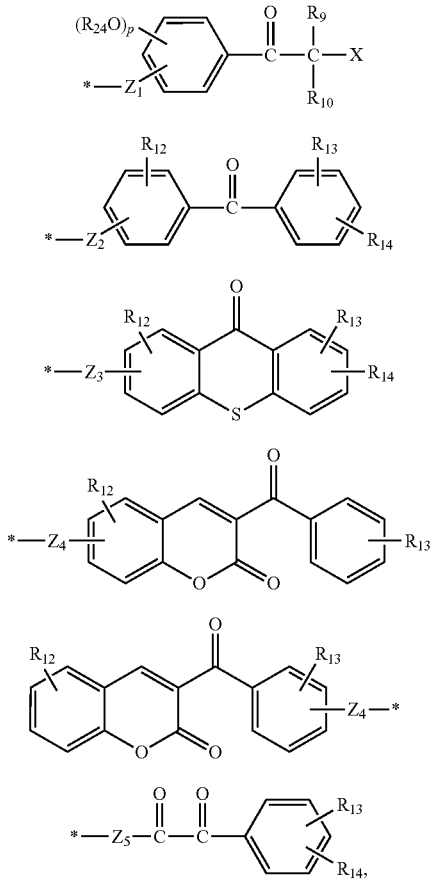

in which formulae (3), (4), (5), (6), (6a) and (7) the asterisk * denotes the bonding to the nitrogen in formula (2);

Q1 is a group of formula (8), (9), (10), (11), (11a) or (12)

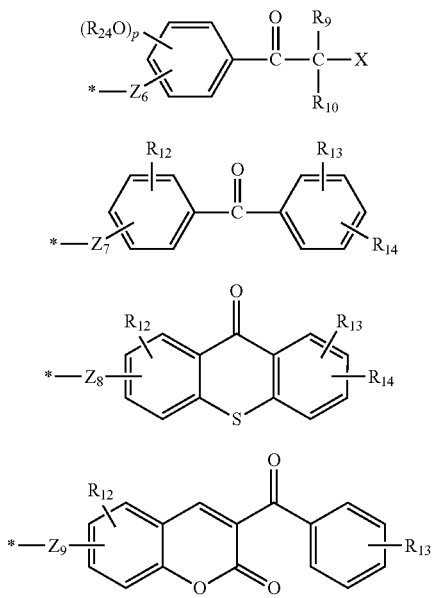

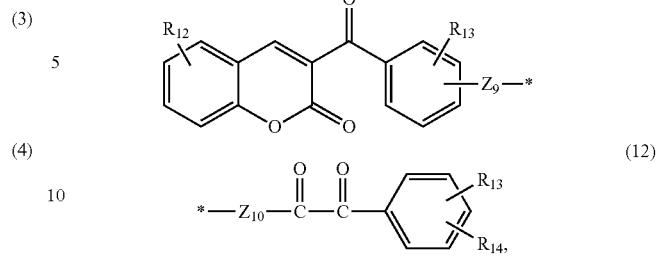

in which formulae (8), (9) (10), (11), (11a) and (12) the asterisk * denotes the bonding to the silicon atom;

p is an integer 0, 1, 2, 3 or 4;

$Z_1$, $Z_2$, $Z_3$ and $Z_4$ independently of each other denote a direct bond, CO, $C_1$-$C_6$alkylene which is unsubstituted or substituted by one or more $OR_6$, or independently of each other are $C_2$-$C_6$alkylene which is interrupted by one or more O or O(CO) and which is unsubstituted or substituted by one or more $OR_6$, or independently of each other are $OC_1$-$C_6$alkylene which is unsubstituted or substituted by one or more $OR_6$, or independently of each other are $OC_2$-$C_{12}$alkylene which is interrupted by one or more O, (CO)O or O(CO) and which is unsubstituted or substituted by one or more $OR_6$, or independently of each other are $SC_1$-$C_{12}$alkylene which is unsubstituted or substituted by one or more $OR_6$, or independently of each other are $SC_2$-$C_{12}$alkylene which is interrupted by one or more O or O(CO), or are O—$C_1$-$C_6$alkylene-(CO) or S—$C_1$-$C_6$alkylene-(CO);

in which definitions the double asterisk ** denotes the bonding to the phenyl ring;

$Z_5$ is a direct bond, linear or branched O—$C_2$-$C_6$alkylene which is unsubstituted or substituted by one or more $OR_6$;

or is linear or branched O—$C_2$-$C_8$alkylene interrupted by one or more O and which is unsubstituted or substituted by one or more $OR_6$;

$Z_6$, $Z_7$, $Z_8$ and $Z_9$ independently of each other are linear or branched —$C_1$-$C_3$alkylene-, -O-L-, -O-E1-L-, $C_1$-$C_6$alkylene-O-L-, -O—$C_2$-$C_6$alkylene-O-L-, -O—$C_2$-$C_6$alkylene-S-L-, -O—$C_2$-$C_6$alkylene-S-E1-L-, -S-L-, -S-E1-L-, $C_1$-$C_6$alkylene-S-L-, $C_1$-$C_6$alkylene-S-E1-L-, -S—$C_2$-$C_6$alkylene-S-L-, -S—$C_2$-$C_6$alkylene-S-E1-L-, -S—$C_2$-$C_6$alkylene-O-L-, -(CO)—O-L-, **-(CO)—O-E2-L-*, $C_1$-$C_6$alkylene-(CO)—O-L-, $C_1$-$C_6$alkylene-(CO)—O-E2-L-, O—$C_1$-$C_6$alkylene-(CO)—O-L-, O—$C_1$-$C_6$alkylene-(CO)—O-E2-L-, S—$C_1$-$C_6$alkylene-(CO)—O-L- or S—$C_1$-$C_6$alkylene-(CO)—O-E2-L-, in which definitions the double asterisk ** denotes the bonding to the phenyl ring;

$Z_{10}$ is -O-L- or -O-E2-L-, in which definitions the double asterisk ** denotes the bonding to the phenyl ring;

E1 is

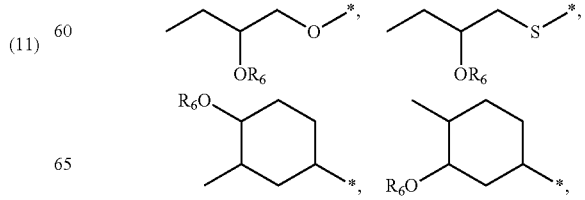

-continued

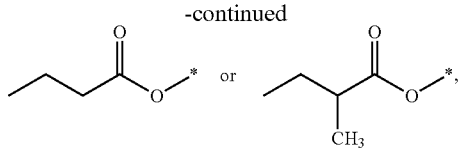

in which definitions the asterisk * denotes the bonding to L;
E2 is

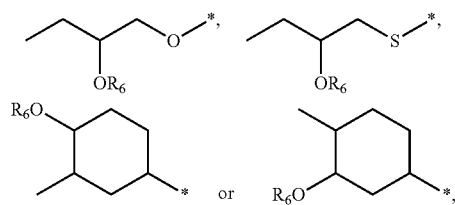

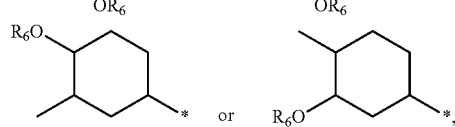

in which definitions the asterisk * denotes the bonding to L;

X is $OR_5$ or $NR_7R_8$;

$R_9$ and $R_{10}$ independently of each other are $C_1$-$C_6$alkyl, $C_2$-$C_{12}$alkenyl or phenyl$C_1$-$C_3$alkyl which is unsubstituted or substituted by one or more $C_1$-$C_6$alkyl;

$R_{11}$ has one of the definitions given for $R_1$ and $R_2$;

$R_{12}$, $R_{13}$ and $R_{14}$ independently of each other are hydrogen, linear or branched $C_1$-$C_{12}$alkyl which is unsubstituted or substituted by one or more OH, $C_1$-$C_4$alkoxy, phenyl, halogen or by CN; or $R_{12}$, $R_{13}$ and $R_{14}$ independently of each other are $C_2$-$C_{12}$alkyl which is interrupted by one or more non-consecutive O; or $R_{12}$, $R_{13}$ and $R_{14}$ are halogen, OH, $NR_7R_8$, $(CO)R_{23}$, $C_1$-$C_{12}$alkoxy, $C_1$-$C_{12}$alkylthio, —$(C_1$-$C_6$alkyl)-$NR_7R_8$ or —O—$(C_1$-$C_6$alkyl)$NR_7R_8$;

$R_{15}$ is hydrogen, linear or branched $C_1$-$C_{20}$alkyl which unsubstituted or substituted by $C(R_{24})$=$C(R_{24})_2$ or $N(R_7)(R_8)$, or is $C_2$-$C_{20}$alkyl which is interrupted by one or more O or $C(R_{24})$=$C(R_{24})$; or is phenyl which is unsubstituted or is substituted by one or more $C_1$-$C_4$alkyl, halogen, $C_1$-$C_4$alkoxy, $N(R_7)(R_8)$ or $C_1$-$C_4$alkylthio, or $R_{15}$ is $C_5$-$C_6$-cycloalkyl,

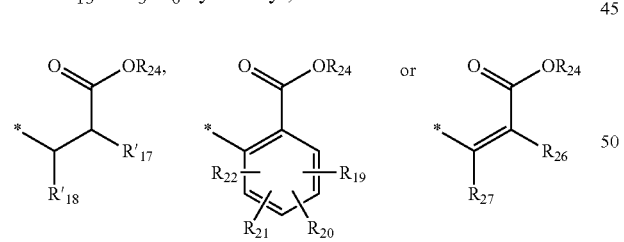

wherein the asterisk * represents the bond to the C-atom of the carbonyl group of $(CO)R_{15}$;

$R_{16}$ and $R'_{16}$ independently of one another are hydrogen, phenyl or linear or branched $C_1$-$C_6$alkyl;

$R_{17}$, $R'_{17}$, $R_{18}$ and $R'_{18}$ independently of one another are hydrogen, linear or branched $C_1$-$C_{20}$alkyl which is unsubstituted or substituted by one or more $C(R_{24})$=$C(R_{24})_2$, or is linear or branched $C_2$-$C_{20}$alkyl which is interrupted by $C(R_{24})$=$C(R_{24})$;

or $R_{17}$ and $R_{18}$ together with the C-atoms to which they are bonded form

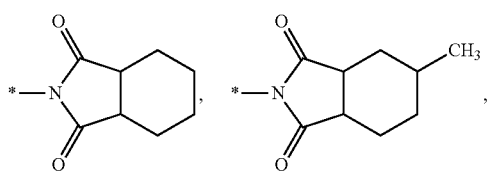

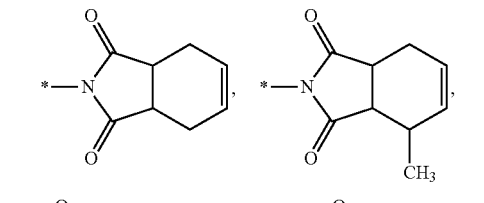

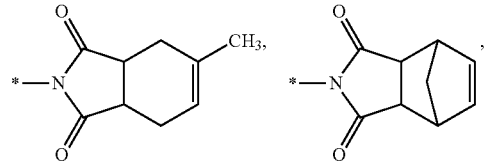

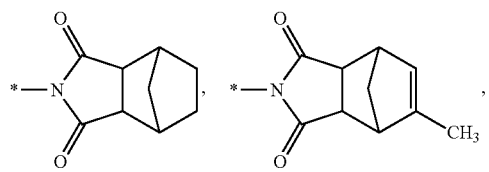

wherein the asterisk * denotes the bond to E, or $R'_{17}$ and $R'_{18}$ together with the C-atoms to which they are bonded form

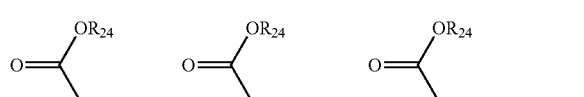
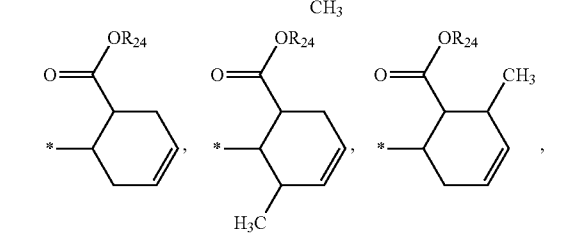

-continued

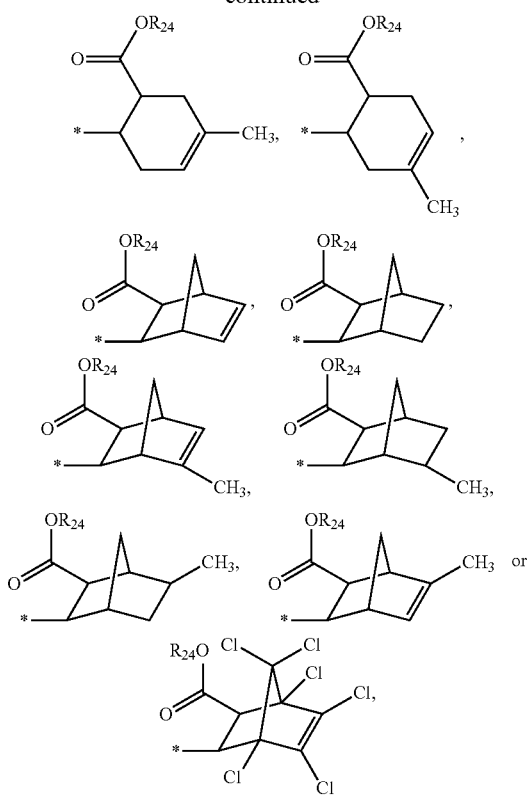

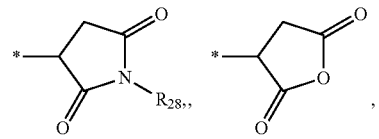

Si(CH$_3$)$_3$, (CO)R$_{31}$, (CO)N(R$_{16}$)(R$_{30}$),

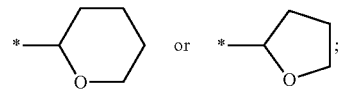

R$_{30}$ phenyl or linear or branched C$_1$-C$_6$alkyl;

R$_{31}$ is hydrogen, linear or branched C$_1$-C$_{20}$alkyl which unsubstituted or substituted by C(R$_{24}$)=C(R$_{24}$)$_2$, or is C$_2$-C$_{20}$alkyl which is interrupted by one or more O or C(R$_{24}$)=C(R$_{24}$); or is phenyl which is unsubstituted or is substituted by one or more C$_1$-C$_4$alkyl, halogen, C$_1$-C$_4$alkoxy or by C$_1$-C$_4$alkylthio, or R$_{31}$ is C$_5$-C$_6$-cycloalkyl,

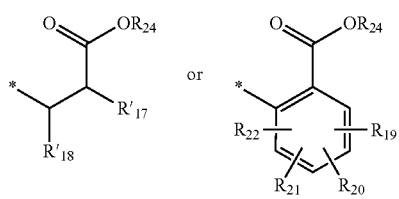

wherein the asterisk * denotes the bond to the C-atom of the carbonyl group in (CO)R$_{15}$;

R$_{19}$, R$_{20}$, R$_{21}$ and R$_{22}$ independently of one another are hydrogen, Cl or methyl;

R$_{23}$ is C$_1$-C$_6$alkyl, phenyl which is unsubstituted or is substituted by one or more C$_1$-C$_4$alkyl, halogen, C$_1$-C$_4$alkoxy or by C$_1$-C$_4$alkylthio;

R$_{24}$, R'$_{24}$, R$_{26}$ and R$_{27}$ independently of one another are hydrogen or C$_1$-C$_6$alkyl;

R$_{25}$ is hydrogen, Si(CH$_3$)$_3$, (CO)R$_{15}$, (CO)N(R$_{16}$)(R$_{30}$),

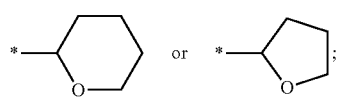 [SMILES: *C1CCCCO1 ; *C1CCCO1]

R$_{28}$ is hydrogen, linear or branched C$_1$-C$_6$alkyl which unsubstituted or is substituted by phenyl; or is C$_5$-C$_6$cycloalkyl or phenyl which is unsubstituted or substituted by one or more C$_1$-C$_4$alkyl or by halogen;

R$_{29}$ is hydrogen, linear or branched C$_1$-C$_6$alkyl which is unsubstituted or substituted by one or more OH, NR$_7$R$_8$, (CO)R$_{24}$, (CO)OR$_{24}$, (CO)N(R$_{16}$)(R'$_{16}$) or by CN, or R$_{29}$ is linear or branched C$_2$-C$_{20}$alkyl which is interrupted by one or more O, O(CO) or N(R$_{16}$)(CO) and which interrupted C$_2$-C$_{20}$alkyl is unsubstituted or is substituted by one or more OH, NR$_7$R$_8$, (CO)R$_{24}$, (CO)OR$_{24}$, or by (CO)N(R$_{16}$)(R'$_{16}$), or R$_{29}$ is wherein the asterisk * represents the bond to the C-atom of the carbonyl group of (CO)R$_{31}$; and R$_{32}$ is halogen, CN, OH, C$_1$-C$_4$alkoxy, (CO)OR$_{24}$, NR$_7$R$_8$, vinyl or C$_1$-C$_6$alkyl which is unsubstituted or is substituted by one or more CN, OH, (CO)R$_{24}$ or by NR$_8$R$_9$;

provided that at least one Q and at least one amine functionality via a group of the formula (2) are present in the photoinitiator compound.

Interesting further are compounds of the formula (1)

$$[A\text{—}SiO_{1.5}]_n, \tag{1}$$

wherein n is 2m;

m is an integer of 2 to 30;

different A independently of each other are linear or branched C$_1$-C$_{12}$alkyl, cyclopentyl, cyclohexyl, vinyl,

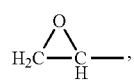

glycidyl-O-L-, $CH_2=C(R_5)-(CO)O-L-$,

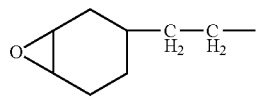

or a photoactive moiety Q1,
or different A independently of each other are a group of formula (2)

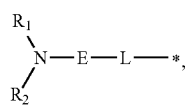  (2)

wherein the asterisk * denotes the bond to the silicon;
E is a direct bond, linear or branched $C_2$-$C_6$alkylene-O or linear or branched $C_2$-$C_6$alkylene-S which $C_2$-$C_6$alkylene-O and $C_2$-$C_6$alkylene-S are unsubstituted or substituted by one or more $OR_6$,
or E is linear or branched $C_1$-$C_6$alkylene(CO)O,
or E is

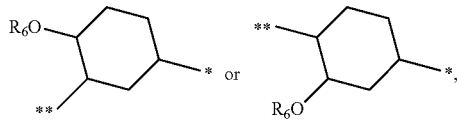

wherein the asterisk * denotes the bond to L and the double asterix ** denotes the bond to the N-atom,
or E is linear or branched $C_2$-$C_6$alkyleneN($R_3$) or linear or branched $C_2$-$C_6$alkylene(N$R_3$)$C_2$-$C_6$alkyleneN($R_4$);
L is linear or branched $C_1$-$C_3$alkylene, preferably propylene, or is linear or branched $C_2$-$C_3$alkylene which is substituted by $OR_6$;
$R_1$ and $R_2$ independently of each other are a photoactive moiety Q, hydrogen, $C_6$-$C_{14}$aryl which is unsubstituted or is substituted by one or more $R_{32}$, or $R_1$ and $R_2$ are linear or branched $C_1$-$C_6$alkyl which is unsubstituted or substituted by one or more $OR_6$, $SR_{29}$, $NR_7R_8$, $(CO)R_{24}$, $(CO)OR_{24}$, $(CO)N(R_{16})(R'_{16})$, $C_6$-$C_{14}$aryl, $C(R_{24})=C(R'_{24})_2$ or by CN;
or $R_1$ and $R_2$ independently of each other are linear or branched $C_2$-$C_{20}$alkyl which is interrupted by one or more O, O(CO), $C(R_{24})=C(R'_{24})$, or $R_{16}$N(CO) and which interrupted $C_2$-$C_{20}$alkyl is unsubstituted or substituted by one or more $OR_6$, $SR_{29}$, $NR_7R_8$, $(CO)R_{24}$, $(CO)OR_{24}$, $(CO)N(R_{16})(R'_{16})$, $C(R_{24})=C(R'_{24})$ or by CN;
or $R_1$ and $R_2$ independently of each other are $C_5$-$C_6$cycloalkyl which is unsubstituted or substituted by one or more $OR_6$ or $SR_{29}$;
or $R_1$ and $R_2$ independently of each other are (CO)$C_1$-$C_3$alkylene-$OR_{25}$,

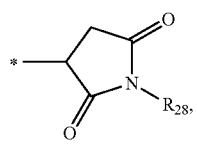

$(CO)R_{15}$, $(CO)N(R_{16})(R_{30})$, $(CO)OR_{30}$, $(PO)(OR_{30})_2$ or $R_{30}(SO_2)$;

or $R_1$ and $R_2$ together with the nitrogen atom to which they are bonded form a group

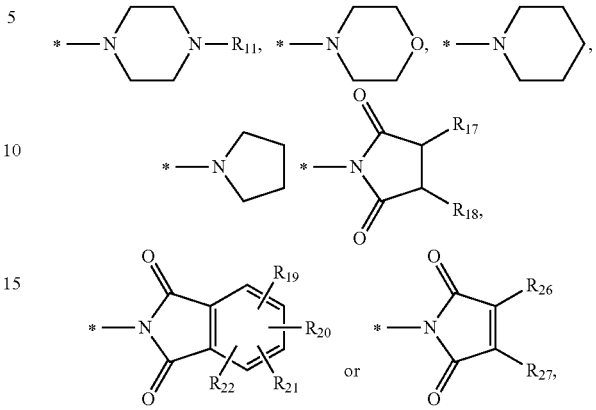

wherein the asterisk * denotes the bond to E;
$R_3$ and $R_4$ independently of each other are a photoactive moiety Q, hydrogen, linear or branched $C_1$-$C_6$alkyl which is unsubstituted or substituted by one or more $OR_6$, $SR_{29}$, $NR_7R_8$, $(CO)R_{24}$, $(CO)OR_{24}$, $(CO)N(R_{16})(R'_{16})$, $C_6$-$C_{14}$aryl, $C(R_{24})=C(R'_{24})_2$ or by CN; or $R_3$ and $R_4$ independently of each other are linear or branched $C_2$-$C_{20}$alkyl which is interrupted by one or more O, O(CO), $C(R_{24})=C(R_{24})$ or $R_{16}$N (CO) and which interrupted $C_2$-$C_{20}$alkyl is unsubstituted or substituted by one or more $OR_6$, $SR_{29}$, $NR_7R_8$, $(CO)R_{24}$, $(CO)OR_{24}$, $(CO)N(R_{16})(R'_{16})$, $C(R_{24})=C(R'_{24})_2$ by CN;
or $R_3$ and $R_4$ independently of each other are $C_6$-$C_6$cycloalkyl which is unsubstituted or substituted by one or more $OR_6$ or $SR_{29}$;
or $R_3$ and $R_4$ independently of each other are (CO)$C_1$-$C_3$alkylene-$OR_{25}$,

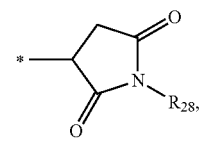

$(CO)R_{16}$, $(CO)N(R_{16})(R'_{16})$, $(CO)OR_{30}$, $(PO)(OR_{30})_2$ or $R_{30}(SO_2)$;
$R_5$ is hydrogen or linear or branched $C_1$-$C_6$alkyl;
$R_6$ is hydrogen, $Si(CH_3)_3$, $(CO)R_{16}$, $(CO)N(R_{16})(R_{39})$,

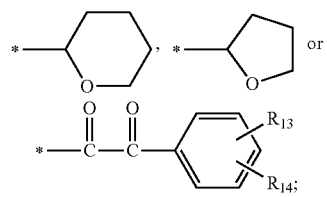

$R_7$ and $R_8$ independently of each other are linear or branched $C_1$-$C_6$alkyl or phenyl, or $R_7$ and
$R_8$ together with the nitrogen atom to which they are bonded form a group

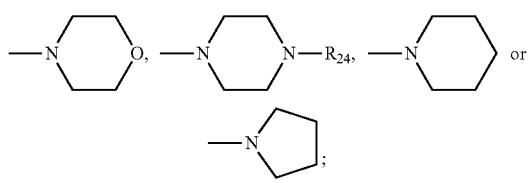

Q is a group of formula (3), (4), (5), (6) or (7)

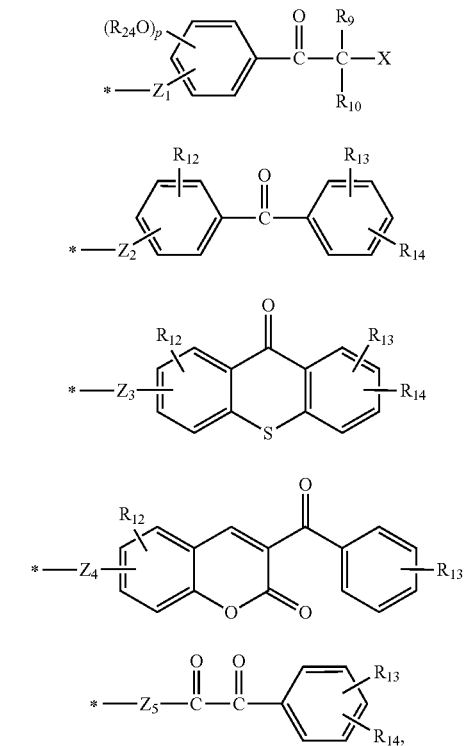

in which formulae (3), (4), (5), (6) and (7) the asterisk * denotes the bonding to the nitrogen in formula (2);

Q1 is a group of formula (8), (9), (10), (11) or (12)

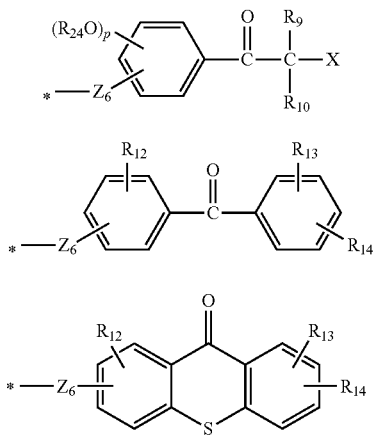

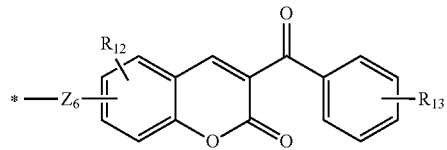

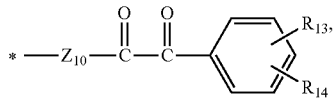

in which formulae (8), (9) (10), (11) and (12) the asterisk * denotes the bonding to the silicon atom;

p is an integer 0, 1, 2, 3 or 4;

$Z_1$, $Z_2$, $Z_3$ and $Z_4$ independently of each other denote a direct bond, CO, $C_1$-$C_6$alkylene which is unsubstituted or substituted by one or more $OR_6$, or independently of each other are $C_2$-$C_6$alkylene which is interrupted by one or more O or O(CO) and which is unsubstituted or substituted by one or more $OR_6$, or independently of each other are $OC_1$-$C_6$alkylene which is unsubstituted or substituted by one or more $OR_6$, or independently of each other are $OC_2$-$C_{12}$alkylene which is interrupted by one or more O or O(CO) and which is unsubstituted or substituted by one or more $OR_6$, or independently of each other are $SC_1$-$C_{12}$alkylene which is unsubstituted or substituted by one or more $OR_6$, or independently of each other are $SC_2$-$C_{12}$alkylene which is interrupted by one or more O or O(CO), or are O—$C_1$-$C_6$alkylene-(CO) or S—$C_1$-$C_6$alkylene-(CO);

in which definitions the double asterisk ** denotes the bonding to the phenyl ring;

$Z_5$ is a direct bond, linear or branched O—$C_2$-$C_6$alkylene which is unsubstituted or substituted by one or more $OR_6$;

$Z_6$, $Z_7$, $Z_8$ and $Z_9$ independently of each other are linear or branched —$C_1$-$C_3$alkylene-, -O-L-,-O-E1-L-, $C_1$-$C_6$alkylene-O-L-, -O—$C_2$-$C_6$alkylene-O-L-, -O—$C_2$-$C_6$alkylene-S-L-, -O—$C_2$-$C_6$alkylene-S-E1-L-, -S-L-, -S-E1-L-, $C_1$-$C_6$alkylene-S-L-, $C_1$-$C_6$alkylene-S-E1-L-, -S—$C_2$-$C_6$alkylene-S-L-, -S—$C_2$-$C_6$alkylene-S-E1-L-, -S—$C_2$-$C_6$alkylene-O-L-, -(CO)—O-L-, **-(CO)—O-E2-L-*, $C_1$-$C_6$alkylene-(CO)—O-L-, $C_1$-$C_6$alkylene-(CO)—O-E2-L-, O—$C_1$-$C_6$alkylene-(CO)—O-L-, O—$C_1$-$C_6$alkylene-(CO)—O-E2-L-, S—$C_1$-$C_6$alkylene-(CO)—O-L- or S—$C_1$-$C_6$alkylene-(CO)—O-E2-L-, in which definitions the double asterisk ** denotes the bonding to the phenyl ring;

$Z_{10}$ is -O-L- or -O-E2-L-, in which definitions the double asterisk ** denotes the bonding to the phenyl ring;

E1 is

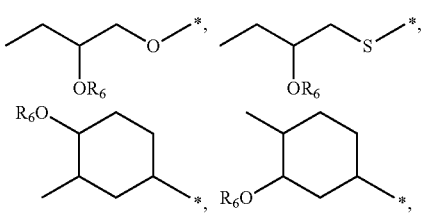

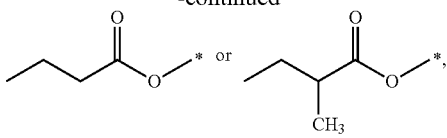

in which definitions the asterisk * denotes the bonding to L;

E2 is

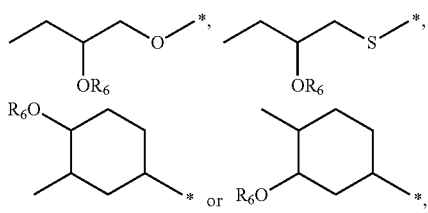

in which definitions the asterisk * denotes the bonding to L;

X is $OR_5$ or $NR_7R_8$;

$R_9$ and $R_{10}$ independently of each other are $C_1$-$C_6$alkyl, $C_2$-$C_{12}$alkenyl or phenyl$C_1$-$C_3$alkyl which is unsubstituted or substituted by one or more $C_1$-$C_6$alkyl;

$R_{11}$ has one of the definitions given for $R_1$ and $R_2$;

$R_{12}$, $R_{13}$ and $R_{14}$ independently of each other are hydrogen, linear or branched $C_1$-$C_{12}$alkyl which is unsubstituted or substituted by one or more OH, $C_1$-$C_4$alkoxy, phenyl, halogen or by CN; or $R_{12}$, $R_{13}$ and $R_{14}$ independently of each other are $C_2$-$C_{12}$alkyl which is interrupted by one or more nonconsecutive O; or $R_{12}$, $R_{13}$ and $R_{14}$ are halogen, OH, $NR_7R_8$, $(CO)R_{23}$, $C_1$-$C_{12}$alkoxy, $C_1$-$C_{12}$alkylthio, -($C_1$-$C_6$alkyl)-$NR_7R_8$ or —O—($C_1$-$C_6$alkyl)$NR_7R_8$;

$R_{15}$ is hydrogen, linear or branched $C_1$-$C_{20}$alkyl which unsubstituted or substituted by $C(R_{24})$=$C(R_{24})_2$, or is $C_2$-$C_{20}$alkyl which is interrupted by one or more O or $C(R_{24})$=$C(R_{24})$; or is phenyl which is unsubstituted or is substituted by one or more $C_1$-$C_4$alkyl, halogen, $C_1$-$C_4$alkoxy or $C_1$-$C_4$alkylthio, or $R_{15}$ is $C_6$-$C_6$-cycloalkyl,

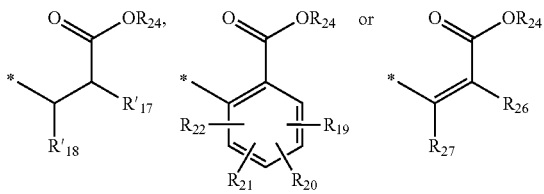

wherein the asterisk * represents the bond to the C-atom of the carbonyl group of $(CO)R_{16}$;

$R_{16}$ and $R'_{16}$ independently of one another are hydrogen, phenyl or linear or branched $C_1$-$C_6$alkyl;

$R_{17}$, $R'_{17}$, $R_{18}$ and $R'_{18}$ independently of one another are hydrogen, linear or branched $C_1$-$C_{20}$alkyl which is unsubstituted or substituted by one or more $C(R_{24})$=$C(R_{24})_2$, or is linear or branched $C_2$-$C_{20}$alkyl which is interrupted by $C(R_{24})$=$C(R_{24})$;

or $R_{17}$ and $R_{18}$ together with the C-atoms to which they are bonded form

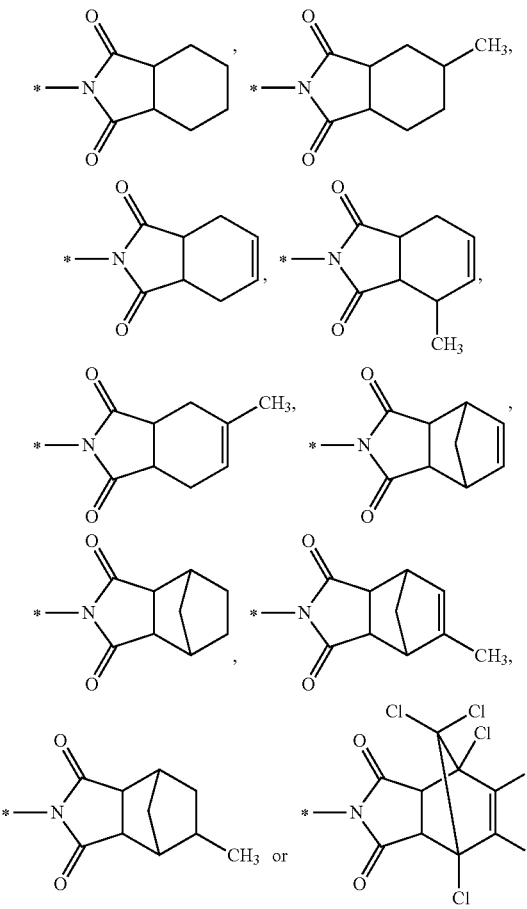

wherein the asterisk * denotes the bond to E, or $R'_{17}$ and $R'_{18}$ together with the C-atoms to which they are bonded form

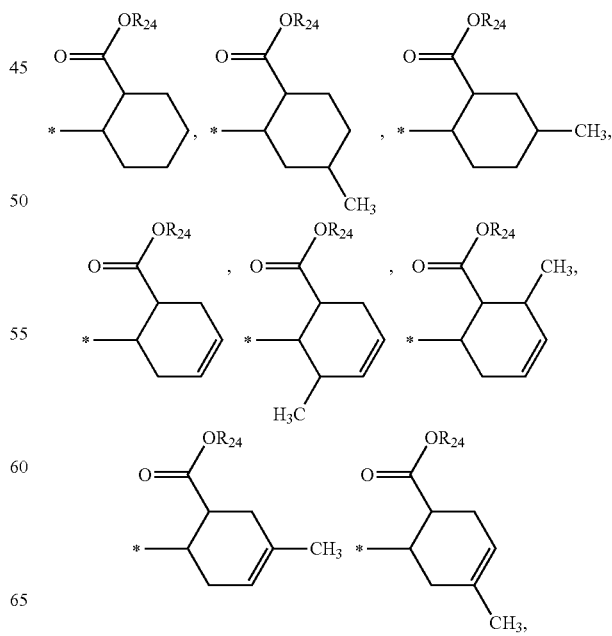

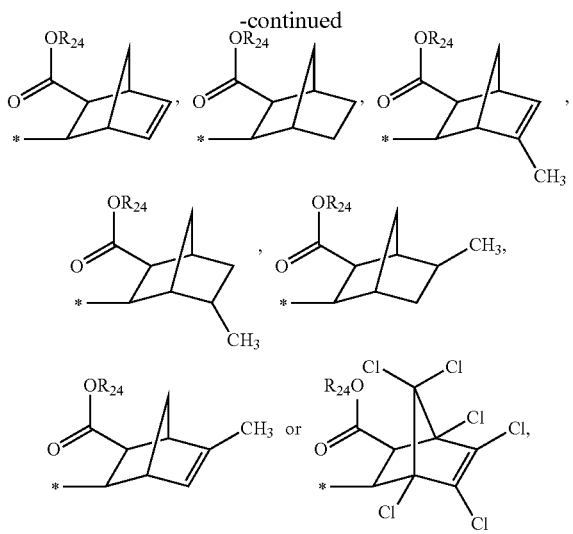

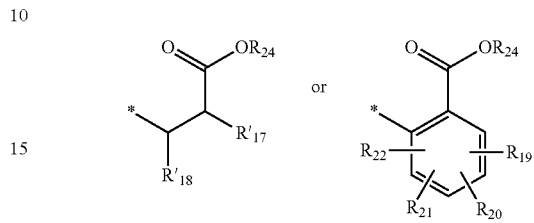

wherein the asterisk * denotes the bond to the C-atom of the carbonyl group in $(CO)R_{15}$;

$R_{19}$, $R_{20}$, $R_{21}$ and $R_{22}$ independently of one another are hydrogen, Cl or methyl;

$R_{23}$ is $C_1$-$C_6$alkyl, phenyl which is unsubstituted or is substituted by one or more $C_1$-$C_4$alkyl, halogen, $C_1$-$C_4$alkoxy or by $C_1$-$C_4$alkylthio;

$R_{24}$, $R'_{24}$, $R_{26}$ and $R_{27}$ independently of one another are hydrogen or $C_1$-$C_6$alkyl;

$R_{25}$ is hydrogen, $Si(CH_3)_3$, $(CO)R_{15}$, $(CO)N(R_{16})(R_{30})$,

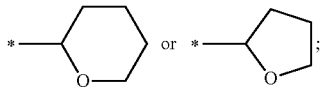

$R_{28}$ is hydrogen, linear or branched $C_1$-$C_6$alkyl which is unsubstituted or is substituted by phenyl; or is $C_5$-$C_6$cycloalkyl or phenyl which is unsubstituted or substituted by one or more $C_1$-$C_4$alkyl or by halogen;

$R_{29}$ is hydrogen, linear or branched $C_1$-$C_6$alkyl which is unsubstituted or substituted by one or more OH, $NR_7R_8$, $(CO)R_{24}$, $(CO)OR_{24}$, $(CO)N(R_{16})(R'_{16})$ or by CN, or $R_{29}$ is linear or branched $C_2$-$C_{20}$alkyl which is interrupted by one or more O, O(CO) or $N(R_{16})(CO)$ and which interrupted $C_2$-$C_{20}$alkyl is unsubstituted or is substituted by one or more OH, $NR_7R_8$, $(CO)R_{24}$, $(CO)OR_{24}$, or by $(CO)_N(R_{16})(R'_{16})$, or $R_{29}$ is

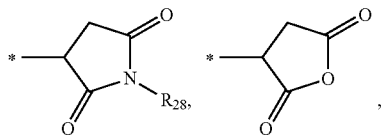

$Si(CH_3)_3$, $(CO)R_{31}$, $(CO)N(R_{16})(R_{30})$,

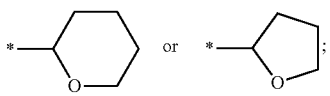 [SMILES: *C1CCCCO1 ; *C1CCCO1]

$R_{30}$ phenyl or linear or branched $C_1$-$C_6$alkyl;

$R_{31}$ is hydrogen, linear or branched $C_1$-$C_{20}$alkyl which unsubstituted or substituted by $C(R_{24})\!=\!C(R_{24})_2$, or is $C_2$-$C_{20}$alkyl which is interrupted by one or more O or $C(R_{24})$ $=\!C(R_{24})$; or is phenyl which is unsubstituted or is substituted by one or more $C_1$-$C_4$alkyl, halogen, $C_1$-$C_4$alkoxy or by $C_1$-$C_4$alkylthio, or $R_{31}$ is $C_5$-$C_6$-cycloalkyl, wherein the asterisk * represents the bond to the C-atom of the carbonyl group of $(CO)R_{31}$; and $R_{32}$ is halogen, CN, OH, $C_1$-$C_4$alkoxy, $(CO)OR_{24}$, $NR_7R_8$ or $C_1$-$C_6$alkyl which is unsubstituted or is substituted by one or more CN, OH, $(CO)R_{24}$ or by $NR_8R_9$;

provided that at least one Q and at least one amine functionality via a group of the formula (2) are present in the photoinitiator compound.

Regardless whether it is explicitly stated in the claims all definitions "alkyl" and "alkylene", standing single or in connection with a defined group, e.g. Oalkylene etc. are meant to be linear or branched.

$C_1$-$C_{26}$alkyl is linear or branched and is, for example $C_1$-$C_{24}$-, $C_1$-$C_{12}$-, $C_1$-$C_{10}$-, $C_1$-$C_6$-, $C_1$-$C_6$— or $C_1$-$C_4$alkyl. Examples are methyl, ethyl, propyl, isopropyl, n-butyl, sec-butyl, isobutyl, tertbutyl, pentyl, hexyl, heptyl, 2,4,4-trimethylpentyl, 2-ethylhexyl, octyl, nonyl, decyl or dodecyl. $C_1$-$C_6$alkyl and $C_1$-$C_4$alkyl have the same meanings as given above for $C_1$-$C_{26}$alkyl up to the corresponding number.

Alkyl which is substituted one or more times by a defined substitutent is for examples substituted 1-8, 1-6, 1-4, 1-3, or twice or once by the corresponding substituents.

Linear or branched $C_2$-$C_{26}$alkyl which is interrupted by one or more O, (CO)O or $(CO)NR_5$ is for example interrupted 1-8, 1-6, 1-4, 1-3, or twice or once by the one or more of the defined groups resulting for example in structures like —$CH_2$—O—$CH_3$, —$CH_2CH_2$—O—$CH_2CH_3$, —[$CH_2CH_2$O]$_y$—$CH_3$, with y=1-9, —($CH_2CH_2$O)$_7$ $CH_2CH_3$, —$CH_2$—$CH(CH_3)$—O—$CH_2$—$CH_2CH_3$, or —$CH_2$—$CH(CH_3)$—O—$CH_2CH_3$, —$CH_2$—(CO)O—$CH_3$, —$CH_2CH_2$—(CO)O—$CH_2CH_3$, $CH_2$—(CO)$NR_5$—$CH_3$, $CH_2CH_2$—(CO)$NR_5$—$CH_3$, —$CH_2CH_2$—(CO)$NR_5$—$CH_2CH_3$ etc.

In case the groups are interrupted by more than one O, said O-atoms are separated from one another by at least one methylene group, i.e. the O-atoms are non-consecutive.

Interrupted $C_2$-$C_{26}$alkyl which is substituted one or more times by a defined substitutent is for examples substituted 1-8, 1-6, 1-4, 1-3, or twice or once by the corresponding substituents.

$C_5$-$C_6$cycloalkyl is cyclopentyl or cyclohexyl. If the radicals are substituted one or more times by a defined substitutent they are for example substituted three times, or twice or once by the corresponding substituents.

$C_2$-$C_{12}$alkenyl is mono or polyunsaturated, linear or branched and is for example $C_2$-$C_8$-, $C_2$-$C_6$- or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_5$-$C_6$cycloalkenyl has one or more double bonds and is for example cyclopentenyl or cyclohexenyl.

Halogen is fluorine, chlorine, bromine and iodine, especially fluorine, chlorine and bromine, preferably fluorine and chlorine, in particular chlorine.

$C_1$-$C_{12}$alkoxy is linear or branched and is for example $C_1$-$C_8$—, $C_1$-$C_6$- or $C_1$-$C_4$-alkoxy. Examples are methoxy, ethoxy, propoxy, isopropoxy, n-butyloxy, sec-butyloxy, isobutyloxy, tertbutyloxy, pentyloxy, hexyloxy, heptyloxy, 2,4,4-trimethylpentyloxy, 2-ethylhexyloxy, octyloxy, nonyloxy, decyloxy or dodecyloxy $C_1$-$C_8$—, $C_1$-$C_6$- and $C_1$-$C_4$-alkoxy also are linear or branched and have the same meanings as given above up to the corresponding number of C-atoms.

$C_1$-$C_{12}$alkylthio is linear or branched and is for example $C_1$-$C_{10}$-, $C_1$-$C_8$—, $C_1$-$C_6$— or $C_1$-$C_4$alkylthio. Examples are methylthio, ethylthio, propylthio, isopropylthio, n-butylthio, secbutylthio, iso-butylthio, tert-butylthio, pentylthio, hexylthio, heptylthio, 2,4,4-trimethylpentylthio, 2-ethylhexylthio, octylthio, nonylthio, decylthio or dodecylthio, in particular methylthio, ethylthio, propylthio, isopropylthio, n-butylthio, sec-butylthio, iso-butylthio, tert-butylthio, preferably methylthio.

Phenyl$C_1$-$C_3$alkyl is for example benzyl, phenylethyl, α-methylbenzyl or α,α-dimethylbenzyl, especially benzyl.

Substituted phenyl or phenyl$C_1$-$C_3$alkyl is for example substituted one to five times, e.g. once, twice or three times, in particular once or twice at the phenyl ring.

$C_6$-$C_{14}$aryl is for example phenyl, naphthyl, anthryl or phenanthryl, in particular phenyl or naphthyl, preferably phenyl.

$C_1$-$C_6$alkylene is linear or branched alkylene, e.g. $C_1$-$C_4$alkylene, for example methylene, ethylene, propylene, 1-methylethylene 1,1-dimethylethylene, butylene, 1-methylpropylene, 2-methyl-propylene, pentylene or hexylene. Linear or branched $C_1$-$C_3$alkylene has the meanings as given above up to the corresponding number of C-atoms.

Linear or branched $C_1$-$C_6$alkylene-O, linear or branched $C_1$-$C_6$alkylene-S, S—$C_1$-$C_{12}$alkylene, linear or branched $C_1$-$C_6$alkylene-(CO), linear or branched $C_1$-$C_6$alkylene-N($R_3$), linear or branched $C_1$-$C_6$alkylene-(N$R_3$)—$C_1$-$C_6$alkylene-N($R_4$), (CO)—$C_1$-$C_3$alkylene-O$R_6$, $C_2$-$C_6$alkylene which is interrupted by one or more O, (CO)O or O(CO), O—$C_2$-$C_{12}$alkylene which is interrupted by one or more O or O(CO), S—$C_2$-$C_{12}$alkylene which is interrupted by one or more O, (CO)O or O(CO), O—$C_1$-$C_6$alkylene-(CO) and S—$C_1$-$C_6$alkylene-(CO) with respect to the alkylene or interrupted alkylene are defined as given above for alkylene and interrupted alkyl up to the corresponding number of C-atoms, where naturally the interrupted alkylene comprises on more free valence than the interrupted alkyl.

Any of the above alkylene, alkylene-O, alkylene-S, alkylene-(CO), alkylene-N($R_3$), alkyleneN($R_3$)-alkylene-(N($R_4$), interrupted alkylene, interrupted Oalkylene, interrupted Salkylene which is substituted one or more times by a defined substitutent is for example substituted 1-4, 1-3, three times, twice or once by the corresponding substituent.

"Photoactive moiety" is a group which upon exposure to radiation, in particular with light of the wavelengths 150-800 nm, e.g. 200-800 nm or 200-600 nm, builds up a species which is capable to initiate a reaction, for example radicals are formed which are capable to initiate a radical polymerization reaction. Examples of photoactive moieties are the groups Q or $Q_1$ as defined above.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences referring to the compounds of the formula (1) or (1') as given hereinbefore and in the context of the whole text, are intended not to refer to the compounds as such only, but to all categories of the claims. That is to the compositions, comprising the compounds of the formula (1) or (1'), to the photoinitiator mixtures comprising said compounds, as well the use or process claims in which said compounds are employed.

The compounds of the present invention advantageously are prepared by reacting an amino-substituted polyhedral oligomeric silsesquioxane (POSS-1) with a photoacitive moiety which bears a glycidyl or epoxide end-group (P1) by means of ring-opening addition.

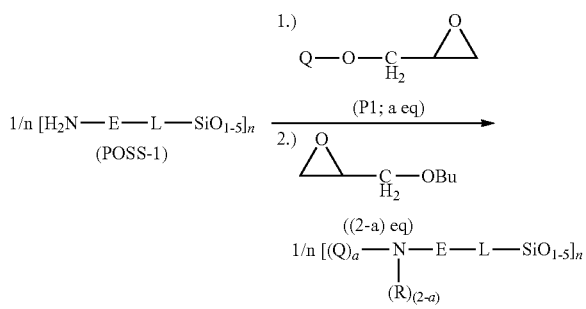

wherein Q, E, L and n are defined as above, a 5 2 and R is for example $C_4H_9O$—$CH_2$—$CH(OH)CH_2$— formed upon ring-opening addition of butyl glycidyl ether to the nitrogen atom of the amino group.

Depending on the stoichiometry, i.e. depending on the amount (a eq) of photoactive moiety (P1) and the amount ((2-a) eq or less) of butyl glycidyl ether that are reacted with the amino-substituted polyhedral oligomeric silsesquioxane (POSS-1) mixed products may be obtained characterized by the simultaneous presence of amino groups with different alkylation degrees, (including for example fully alkylated tertiary amino groups (—N(Q)$_2$, —N(Q)(R) and/or —N(R)$_2$) as well as partly alkylated secondary amino groups (—NH (Q) and/or —NH(R)) or non-alkylated primary amino groups (—NH$_2$).

Instead of a photoactive moiety Q with a glycidyl group (P1), a photoactive moiety Q with an epoxide

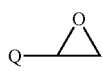
(P1a)

may also be employed in the above reaction.

Instead of a compound (P1) in the above reaction also compounds (P2)

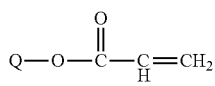
(P2)

could be employed and reacted with an amino-substituted polyhedral oligomeric silsesquioxane (POSS-1) by means of Michael addition.

Alkylation of amines, i.e. via ring-opening addition of epoxides or Michael addition of acrylates is well known and described for example in Houben-Weyl, *Methoden der Organischen Chemie*, G. Thieme Verlag, Stuttgart 1957, vol. XI/1, pp. 311 and pp. 267, respectively.

In these reactions for example a broad range of solvents is possible, e.g. non-polar, dipolar aprotic and protic solvents; preferred are protic solvents such as alcohols, in particular methanol, ethanol, n-propanol, i-propanol and the like.

Further, a broad temperature range in these reactions is possible; preferred is a temperature range between ambient temperature and the boiling point of the alcohol, e.g. between 25° C. and 100° C., preferably between 40° C. and 80° C.

Preferably the amino group used in the above reaction is completely alkylated.

Preferably the aminoalkyltrialkoxysilane is first hydrolyzed (i.e. subjected to hydrolytic polycondensation conditions) to afford a mixture of aminoalkyl-POSS which subsequently is N-alkylated.

Amine substituted silsesquioxanes (POSS-1) are for example prepared by acid or base catalyzed, or e.g. by autocatalyzed, hydrolytic polycondensation of a trialkoxy-aminoalkyl silane, for example a triethoxy-aminoalkyl silane or a trimethoxy-aminoalkyl silane, in protic solvents like alcohols (e.g. methanol, ethanol, n-propanol, i-propanol and the like) as reported by e.g. J. Rozière et al., *Chemistry of Materials*, 1996, 8, 1758-1769 (CAN 125: 130645) according to:

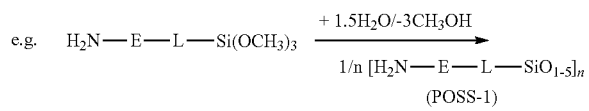

wherein E and n are defined as above. Optionally, methanol or an excess of water (e.g. if >1.5 eq $H_2O$ were used) are removed by distillation in order to drive polycondensation to completion. The preparation of POSS in general is known to the person skilled in the art and for example described by M. Voronkov et al., *Topics in Current Chemistry* 1982, 102, 199-236 (CAN 97:103150).

Photoactive moieties with glycidyl or epoxide groups (P1) are for example obtained by reacting a corresponding hydroxyl-substituted compound with glycidyl chloride. Such preparation methods are familiar to the person skilled in the art and described in the usual textbooks of chemistry such as e.g. Houben-Weyl, *Methoden der Organischen Chemie*, G. Thieme Verlag, Stuttgart 1965, vol. VI/3, pp. 421.

Other methods to prepare the compounds of the formula (1) would for example include reacting an epoxide- or glycidyl-substituted silsesquisiloxane (POSS-2) with a corresponding amine-substituted photoactive moiety (P3) by means of ring-opening addition, or reacting an acrylate-substituted silsesquisiloxane (POSS-3) with a corresponding amine-substituted photoactive moiety (P3) by means of Michael addition:

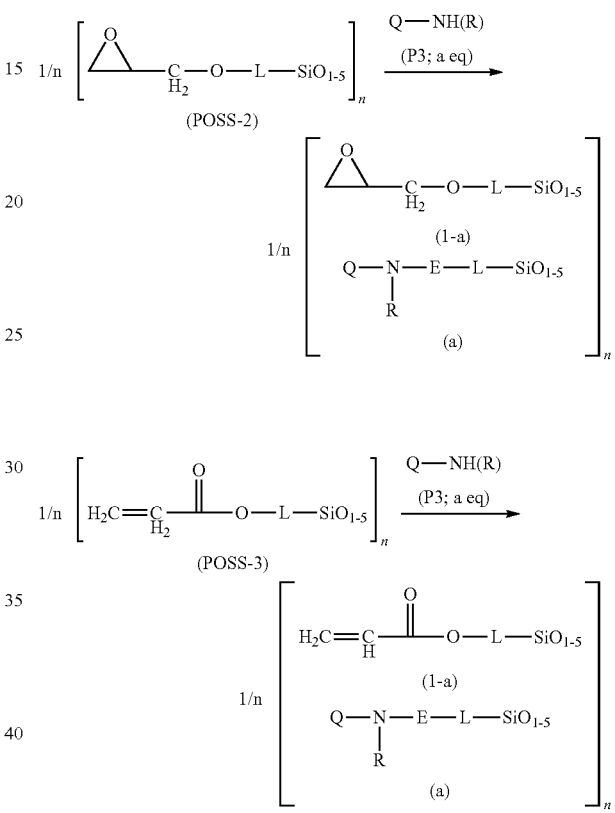

wherein the definitions of Q, E, L, n and R are as given above and a≤1.

Still other methods to prepare the compounds of the formula (1) would for example include reacting an epoxide-substituted silsesquisiloxane (POSS-2) with a corresponding hydroxysustituted photoactive moiety (P4) and a secondary amine by means of ring-opening addition, or co-hydrolysing a trialkoxysilylated photoactive moiety (P5) together with a trialkoxy-aminoalkyl silane:

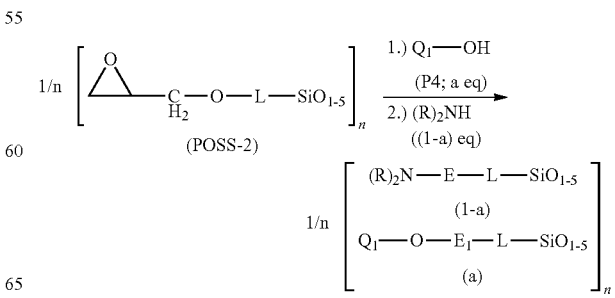

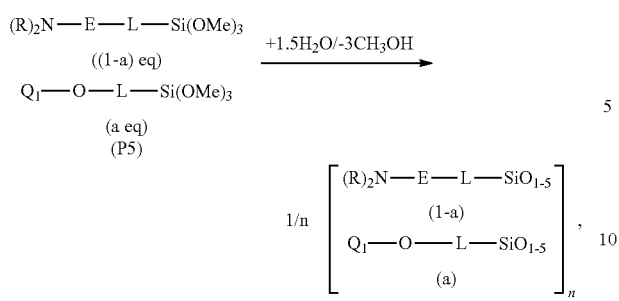

$$\frac{1}{n}\begin{bmatrix} (R)_2N-E-L-SiO_{1.5} \\ (1-a) \\ Q_1-O-L-SiO_{1.5} \\ (a) \end{bmatrix}_n,$$

wherein the definitions of Q, $Q_1$, E, L, n and R are as given above and a≤1.

With the processes as described above generally mixtures of compounds of the formula (1) with different n are obtained. That is, a mixture of compounds with different molecular weight (MW) is obtained in a distribution of the compounds with different n, wherein the peak of the distribution is at n=8.

The molecular weight of the compounds of the present invention for example ranges from 1'000-10'000.

Further different grades of condensation can be formed, i.e. not all positions at the Si-atom are reacted with a group comprising the photoactive moiety or amine functionality. The index of poyldispersity (PDI, determined by Gel Permeation Chromatography [GPC] analysis) for example is in the range of 1.1<PDI<1.5, preferably 1.2<PDI<1.4.

The amount of photoactive moiety in the presently claimed compounds preferably is high, e.g. higher than 35% wt, preferably higher than 40% wt.

Typically the particle size of the reaction product of the above described processes as determined by dynamic light scattering (DLS) and atomic force microscopy (AFM) is <25 nm, preferably <10 nm.

If necessary the compounds can be isolated by methods known to the person skilled in the art, e.g. distillation, chromatography etc.

However, in the context of the present invention isolation of a single component of the prepared mixture is not necessary by all means, as the mixtures according to the present invention can be used as such, as they exhibit excellent photoinitiator properties. They provide a reactive system with high molecular weight, thus fulfilling the need of low migration from the cured formulation.

The present invention in particular describes mixtures of polyhedral oligomeric silsesquioxanes containing fully condensed cage-type frameworks $[ASiO_{1.5}]_n$ with different size (e.g. n=6, 8, 10, 12; structures I-IV) to which photoactive moieties together with amine-type coinitiators/synergists are bonded:

Compounds of the Formula (1)—$[ASiO_{1.5}]_n$:

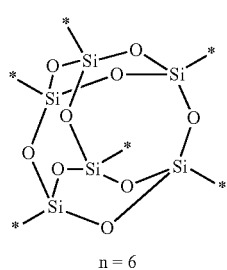

n = 6

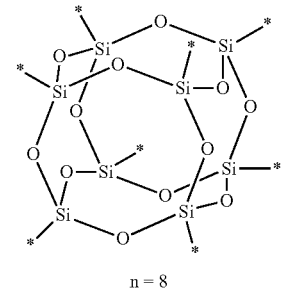

n = 8

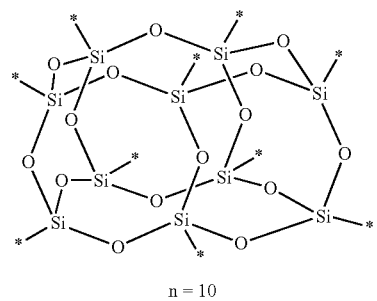

n = 10

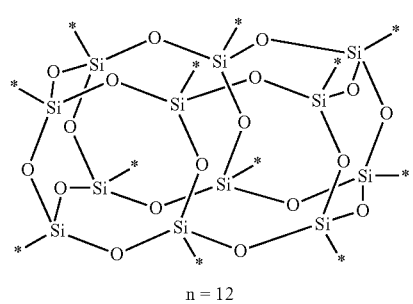

n = 12

These mixtures are obtained by hydrolysis/condensation of a suitably functionalized trialkoxysilane followed by grafting of the photoinitiators, or, by first grafting the photoinitiators to a suitably functionalized (non-hydrolyzed) trialkoxysilane followed by hydrolysis/condensation according to methods described by e.g. J. Roziere et al., *Chemistry of Materials*, 1996, 8, 1758-1769 (CAN 125: 130645) or M. Voronkov et al., *Topics in Current Chemistry* 1982, 102, 199-236 (CAN 97:103150).

As a suitably functionalized trialkoxysilane for example aminopropyl-trimethoxy silane can be used.

The term "mixture" in the context of the present invention also encompasses byproducts formed during hydrolysis of trialkoxysilanes that are incompletely condensed. Conventionally, the Tn notation, where T represents a silicon atom and n the number of bridging oxygen atoms (i.e. oxygen atoms that are bonded to another silicon atom), is used to describe the condensation degree as for example published by C. Croutxe-Barghorn et al., *RadTech Europe* 05 [Conference Proceedings] 2005, 2, 305-309 (CAN 145:507142). According to this notation, T0 represents non-condensed (monomeric), T1 simply-condensed, T2 doublycondensed and T3 triply-condensed (completely or fully condensed) sites. Usually the condensation degree is determined by $^{29}$Si-NMR, as the chemical shift of the silicon atom is high-field shifted by 8 to 9 ppm for each condensation step. In the case of trifunctional alkoxysilanes, the $^{29}$Si chemical shifts range from ca. −35 ppm (T0; 3-aminopropyltrimethoxysilane:

ca. −42 ppm) to ca. −75 ppm (T3; 3-aminopropyltrimethoxysilane: ca. −66--69 ppm) according to

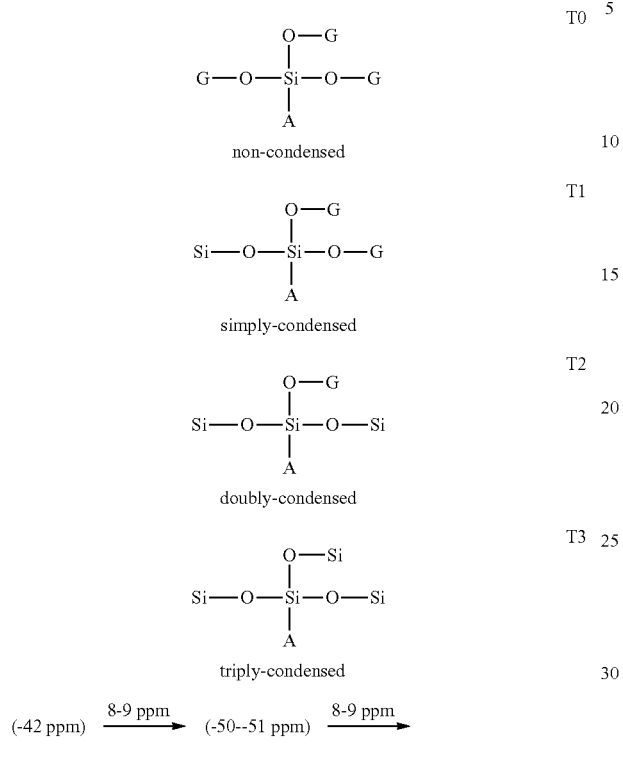

where G is hydrogen or alkyl.

Thus, the term "mixture" in the context of the present invention encompasses, in addition to completely condensed T3-species of formula (1), also incompletely condensed side products or precursors of formula (1')—[(ASiO$_{1.5}$)$_{n'}$(A(R$_{24}$O)SiO$_{1.0}$)$_a$]— that are characterized by the presence of T2 domains. Incompletely condensed T3-species containing T2-sites are for example structures V-XVIII and isomers.

Compounds of formula (1')—[(ASiO$_{1.5}$)$_{n'}$(A(R$_{24}$O)SiO$_{1.0}$)$_a$]— wherein R$_{24}$ is H, n' is 4, 6, 8 and 10, a is 2 and the sum of n'+a is 6, 8, 10 and 12 (designated compounds of formula (W1)):

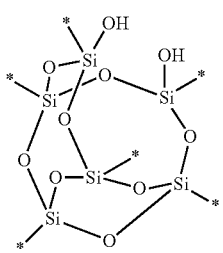

(V)

n' = 4, a = 2,
n' + a = 6

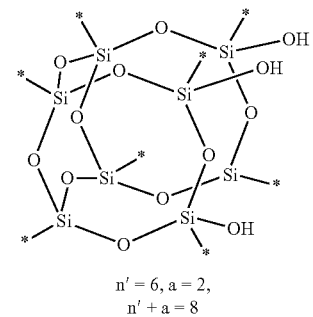

(VI)

n' = 6, a = 2,
n' + a = 8

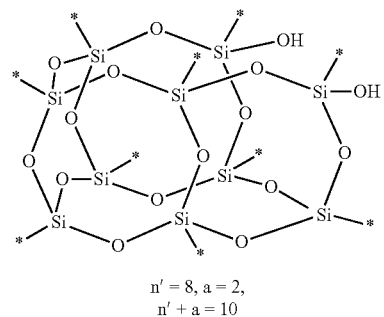

(VII)

n' = 8, a = 2,
n' + a = 10

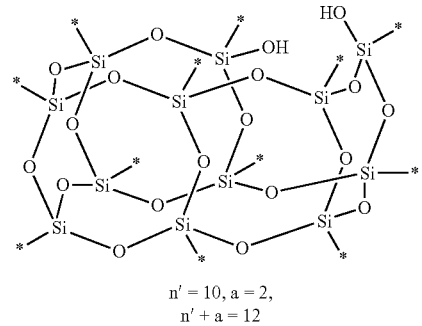

(VIII)

n' = 10, a = 2,
n' + a = 12

Compounds of formula (1')—[(ASiO$_{1.5}$)$_{n'}$(A(R$_{24}$O)SiO$_{1.0}$)$_a$]— wherein R$_{24}$ is H, n' is 2, 4, 6 and 8, a is 4 and the sum of n'+a is 6, 8, 10 and 12 (designated compounds of formula (W2)):

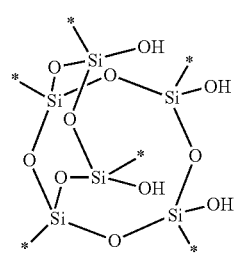

(IX)

n' = 2, a = 4,
n' + a = 6

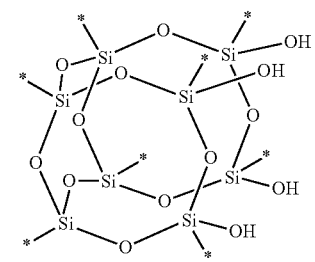

(X)

n' = 4, a = 4,
n' + a = 8

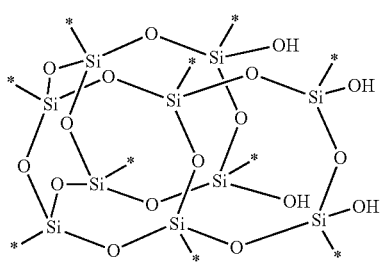

(XI)

n' = 6, a = 4,
n' + a = 10

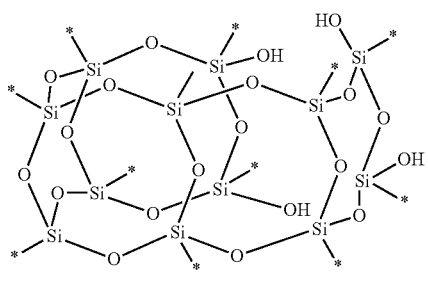

(XII)

n' = 8, a = 4,
n' + a = 12

Compounds of formula (1')—[(ASiO$_{1.5}$)$_{n'}$(A(R$_{24}$O)SiO$_{1.0}$)$_a$]—wherein R$_{24}$ is H, n' is 6, 8 and 10, a is 1 and the sum of n'+a is 7, 9 and 11 (designated compounds of formula (W3)):

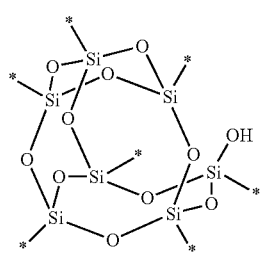

(XIII)

n' = 6, a = 1,
n' + a = 7

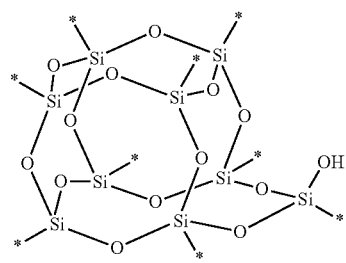

(XIV)

n' = 8, a = 1,
n' + a = 9

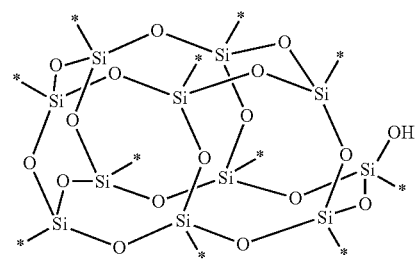

(XV)

n' = 10, a = 1,
n' + a = 11

Compounds of formula (1')—[(ASiO$_{1.5}$)$_{n'}$(A(R$_{24}$O)SiO$_{1.0}$)$_a$]—wherein R$_{24}$ is H, n' is 4, 6 and 8, a is 3 and the sum of n'+a is 7, 9 and 11 (designated compounds of formula (W4)):

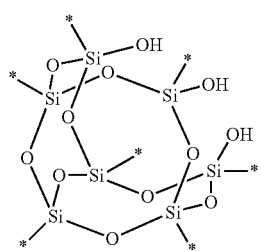

(XVI)

n' = 4, a = 3,
n' + a = 7

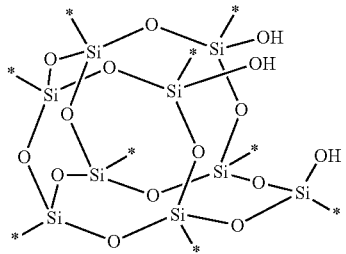

(XVII)

n' = 6, a = 3,
n' + a = 9

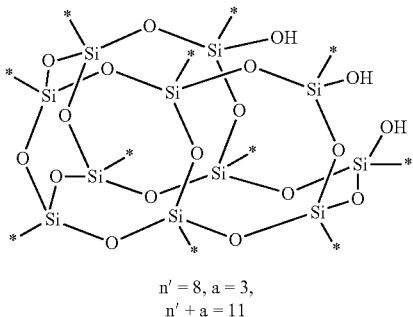

(XVIII)

n' = 8, a = 3,
n' + a = 11

In the structures (V)-(XVIII) the asterix * denote the position of different groups A as defined above.

As described above, due to the preparation process compound mixtures are obtained. Said mixtures as such can be used as photoinitiator, without isolation of a single component.

Subject of the invention therefore is a mixture of photoinitiator compounds of the formula (1) or (1') as defined above.

Further subject of the invention is a mixture as defined above, wherein
 (i) compounds of the formula (1) are present wherein n is 6 and
 (ii) compounds of the formula (1) are present wherein n is 8 and
 (iii) compounds of the formula (1) are present wherein n is 10 and
 (iv) compounds of the formula (1) are present wherein n is 12.

Another subject of the invention is a mixture of photoinitiator compounds of the formula (1) as defined above with
 compounds of the formula (1') selected from the group consisting of compounds of formula (W1), (W2), (W3) and (W4), wherein
 (W1) the sum of n' and a is an integer 6, 8, 10 or 12;
  n' is an integer 4, 6, 8 or 10; and
  a is 2;
 (W2) the sum of n' and a is an integer 6, 8, 10 or 12;
  n' is an integer 2, 4, 6 or 8; and
  a is 4;
 (W3) the sum of n' and a is an integer 7, 9 or 11;
  n' is an integer 6, 8 or 10; and
  a is 1;
 (W4) the sum of n' and a is an integer 7, 9 or 11;
  n' is an integer 4, 6 or 8; and
  a is 3.

Interesting further are mixtures of one or more different compounds of the formula (1), e.g. such with different definitions of n, with one or more different compounds of the formula (11)

$$[C_1\text{-}C_4\text{-alkyl-SiO}_{1.5}]_n \qquad (11)$$

wherein the $C_1$-$C_4$-alkyl preferably is isobutyl and n is defined as for formula (1).

In the context of the present invention it is also possible to use mixtures as defined above which additionally comprise linear or branched siloxane compounds, which siloxanes for example also comprise photoinitiator moieties as described above.

E as linear or branched $C_1$-$C_6$alkylene(CO)O is for example —$CH_2CH_2$—(CO)O—, E as linear or branched $C_2$-$C_6$alkyleneN($R_3$) is for example —$CH_2CH_2$—N($R_3$)—, E as linear or branched $C_1$-$C_6$alkylene(N$R_3$)$C_1$-$C_6$alkyleneN($R_4$) is for example —$CH_2CH_2$—N($R_3$)—$CH_2CH_2$—N($R_4$)—.

E in particular is a direct bond or $C_2$-$C_6$alkyleneN($R_3$).

Different A in the formula A must not by all means have the same meaning, that is, different A in the formula may have different meanings in the defined scope. For example, in case that n is 8, one A is $C_1$-$C_{12}$alkyl, while 7 A are a group of the formula (2); or 2 A are $C_1$-$C_{12}$alkyl, while 6 A are a group of the formula (2); or for example in case that n is 6, one A is $C_1$-$C_{12}$alkyl, while 5 A are a group of the formula (2), etc.

A in particular is $C_1$-$C_{12}$alkyl or a group of formula (2).

A as linear or branched $C_1$-$C_{12}$alkyl is preferably ethyl, isobutyl or isooctyl.

L as linear or branched $C_1$-$C_3$alkylene preferably is propylene.

In case that L is $C_2$-$C_3$alkylene which is substituted by OR$_6$, E preferably is a direct bond.

In case that L is linked to E1 or E2, L preferably is not is $C_2$-$C_3$alkylene which is substituted by OR$_6$.

$R_1$ and $R_2$ for example are identical or different, that is they for example independently of one another denote a photoactive moiety, linear or branched $C_2$-$C_{20}$alkyl, e.g. heptylene, which is interrupted by one or more O and which is substituted by OR$_6$, In case, that both $R_1$ and $R_2$, denote Q, said Q has not by all means to be of the same definition, e.g. $R_1$ as Q for example is a group of formula (3), while in the same molecule $R_2$ as Q for example denotes a group of the formula (4).

$Z_1$-$Z_4$ as O$C_1$-$C_6$alkylene which is unsubstituted or substituted by one or more OR$_6$ are for example-O—$CH_2CH$(OH)$CH_2$—; as O$C_2$-$C_{12}$alkylene which is interrupted by one or more O or O(CO) and which is unsubstituted or substituted by one or more OR$_6$ are for example O—$CH_2CH$(OH)$CH_2$—, -O—$CH_2CH_2$—O—$CH_2CH$(OH)$CH_2$—, -O—$CH_2C$(CO)—O—$CH_2CH$(OH)$CH_2$—, ($C_1$-$C_6$alkylene)-O—$CH_2CH$(OH)$CH_2$—, -O—$CH_2CH_2$—O—C(O)$CH_2CH_2$—; as S$C_1$-$C_{12}$alkylene which is unsubstituted or substituted by one or more OR$_6$ are for example -S—$CH_2CH$(OH)$CH_2$—; as S$C_1$-$C_{12}$alkylene which is interrupted by one or more O or O(CO) are for example -S—$CH_2CH_2$—O—$CH_2CH_2CH_2$—, -S—$CH_2C$(CO)—O—$CH_2CH_2CH_2$—, -S—$CH_2CH_2$—O—C(O)$CH_2CH_2$—; as O—$C_1$-$C_6$alkylene-(CO) or S—$C_1$-$C_6$alkylene-(CO) are for example -O—$CH_2C$(O)—, **-S—$CH_2C$(O)—; in which definitions the double asterisk denotes the bonding to the phenyl ring.

$Z_1$-$Z_4$ for example are O$C_2$-$C_{12}$alkylene, e.g. Opropylene, Obutylene or Opentylene, which is interrupted by (CO)O or O and which optionally is substituted by one or more OR$_6$; or are O$C_1$-$C_6$alkylene which is substituted by one or more OR$_6$.

Q is for example a group of formula (3) or (4), in which formula (3) p for example is O, $R_8$ and $R_9$ and $R_{10}$ are $C_1$-$C_4$alkyl, in particular methyl, and X is OR$_6$; and in which formula (4) for example $R_{12}$, $R_{13}$ and $R_{14}$ are hydrogen.

$Q_1$ is for example a group of formula (8) or (9), in which formula (8) p for example is O, $R_8$ and $R_9$ and $R_{10}$ are $C_1$-$C_4$alkyl, in particular methyl, and X is OR$_6$; and in which formula (9) for example $R_{12}$, $R_{13}$ and $R_{14}$ are hydrogen.

X is OR$_5$ or NR$_7$R$_8$, in particular OR$_6$. Preferably in the group OR$_5$, $R_5$ is hydrogen.

In the group $NR_7R_8$, $R_7$ and $R_8$ preferably are methyl or together with the N-atom to which they are bonded are morpholino (

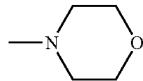

)

Preferred are compounds of the formula (1) wherein, if one of $R_1$ or $R_2$ is Q and $Z_1$ or $Z_2$ or $Z_3$ is (CO), O—$C_1$-$C_6$alkylene-(CO) or S—$C_1$-$C_6$alkylene-(CO), then the other $R_2$ or $R_1$ is not $(CO)R_{15}$, $(CO)N(R_{16})_2$, $R_{16}(SO_2)$, $(CO)OR_{16}$, $P(O)(OR_{16})_2$ or $(CO)C_1$-$C_3$alkylene-$OR_{25}$.

Preferred are compounds of the formula (1) wherein, if $R_1$ and $R_2$ together are

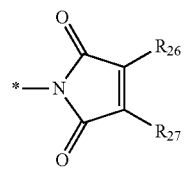

or if $R_{15}$ is

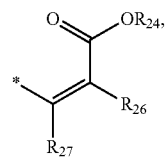

or if A is glycidyl-O-L-, $CH_2=C(R_5)$—(CO)O-L- or

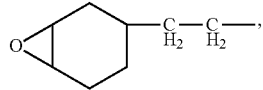

then the remaining $R_1$ and $R_2$, $R_{11}$ and $R_{29}$ are not hydrogen.

Preferred are compounds of the formula (1) wherein, if one of $R_1$ or $R_2$ is Q and $Z_1$ or $Z_2$ or $Z_3$ or $Z_4$ is (CO), O—$C_1$-$C_6$alkylene-(CO) or S—$C_1$-$C_6$alkylene-(CO), or $Z_5$ is a direct bond, then the other $R_2$ or $R_1$ is not $(CO)R_{15}$, $(CO)N(R_{16})_2$, $R_{16}(SO_2)$, $(CO)OR_{16}$, $P(O)(OR_{16})_2$ or $(CO)C_1$-$C_3$alkylene-$OR_{25}$ and if $R_1$ and $R_2$ together are

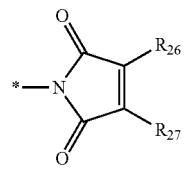

or if $R_{15}$ is

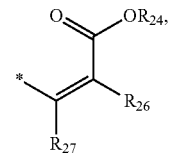

or if A is glycidyl-O-L-, $CH_2=C(R_5)$—(CO)O-L- or

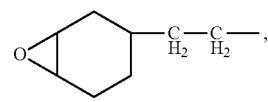

then the remaining $R_1$ and $R_2$, $R_{11}$ and $R_{29}$ are not hydrogen.

Further preferred are compounds of the formula (1), wherein $R_1$ and $R_2$ not simultaneously are a group Q wherein $Z_1$, $Z_2$, $Z_3$ or $Z_4$ are O—$C_1$-$C_6$alkylene(CO) or S—$C_1$-$C_6$alkylene-(CO) and wherein $R_3$ and $R_4$ not simultaneously are a group Q wherein $Z_1$, $Z_2$, $Z_3$ or $Z_4$ are O—$C_1$-$C_6$alkylene(CO) or S—$C_1$-$C_6$alkylene-(CO).

Interesting is a photoinitiator compound as defined above of the formula (1), wherein n is 2m;

m is an integer of 3 to 6;

different A independently of each other are linear or branched $C_1$-$C_{12}$alkyl, glycidyl-O-L-, $CH_2=C(R_5)$—(CO)O-L-, or a photoactive moiety Q1, or different A independently of each other are a group of formula (2)

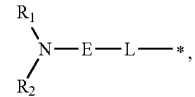

(2)

wherein the asterisk * denotes the bond to the silicon;

E is a direct bond, linear or branched $C_2$-$C_6$alkylene-O which is unsubstituted or substituted by one or more $OR_6$, or E is linear or branched $C_1$-$C_6$alkylene(CO)O, or E is linear or branched $C_2$-$C_6$alkyleneN($R_3$) or linear or branched $C_2$-$C_6$alkylene($NR_3$)$C_2$-$C_6$alkyleneN($R_4$);

L is linear or branched $C_1$-$C_4$alkylene, preferably propylene;

$R_1$ and $R_2$ independently of each other are a photoactive moiety Q, hydrogen, or $R_1$ and $R_2$ are linear or branched $C_1$-$C_6$alkyl which is unsubstituted or substituted by one or more $OR_6$, $NR_7R_8$ or by $(CO)OR_{24}$;

or $R_1$ and $R_2$ independently of each other are linear or branched $C_2$-$C_{26}$alkyl which is interrupted by one or more O or (CO)O and which interrupted $C_2$-$C_{26}$alkyl is unsubstituted or substituted by one or more $OR_6$, $NR_7R_8$ or by $C(R_{24})=C(R'_{24})_2$; or $R_1$ and $R_2$ independently of each other are $(CO)R_{15}$;

$R_3$ and $R_4$ independently of each other are a photoactive moiety Q, hydrogen, linear or branched $C_1$-$C_6$alkyl which is unsubstituted or substituted by one or more $OR_6$;

or $R_3$ and $R_4$ independently of each other are linear or branched $C_2$-$C_{26}$alkyl which is interrupted by one or more O, and which interrupted $C_2$-$C_{26}$alkyl is unsubstituted or substituted by one or more $OR_6$;

$R_5$ is hydrogen;
$R_6$ is hydrogen, $C_1$-$C_4$alkyl or $(CO)R_{15}$;
$R_7$ and $R_8$ independently of each other are linear or branched $C_1$-$C_6$alkyl, or $R_7$ and $R_8$ together with the nitrogen atom to which they are bonded form a group

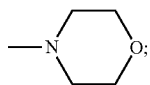

Q is a group of formula (3), (4) or (7);
Q1 is a group of formula (9), (10) or (11);
p is 0;
$Z_1$, and $Z_2$ independently of each other are **$OC_1$-$C_6$alkylene which is unsubstituted or substituted by one or more $OR_6$,
or independently of each other are **$OC_2$-$C_{12}$alkylene which is interrupted by one or more O or O(CO) and which is unsubstituted or substituted by one or more $OR_6$;
$Z_5$ is linear or branched O—$C_2$-$C_8$alkylene interrupted by one or more O;
$Z_7$, $Z_8$ and $Z_9$ independently of each other are **-O-E1-L-;
E1 is

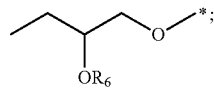

X is $OR_5$;
$R_9$ and $R_{10}$ independently of each other are $C_1$-$C_6$alkyl;
$R_{12}$, $R_{13}$ and $R_{14}$ independently of each other are hydrogen or halogen;
$R_{15}$ is linear or branched $C_1$-$C_{20}$alkyl or is phenyl which is unsubstituted or is substituted by one or more $N(R_7)(R_8)$; and
$R_{24}$ and $R'_{24}$ are hydrogen.
Preferred is a photoinitiator compound as defined above, of the formula (1), wherein
n is 2m;
m is an integer of 3 to 6;
different A independently of each other are linear or branched $C_1$-$C_{12}$alkyl, or different A independently of each other are a group of formula (2)

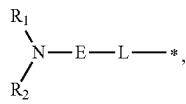

(2)

wherein the asterisk * denotes the bond to the silicon;
E is a direct bond or branched $C_2$-$C_6$alkyleneN($R_3$);
L is propylene;
$R_1$ and $R_2$ independently of each other are a photoactive moiety Q,
or $R_1$ and $R_2$ independently of each other are linear or branched $C_2$-$C_{20}$alkyl which is interrupted by one or more O, and which interrupted $C_2$-$C_{20}$alkyl is unsubstituted or substituted by one or more $OR_6$;
$R_3$ is a photoactive moiety Q,
$R_5$ is hydrogen;
$R_6$ is hydrogen;
Q is a group of formula (3) or (4);
p is 0;
$Z_1$, and $Z_2$ independently of each other are **$OC_1$-$C_6$alkylene which is unsubstituted or substituted by one or more $OR_6$,
or independently of each other are **$OC_2$-$C_{12}$alkylene which is interrupted by one or more O or O(CO) and which is unsubstituted or substituted by one or more $OR_6$;
X is $OR_5$;
$R_9$ and $R_{10}$ are $C_1$-$C_6$alkyl, in particular methyl; and
$R_{12}$, $R_{13}$ and $R_{14}$ are hydrogen.

In accordance with the invention, the compounds of the formula (1) or mixtures as described above comprising said compounds can be used as photoinitiators for the photopolymerization of ethylenically unsaturated compounds.

The invention therefore also relates to photopolymerizable compositions comprising
(A) at least one ethylenically unsaturated photopolymerizable compound and
(B) at least one photoinitiator or photoinitiator mixture as defined above, in particular at least one photoinitiator of the formula (1) as defined above.

The composition may comprise additionally to the component (B) at least one further photoinitiator (C), and/or further coinitiators (D) and/or other additives.

The unsaturated compounds may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Interesting also are resins which are modified with silicon or fluor, e.g. silicon acrylates. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol tri-acrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, acrylated polyesters, polyesters containing vinyl ether or epoxy groups, and also acrylated polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the abovementioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof. Also suitable as components (A) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols. Polybutadiene and polyisoprene and copolymers thereof are known. Examples of suitable comonomers are olefins, such as ethylene, propene, butene and hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Binders as well can be added to these novel compositions, and this is particularly expedient when the photopolymerizable compounds are liquid or viscous substances. The quantity of binder may, for example, be 5-95%, preferably 10-90% and especially 40-90%, by weight relative to the overall solids content. The choice of binder is made depending on the field of application and on properties required for this field, such as the capacity for development in aqueous and organic solvent systems, adhesion to substrates and sensitivity to oxygen.

Examples of binders with high molecular weight (oligomeric) polyunsaturated compounds are acrylate epoxy resins, acrylate or vinyl-ether- or epoxy-group-containing polyesters, polyurethanes and polyethers.

Examples of suitable binders are polymers having a molecular weight of about 1000 to 2000000, preferably 10000 to 1000000. Examples are: homo- and copolymers of acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of ylnylidene chloride with acrylonitrile, methyl methacrylate and vinyl acetate, polyvinyl acetate, copoly(ethylene/vinyl acetate), polymers such as polycaprolactam and poly(hexamethyleneadipamide), and polyesters such as poly(ethylene glycol terephtalate) and poly (hexamethylene glycol succinate) and polyimides.

Suitable binders can also be a powder.

The unsaturated compounds can also be used as a mixture with non-photopolymerizable, film-forming components.

These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal aftertreatment.

The binder can simultaneously bear the radically photopolymerizable and the chemically or thermally curable function, providing a so-called dual-cure binder.

In addition to the photoinitiator the photopolymerizable mixtures may include various additives (D). Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilisers are disclosed in WO 04/074328, page 12, line 9 to page 14, line 23, said disclosure hereby is incorporated by reference.

Further additives known in the art may be added, as for example antistatics, flow improvers and adhesion promoters.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

It is further possible to add chain transfer agents which are customary in the art to the compositions according to the invention. Examples are mercaptanes, amines and benzothiazol. Photopolymerization can also be accelerated by adding further photosentisizers which shift or broaden the spectral sensitivity. These are, in particular, aromatic carbonyl compounds, for example benzophenone, thioxanthone, anthraquinone and 3-acylcoumarin derivatives, and also 3-(aroylmethylene)thiazolines, camphor quinone, but also eosine, rhodamine and erythrosine dyes, as well as all compounds which can be used as coinitiators as described above.

Examples of suitable sensitizer compounds (D) are disclosed in WO 06/008251, page 36, line 30 to page 38, line 8, the disclosure of which is hereby incorporated by reference.

The curing process can be assisted by adding a component which under thermal conditions forms free radicals, for example an azo compound such as 2,2'-azobis(4-methoxy-2, 4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (D) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiction. Similar compositions are for example described in EP 445624.

Further customary additives, depending on the intended use, are optical brighteners, fillers, pigments, dyes, wetting agents or levelling assistants.

In order to cure thick and pigmented coatings it is appropriate to add glass microspheres or pulverized glass fibres, as described for example in U.S. Pat. No. 5,013,768.

The compositions may also comprise dyes and/or white and colored pigments. Depending on the kind of application organic as well as anorganic pigments are used. Such additives are known to the person skilled in the art, some examples are titan dioxide pigments, e.g. of the rutile type or anatas type, carbon black Russ, zinc oxide, such as zink white, iron oxide, such as iron oxide yellow, iron oxide red, chromium yellow, chromium green, nickel titanium yellow, ultramarine blue, cobalt blue, bismuth vanadate, cadmiumyellow or cadmium red. Examples of organic pigments are mono- or bisazo pigments, as well as metal complexes thereof, phthalocyanine pigments, polycyclic pigments, such as perylene-, anthraquinone-, thioindigo-, chinacridone- or triphenylmethane pigments, as well as diketo-pyrrolo-pyrole-, isoindolinone-, e.g. tetrachlorisoindolinone-, isoindoline-, dioxazin-, benzimidazolone- and chinophthalone pigments.

The pigments are employed alone or in combination in the compositions according to the invention.

Depending on the intended use the pigments are used in amount customary in the art, for example in an amount of 1-60% by weight, or 10-30% by weight, based on the whole formulation.

The compositions may also comprise organic dyes of different classes. Examples are azo dyes, methin dyes, anthraquinone dyes or metal complex dyes. Customary concentrations are for example 0.1-20%, in particular 1-5%, based on the whole formulation.

The choice of additive is made depending on the field of application and on properties required for this field. The additives described above are customary in the art and accordingly are added in amounts which are usual in the respective application.

The invention also provides compositions comprising as component (A) at least one ethylenically unsaturated photopolymerizable compound which contains some solvent, is emulsified, dispersed or dissolved in water. Many variants of such radiation-curable aqueous prepolymer dispersions are commercially available.

A prepolymer dispersion is understood as being a dispersion of water and at least one prepolymer dispersed therein. The amount of radiation curable prepolymer or prepolymer mixture, dispersed in the water for example ranges from 20 to 95% by weight, in particular from 30 to 70% by weight. In these compositions the sum of the percentages given for water and prepolymer is in each case 100, with auxiliaries and additives (e.g. emulsifiers) being added in varying quantities depending on the intended use.

The radiation-curable aqueous prepolymer dispersions are known polymeric systems, comprising mono- or polyfunctional ethylenically unsaturated prepolymers, that have an average molecular weight $M_n$ (in g/mol) of at least 400, in particular from 500 to 100'000. Prepolymers with higher molecular weights, however, may also be considered depending on the intended application. Use is made, for example, of polyesters having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight $M_n$ (in g/mol) of at least 600, additionally comprising polymerizable C—C double bonds. Other suitable aqueous dispersions, based on specific alkyl (meth)acrylate polymers, are described in EP 41125.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel photoinitiators. It is of course also possible to use mixtures with known photoinitiators (C), for example mixtures with camphor quinone; benzophenone, benzophenone derivatives, such as 2,4,6-trimethylbenzophenone, 2-methylbenzophenone, 3-methylbenzophenone, 4-methylbenzophenone, 2-methoxycarbonylbenzophenone 4,4'-bis(chloromethyl)benzophenone, 4-chlorobenzophenone, 4-phenylbenzophenone, 3,3'-dimethyl-4-methoxy-benzophenone, [4-(4-methylphenylthio)phenyl]-phenyl-methanone, methyl-2-benzoylbenzoate, 3-methyl-4'-phenylbenzophenone, 2,4,6-trimethyl-4'-phenylbenzophenone, 4,4'-bis(dimethylamino)-benzophenone, 4,4'-bis(diethylamino)benzophenone,

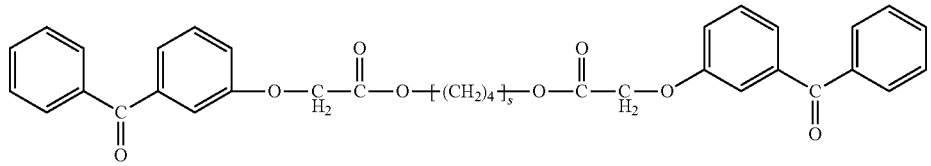

with s=1-20 (Omnipol BP), a mixture of

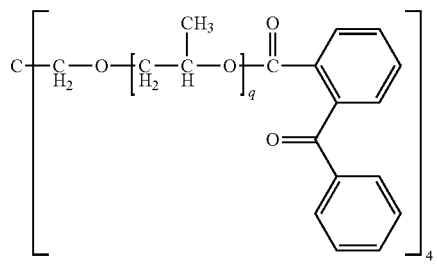

with q=about 2 and

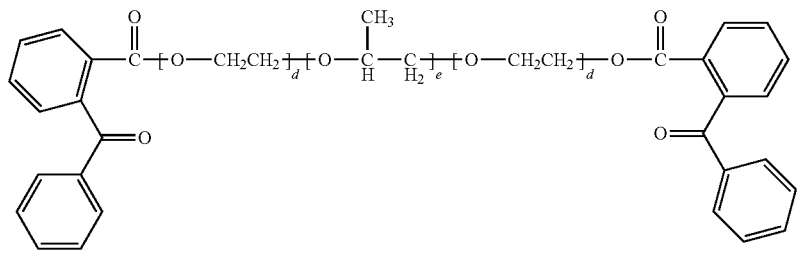

wherein the sum of d and e is about 14,

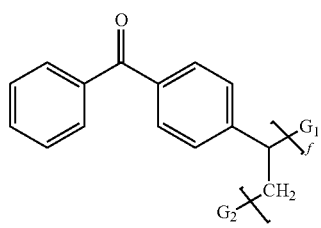

where d is greater than e (Speedcure 7005, provided by Lambson), with f=about 14 (Speedcure 7006, provided by Lambson);

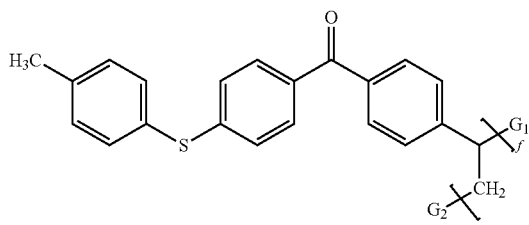

with g=about 12 (Speedcure 7003, provided by Lambson);

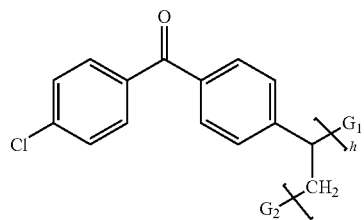

with h=about 13 (Speedcure 7020, provided by Lambson), and any blends or admixtures of the above mentioned compounds; thioxanthones, thioxanthone derivatives, polymeric thioxanthones as for example OMNIPOL TX; ketal compounds, as for example benzildimethylketal (IRGACURE® 651); acetophenone, acetophenone derivatives, for example α-hydroxycycloalkyl phenyl ketones or α-hydroxyalkyl phenyl ketones, such as for example 2-hydroxy-2-methyl-1-phenyl-propanone (DAROCUR® 1173), 1-hydroxy-cyclohexyl-phenyl-ketone (IRGACURE®184), 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one (IRGACURE®2959); 2-hydroxy-1-{4-[4-(2-hydroxy-2-methyl-propionyl)-benzyl]-phenyl}-2-methyl-propan-1-one (IRGACURE®127); 2-hydroxy-1-{4-[4-(2-hydroxy-2-methyl-propionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholinoethane (IRGACURE® 907), (4-morpholinobenzoyl)-1-benzyl-1-dimethylaminopropane (IRGACURE® 369), (4-morpholinobenzoyl)-1-(4-methylbenzyl)-1-dimethylaminopropane (IRGACURE® 379), (4-(2-hydroxyethyl)aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl aoxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)propoxy]-ethyl ester (IRGACURE® 754); ketosulfones, e.g. ESACURE KIP 1001 M; oximeesters, e.g. 1,2-octanedione 1-[4-(phenylthio)phenyl]-2-(O-benzoyloxime) (IRGACURE® OXE01), ethanone 1[9-ethyl-6-(2-methyl-benzoyl)-9H-carbazol-3-yl]-1-(O-acetyloxime) (IRGACURE® OXE02), 9H-thioxanthene-2-carboxaldehyde 9-oxo-2-(O-acetyloxime), peresters, e.g. benzophenone tetracarboxylic peresters as described for example in EP 126541, monoacyl phosphine oxides, e.g. (2,4,6-trimethylbenzoyl)diphenylphosphine oxide (DAROCUR® TPO), ethyl (2,4,6 trimethylbenzoyl phenyl) phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide (IRGACURE® 819), bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxyphenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole /co-initiators systems, e.g. ortho-chlorohexaphenyl-bisimidazole combined with 2-mercaptobenzthiazole, ferrocenium compounds, or titanocenes, e.g. bis(cyclopentadienyl)bis(2,6-difluoro-3-pyrryl-phenyptitanium (IRGACURE0784). Further, borate compounds can be used as coinitiators. As additional photoinitiators oligomeric compounds such as for example oligomeric alpha hydroxyl ketones e.g. 2-hydroxy-1-{1-[4-(2-hydroxy-2-methylpropionyl)-phenyl]-1,3,3-trimethyl-indan-5-yl}-2-methyl-propan-1-one, ESACURE KIP provided by Fratelli Lamberti, or oligomeric alpha amino ketones may be employed as well.

Where the novel photoinitiator systems are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17-25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-iso-propylbenzene)($\eta^5$-cyclopentadienyl)iron(II) hexafluorophosphate or oxime sulfonates.

Suitable sulfonium salts are obtainable, for example, under the trade names ®Cyracure UVI-6990,®Cyracure UVI-6974 (Union Carbide),®Degacure KI 85 (Degussa), SP-55, SP-150, SP-170 (Asahi Denka), GE UVE 1014 (General Electric), SarCat®KI-85 (=triarylsulfonium hexafluorophosphate; Sartomer), SarCat® CD 1010 (=mixed triarylsulfonium hexafluoroantimonate; Sartomer); SarCat® CD 1011 (=mixed triarylsulfonium hexafluorophosphate; Sartomer).

Suitable iodonium salts are e.g. tolylcumyliodonium tetrakis(pentafluorophenyl)borate, 4-[(2-hydroxy-tetradecyloxy)phenyl]phenyliodonium hexafluoroantimonate or hexafluorophosphate (SarCat® CD 1012; Sartomer), tolylcumyliodonium hexafluorophosphate, 4-isobutylphenyl-4'-methylphenyliodonium hexafluorophosphate (IRGACURE® 250, Ciba Specialty Chemicals), 4-octyloxyphenylphenyliodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxyphenyliodonium hexafluorophosphate. Of all the iodonium salts mentioned, compounds with other anions are, of course, also suitable.

Suitable examples of oximesulfonates are α-(octylsulfonyloxyimino)-4-methoxybenzylcyanide, 2-methyl-α-[5-[4-[[methyl-sulfonyl]oxy]imino]-2(5H)-thienylidene]-benzeneacetonitrile, 2-methyl-α-[5-[4-En-propyl)sulfonyl]oxy]imino]-2(5H)-thienylidene]-benzeneacetonitrile, 2-methyl-α-[5-[4-[[(camphoryl)sulfonyl]oxy]imino]-2(5H)-thienylidene]-benzeneacetonitrile, 2-methyl-α-[5-[4-[[(4-methylphenyl)sulfonyl]oxy]imino]-2(5H)-thienylidene]-benzeneacetonitrile, 2-methyl-α-[5-[4-[[(n-propyl)sulfonyl]oxy]imino]-2(5H)-thienylidene]-benzeneacetonitrile, 2-methyl-α-[5-[[[[4-[[(4-methylphenyl)sulfonyl]oxy]phenyl]sulfonyl]oxy]imino]-2(5H)-thienylidene]-benzeneacetonitrile, 1,1'[1,3-propanediylbis(oxy-4,1-phenylene)]bis[2,2,2-trifluoro-bis[0-(trifluoromethylsulfonyl)oxime]-ethanone, 1,141,3-propanediylbis(oxy-4,1-phenylene)]bis[2,2,2-trifluoro-bis[O-(propylsulfonyl)oxime]-ethanone, 1,1'[1,3-propanediylbis(oxy-4,1-phenylene)]-bis[2,2,2-trifluoro-bis[0-((4-methylphenyl)sulfonyl)oxime]-ethanone, 2-[2,2,3,3,4,4,5,5,6,6,7,7-dodecafluoro-1-(nonafluorobutyl-sulfonyloxyimino)-heptyl]fluorene, 2-[2,2,3,3,4,4,4-heptafluoro-1-(nonafluorobutylsulfonyloxyimino)-butyl]fluorene, 2-[2,2,3,3,4,4,5,5,6,6,7,7-dodecafluoro-1-(nonafluorobutylsulfonyloxyimino)-heptyl]-9-thia-fluorene.

This list is not meant to be conclusive for additional photoinitiator compounds to be used in combination with the novel compounds of the inventions.

Suitable as additional photoinitiators (C) to used in combination with the compounds of the present invention are for example of the formulae (XX), (XXI), (XXII) or (XXIII)

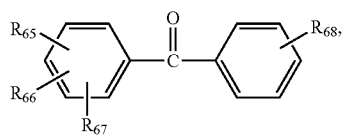
(XX)

wherein $R_{65}$, $R_{66}$ and $R_{67}$ independently of one another are hydrogen, $C_1$-$C_4$-alkyl, $C_1$-$C_4$-halogenalkyl, $C_1$-$C_4$-alkoxy, chlorine or $N(C_1$-$C_4$-alkyl$)_2$;

$R_{68}$ is hydrogen, $C_1$-$C_4$-alkyl, $C_1$-$C_4$-halogenalkyl, phenyl, $N(C_1$-$C_4$-alkyl$)_2$, $COOCH_3$,

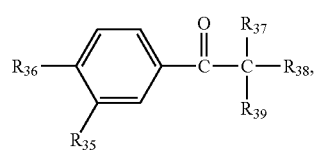 or

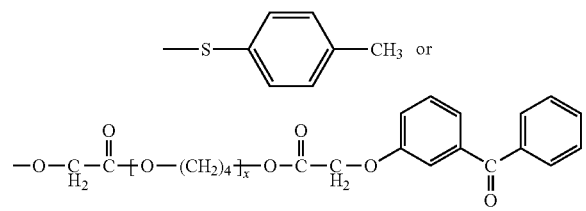

and
x is 2-10;

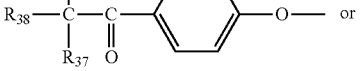
(XXI)

wherein $R_{35}$ is hydrogen or $C_1$-$C_{18}$-alkoxy;

$R_{36}$ is hydrogen, $C_1$-$C_{18}$-alkyl, $C_1$-$C_{12}$hydroxyalkyl, $C_1$-$C_{18}$-alkoxy, —$OCH_2CH_2$—$OR_{39}$, morpholino, $C_1$-$C_{18}$alkyl-S—, a group $H_2C$=CH—, $H_2C$=C(CH$_3$)—,

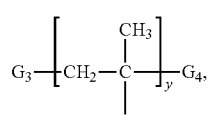

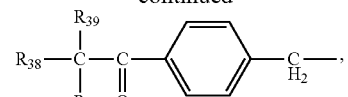

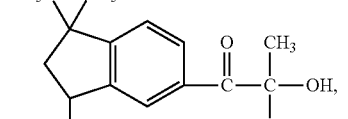

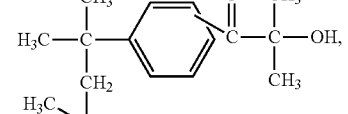

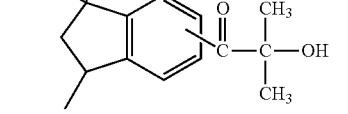

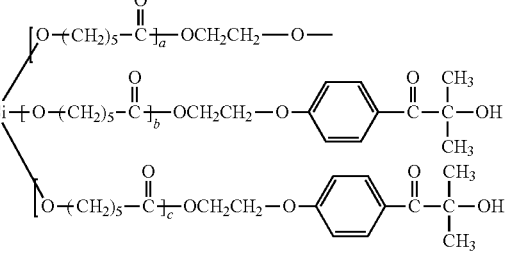

a, b and c are 1-3;
y is 2-10;

$G_3$ and $G_4$ independently of one another are end groups of the polymeric structure, preferably hydrogen or methyl;

$R_{36}$ is hydroxy, $C_1$-$C_{16}$-alkoxy, morpholino, dimethylamino or —$O(CH_2CH_2O)_z$—$C_1$-$C_{16}$-alkyl;

$R_{37}$ and $R_{38}$ independently of one another are hydrogen, $C_1$-$C_6$-alkyl, $C_1$-$C_{16}$-alkoxy or —$O(CH_2CH_2O)_z$—$C_1$-$C_{16}$-alkyl; or unsubstituted phenyl or benzyl; or phenyl or benzyl substituted by $C_1$-$C_{12}$-alkyl; or $R_{37}$ and $R_{38}$ together with the carbon atom to which they are attached form a cyclohexyl ring;

$R_{39}$ is hydrogen, (CO)CH=CH$_2$ or (CO)C(CH$_3$)=CH$_2$;
z is 1-20;

with the proviso that $R_{36}$, $R_{37}$ and $R_{38}$ not all together are $C_1$-$C_{16}$-alkoxy or —$O(CH_2CH_2O)_z$—$C_1$-$C_{16}$-alkyl;

$$R_{41}-\overset{O}{\overset{\|}{P}}-\overset{O}{\overset{\|}{C}}-R_{42},$$
$$\underset{R_{40}}{}$$
(XXII)

wherein $R_{40}$ and $R_{41}$ independently of one another are unsubstituted $C_1$-$C_{20}$-alkyl, cyclohexyl, cyclopentyl, phenyl, naphthyl or biphenylyl; or $C_1$-$C_{20}$-alkyl, cyclohexyl, cyclopentyl, phenyl, naphthyl or biphenylyl substituted by halogen, $C_1$-$C_{12}$-alkyl, $C_1$-$C_{12}$-alkoxy, $C_1$-$C_{12}$alkylthio or $NR_{43}R_{44}$, or $R_{40}$ and $R_{41}$ are independently of one another —(CO)$R_{42}$;

$R_{42}$ is unsubstituted cyclohexyl, cyclopentyl, phenyl, naphthyl or biphenylyl, or cyclohexyl, cyclopentyl, phenyl, naphthyl or biphenylyl substituted by halogen, $C_1$-$C_4$-alkyl and/or $C_1$-$C_4$-alkoxy; or $R_{42}$ is a 5- or 6-membered heterocyclic ring having an S atom or N atom;

$R_{43}$ and $R_{44}$ independently of one another are hydrogen, unsubstituted $C_1$-$C_{12}$-alkyl or $C_1$-$C_{12}$-alkyl substituted by OH or SH wherein the alkyl chain may be interrupted by one to four oxygen atoms; or $R_{43}$ and $R_{44}$ independently of one another are $C_2$-$C_{12}$-alkenyl, cyclopentyl, cyclohexyl, benzyl or phenyl;

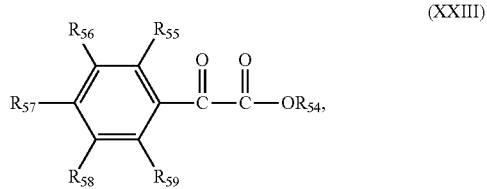

(XXIII)

wherein
$R_{54}$ is hydrogen, $C_1$-$C_{12}$-alkyl or

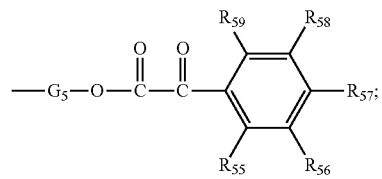

$R_{55}$, $R_{56}$, $R_{57}$, $R_{58}$ and $R_{59}$ independently of one another are hydrogen, unsubstituted $C_1$-$C_{12}$-alkyl or $C_1$-$C_{12}$-alkyl substituted by OH, $C_1$-$C_4$-alkoxy, phenyl, naphthyl, halogen or CN;
wherein the alkyl chain optionally is interrupted by one or more oxygen atoms; or $R_{55}$, $R_{56}$, $R_{57}$, $R_{58}$ and $R_{59}$ independently of one another are $C_1$-$C_4$-alkoxy, $C_1$-$C_4$-alkylthio or $NR_{52}R_{53}$;
$R_{52}$ and $R_{53}$ independently of one another are hydrogen, unsubstituted $C_1$-$C_{12}$-alkyl or $C_1$-$C_{12}$-alkyl substituted by OH or SH wherein the alkyl chain optionally is interrupted by one to four oxygen atoms; or $R_{52}$ and $R_{53}$ independently of one another are $C_2$-$C_{12}$-alkenyl, cyclopentyl, cyclohexyl, benzyl or phenyl; and
$G_5$ is $C_1$-$C_{12}$-alkylene optionally interrupted by one or more oxygen atoms.

The photopolymerizable compositions generally comprise 0.05 to 15% by weight, preferably 0.1 to 10% by weight, of the photoinitiator, based on the composition. The amount refers to the sum of all photoinitiators added, if mixtures of initiators are employed. Accordingly, the amount either refers to the photoinitiator (B) or the photoinitiators (B)+(C).

The photopolymerizable compositions can be used for various purposes, for example for intaglio printing, flexographic printing, screen printing, offset printing, gravure printing, lithography or continuous or dropwise ink-jet printing on for example material pretreated in accordance with the process as disclosed in WO 03/064061 using generally known formulations, for example in publishing, packaging or shipping, in logistics, in advertising, in security printing or in the field of office equipment, as a clear finish, as a colored finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as photoresists, e.g. etch resists, electroplating resists, or permanent resists, both liquid and dry films, as photostructurable dielectricum and as solder masks for electronic circuits, as resists to manufacture color filters for any type of display applications or to generate structures in the manufacturing process of plasma-display panels and electroluminescence displays, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and chips, or as coatings for optical fibres, or for producing optical lenses, e.g. contact lenses or Fresnel lenses.

The compositions according to the invention are further suitable for the production of medical equipment, auxiliaries or implants.

Further the compositions according to the invention are suitable for the preparation of gels with thermotropic properties, as for example described in DE 19700064 and EP 678534. The compositions according to the invention can also be used in dry paint film, as for example described in Paint&Coatings Industry, April 1997, 72 or Plastics World, vol. 54, no. 7, p 48(5).

The compounds of the present invention which as photoactive moiety comprise a photoinitiator of type II, that is a benzophenone, thioxanthone or ketocoumarine moiety can also be used as sensitizers. These are for example compounds of the formula (1) as defined above, which as photoactive moiety Q or $Q_1$ respectively, comprise at least one group of the formula (4), (5), (6), (9), (10) Or (11).

The novel photoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions act as a crosslinking agent which renders the film insoluble. The monounsaturated monomer functions act as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiators and photoinitiator mixtures can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics.

In addition to the novel photoinitiators, the powder coating formulations may also include UV absorbers. To appropriate examples is referred above.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by printing, e.g. by intaglio printing, lithographic printing, flexographic printing, inkjet printing, screen printing, gravure printing, spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.01 μm to more than 100 μm, for example 20 mm or 0.02 to 10 cm, preferably 0.5 to 100 μm.

The compositions according to the invention are also suitable for use in uv-curing adhesives, e.g. in the preparation of pressure-sensitive adhesives, laminating adhesives, hot-melt adhesives, moisture-cure adhesives, silane reactive adhesives or silane reactive sealants and the like, and related applications.

Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The novel photoinitiators further find application in formulations for negative resists, having a very high sensitivity to light and being able to be developed in an aqueous alkaline medium without swelling. They are suitable as photoresists for electronics (electroplating resist, etch resist, solder resist), the production of printing plates, such as offset printing plates or flexo printing plates, for the production of printing forms for relief printing, planographic printing, rotogravure or of screen printing forms, for the production of relief copies, for example for the production of texts in braille, for the production of stamps, for use in chemical milling or as a microresist in the production of integrated circuits. The possible layer supports, and the processing conditions of the coating substrates, are just as varied.

The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing forms are specially treated aluminium, substrates for producing printed circuits are copper-clad laminates, and substrates for producing integrated circuits are silicon wafers. The layer thicknesses for photographic materials and offset printing forms is generally from about 0.5 μm to 10 μm, while for printed circuits it is from 1.0 μm to about 100 μm. Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be addressed pixel by pixel to generate digital images, as is, for example, described by A. Bertsch, J.Y. Jezequel, J.C. Andre in Journal of Photochemistry and Photobiology A: Chemistry 1997, 107, p. 275-281 and by K.-P. Nicolay in Offset Printing 1997, 6, p. 34-37.

Following the imagewise exposure of the material and prior to development, it may be advantageous to carry out thermal treatment for a short time. In this case only the exposed sections are thermally cured. The temperatures employed are generally 50-150° C., preferably 80-130° C.; the period of thermal treatment is in general between 0.25 and 10 minutes. Conjugated polymers, like e.g. polyanilines can be converted from a semiconductive to a conductive state by means of proton doping. The oxime-sulfonates of the present invention can also be used to imagewise irradiate compositions comprising such conjugated polymers in order to form conducting structures (exposed areas) embedded in insulating material (non-exposed areas). Such materials can for example be used as wiring and connecting parts for the production of electric and electronic devices.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset and flexo inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366-370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P.H. Selden in "Glasfaserverstarkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently. The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The photopolymerizable compositions further can be used for the production of functional glass, as is for example described in JP 10 287450 A.

The photocurable compositions of the invention can further be used for curing of charged monomers, e.g. acrylates with $NH_4Cl$-groups etc. usw. Such compositions are for example employed for preparing polyelektrolytes or corresponding copolymers.

The invention also provides a process for the photopolymerization of monomeric, oligomeric or polymeric compounds containing at least one ethylenically unsaturated double bond, which comprises adding to the abovementioned compounds at least one photoinitiator or photoinitiator mixture as described above and irradiating the resulting composition with electromagnetic radiation, for example light of the wavelength 200 to 600 nm; as well as the use of a photoinitiator or photoinitiator mixture as defined above for the photopolymerization of monomeric, oligomeric or polymeric compounds containing at least one ethylenically unsaturated double bond.

The invention additionally provides the use of compositions as described above for producing pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules; as well as a process for producing pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

The invention further provides a coated substrate which is coated on at least one surface with a composition as described above, and a polymerized or crosslinked composition obtained by curing a polymerizable composition as described above.

The sensitivity of the novel compositions to radiation generally extends from about 190 nm through the UV region and into the infrared region (about 20,000 nm, in particular 1200 nm), especially from 190 nm to 650 nm (depending on the photoinititator moiety, optionally in combination with a sensitizer as described hereinbefore) and therefore spans a very broad range. Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, super high-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, electron beams and X-rays. The distance between the lamp and the substrate to be exposed in accordance with the invention may vary depending on the intended application and the type and output of lamp, and may be, for example, from 1 cm to 150 cm. Laser light sources, for example excimer lasers, such as krypton F lasers for exposure at 248 nm are also suitable. Lasers in the visible region can also be employed.

Alternatively, the actinic radiation is provided by light emitting diodes (LED) or organic light emitting diodes (OLED), e.g. UV light emitting diodes (UV-LED). Said LEDs allow instant on and off switching of the radiation source. Further, UV-LEDs generally have a narrow wavelength distribution and offer the possibility to customize the peak wavelength and also provide an efficient conversion of electric energy to UV radiation.

As mentioned above, depending on the light source used it is advantageous in many cases to employ a sensitizer, as described above, whose absorption spectrum coincides as closely as possible to the emission spectrum of the radiation source.

The examples which follow illustrate the invention in more detail, without restriciting the scope of the invention to said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

PREPARATION EXAMPLES

Intermediate compounds which are employed to prepare the compounds of the following examples: (in the formulae below and the examples the groups

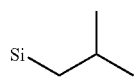

at the Si-atoms are not meant to define free bonds, but

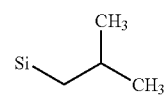

=isobutyl)

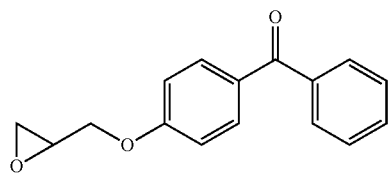 [SMILES: O=C(c1ccccc1)c1ccc(OCC2CO2)cc1]

(4-Oxiranylmethoxy-phenyl)-phenyl-methanone is prepared from (4-hydroxy-phenyl)-phenyl-methanone and 2-chloromethyl-oxirane as taught by e.g. T. Nishikubo et al., *Macromolecules* 1998, 31, 2789-2796.

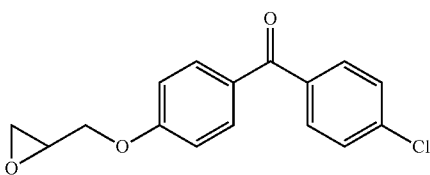 [SMILES: O=C(c1ccc(Cl)cc1)c1ccc(OCC2CO2)cc1]

(4-Chloro-phenyl)-(4-oxiranylmethoxy-phenyl)-methanone is prepared similarly to (4-oxiranylmethoxy-phenyl)-phenyl-methanone from (4-chloro-phenyl)-(4-hydroxy-phenyl)methanone and 2-chloromethyl-oxirane.

Off-white powder, mp. 96° C.; $^1$H NMR (300 MHz, CDCl$_3$), δ [ppm]: 7.79 (d, J=8.90 Hz, 2H), 7.71 (d, J=8.59 Hz, 2H), 7.45 (d, J=8.59 Hz, 2H), 6.99 (d, J=8.91 Hz, 2H), 4.37-4.32 (m, dd-like, 1H), 4.05-3.99 (m, dd-like, 1H), 3.42-3.36 (m, 1H), 2.96-2.93 (m, t-like, 1H), 2.80-2.77 (m, dd-like, 1H). GLC/MS (CI), m/z (%). found 289 (100), calcd. 288 ($C_{16}H_{13}ClO_3$).

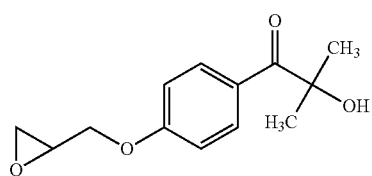 [SMILES: CC(C)(O)C(=O)c1ccc(OCC2CO2)cc1]

2-Hydroxy-2-methyl-1-(4-oxiranylmethoxy-phenyl)-propan-1-one is prepared from 2-hydroxy-1-(4-hydroxy-phenyl)-2-methyl-propan-1-one and 2-chloromethyl-oxirane as taught by e.g. EP281941

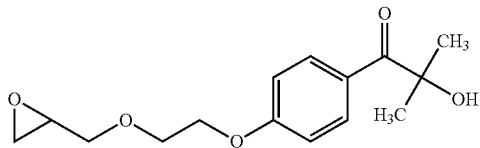 [SMILES: CC(C)(O)C(=O)c1ccc(OCCOCC2CO2)cc1]

2-Hydroxy-2-methyl-1-[4-(2-oxiranylmethoxy-ethoxy)phenyl]-propan-1-one is prepared from 2-hydroxy-1-[4-(2-hydroxy-ethoxy)-phenyl]-2-methyl-propan-1-one and 2-chloromethyl-oxirane as taught by e.g. EP281941.

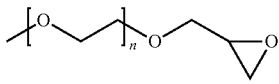

n = 7.2

MPEG 350 glycidyl ether is obtained from MPEG 350 (polyethylene glycol monomethyl ether), epichlorohydrin and sodium hydroxide following standard literature methods.

Colorless liquid; assay (meq epoxide/g). found 2.25. calcd. 2.46. MS (pos. APCI), m/z. found 264.9, 309.1, 353.2, 397.1, 441.2, 485.3, 529.1 and 573.2. calcd. 264 ($C_{12}H_{24}O_6$, n=4), 308 ($C_{14}H_{28}O_7$, n=5), 352 ($C_{16}H_{32}O_8$, n=6), 396 ($C_{18}H_{36}O_9$, n=7), 440 ($C_{20}H_{40}C_{10}$, n=8), 484 ($C_{22}H_{44}O_{11}$, n=9), 528 ($C_{24}H_{48}O_{12}$, n=10) and 572 ($C_{26}H_{52}O_{13}$, n=11).

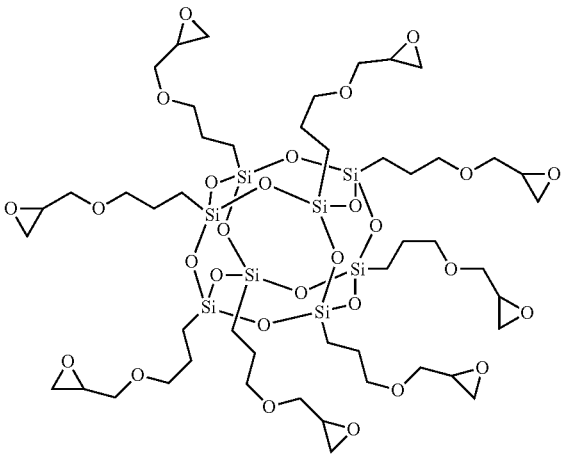 [SMILES: C(COCC1CO1)C[Si]12O[Si]3(CCCOCC4CO4)O[Si]4(CCCOCC5CO5)O[Si](CCCOCC5CO5)(O1)O[Si]1(CCCOCC5CO5)O[Si](CCCOCC5CO5)(O2)O[Si](CCCOCC2CO2)(O3)O[Si](CCCOCC2CO2)(O4)O1]

$T_n$-$(C_6H_{11}O_2)_n$ is sold by Hybrid Plastics (Glycidyl POSS, EP0409; cage mixture n=8, 10, 12; n=8 shown); 5.9 meq epoxide/g (calcd. 6.0), corresponding to a ratio Si /epoxide of 1/0.98 (mol/mol); GPC (polystyrene calibrated; RI detector, THF), $M_n$ (n)/$M_w$/PDI (% area): 1225 (7.3)/1376/1.12 (74) and 3250 (19.4)/3589/1.10 (26); $^{29}$Si NMR: T3

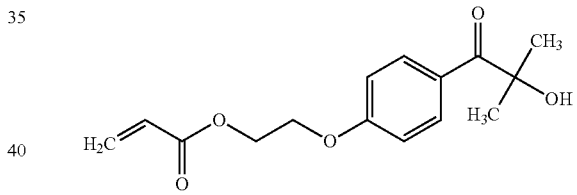

Acrylic acid 2-[4-(2-hydroxy-2-methyl-propionyl)-phenoxy]-ethyl ester is prepared from (4-hydroxy-phenyl)-phenyl-methanone and acryloyl chloride as taught by e.g. DE3534645

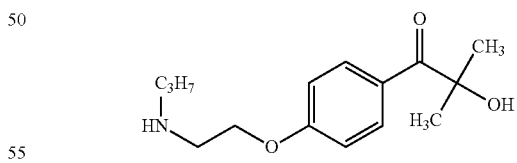

2-Hydroxy-2-methyl-1-[4-(2-propylamino-ethoxy)-phenyl]-propan-1-one is prepared from methanesulfonic acid 2-[4-(2-hydroxy-2-methyl-propionyl)-phenoxy]-ethyl ester and propylamine in analogy to WO03/042724 (example A-1; preparation of 2-hydroxy-1-{4-[2-(2-hydroxy-ethylamino)ethoxy]-phenyl}-2-methyl-propan-1-one from methanesulfonic acid 2-[4-(2-hydroxy-2-methyl-propionyl)-phenoxy]-ethyl ester and 2-aminoethanol).

Beige powder, mp. 89° C.; $^1$H NMR (300 MHz, CDCl$_3$), δ [ppm]: 8.05 (d, J=9.0 Hz, 2H), 6.95 (d, J=9.0 Hz, 2H), 4.15 (t, J=5.2 Hz, 2H), 3.04 (t, J=5.2 Hz, 2H), 2.68-2.63 (m, t-like, 2H), 1.63 (s, 6H), 1.61-1.49 (m, 2H), 0.94 (t, J=7.4 Hz, 3H); MS (pos. APCI), m/z (%). found 266.15 (100), calcd. 265 ($C_{16}H_{23}NO_3$).

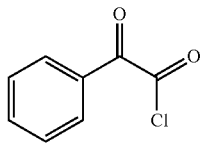 [SMILES: O=C(Cl)C(=O)c1ccccc1]

Oxo-phenyl-acetyl chloride is prepared from oxo-phenyl-acetic acid and oxalyl chloride as taught by S. Miyano et al., J. Chem. Soc., Perkin Trans. 1, 2002, 377-383.

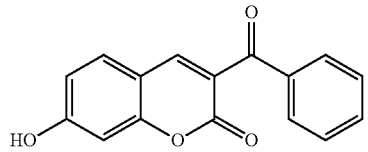 [SMILES: O=C(c1ccccc1)c1cc2ccc(O)cc2oc1=O]

3-Benzoyl-7-hydroxy-1-benzopyran-2-one is prepared according to patent application WO 2005/014677

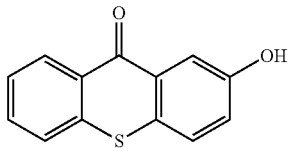 [SMILES: O=c1c2ccccc2sc2ccc(O)cc12]

2-Hydroxy-thioxanthen-9-one is prepared according to W. B. Price and S. Smiles, Journal of the Chemical Society 1928, 3154

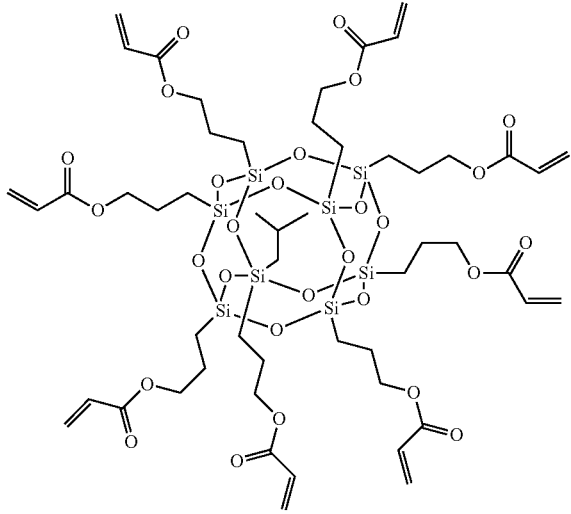

$T_n$-$(C_6H_9O_2)_n$ is sold by Hybrid Plastics (Acrylo POSS, MA0736; cage mixture n=8, 10, 12; n=8 shown); found 5.3 meq acrylate/g (calcd. 6.1), corresponding to a ratio Si/acrylate of 1/0.87 (mol/mol); GPC (polystyrene calibrated; RI detector, THF), $M_n$ (n)/W/PDI (% area): 1560 (9.4)/1591/1.02 (87) and 2839 (17.2)/2928/1.03 (13).

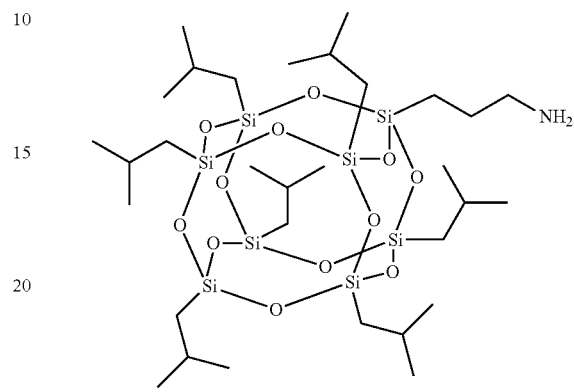

($^{i}$Bu)$_7$-$T_8$-($CH_2CH_2CH_2NH_2$), 3,5,7,9,11,13,15-heptakis-(2-methylpropyl)-penta-cyclo[9.5.1.13,9.15,15.17,13]octasiloxane-1-propanamine (CAS regno 444 315-15-5); sold by Hybrid Plastics (Aminopropylisobutyl POSS, AM0265); elemental analysis (%) for $C_{31}H_{71}NO_{12}Si_8$ (874.60): found N1.18 (0.84 meq/g). calcd. N1.60 (1.14 meq/g).

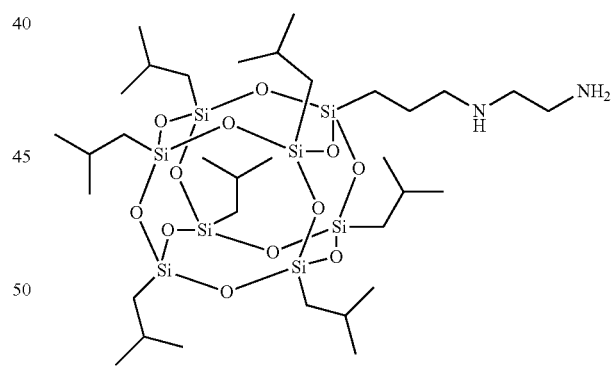

($^{i}$Bu)$_7$-$T_8$-($CH_2CH_2CH_2NHCH_2CH_2NH_2$), N1-[3-[3,5,7,9,11,-13,15-heptakis(2-methylpropyl)pentacyclo[9.5.1.13,9.-15,15. 17,13]octa siloxan-1-yl]propyl]-1,2-ethanediamine (CAS regno. 444315-16-6); sold by e.g. Hybrid Plastics (Aminoethylaminopropylisobutyl POSS, AM0275); elemental analysis (%) for $C_{33}H_{76}N_2O_{12}Si_8$ (917.67): found N 2.95 (2.11 meq/g). calcd. N 3.05 (2.18 meq/g).

Example 1

Preparation of

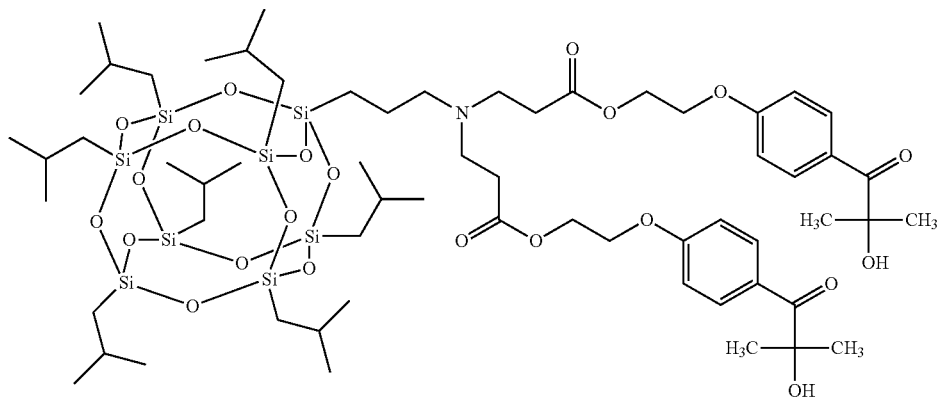 [SMILES: CC(C)C[Si]12O[Si]3(CCCN(CCC(=O)OCCOc4ccc(C(=O)C(C)(C)O)cc4)CCC(=O)OCCOc4ccc(C(=O)C(C)(C)O)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

[Compound of formula (1); seven A=isobutyl; one A=formula (2); L=propylene; E=direct bond; $R_1$=$R_2$=Q; Q=formula (3); p=0; $R_{10}$=$R_9$=methyl; X=$OR_5$; $R_5$=hydrogen; $Z_1$=**Obutylene interrupted by (CO)O].

A solution of $(^iBu)_7$-$T_8$-$(CH_2CH_2CH_2NH_2)$ (AM0265, 0.84 meq N/g; 1.81 g, 1.5 mmol) and acrylic acid 2-[4-(2-hydroxy-2-methyl-propionyl)-phenoxy]-ethyl ester (0.83 g, 3.0 mmol) in chloroform (20 ml) is stirred 24 hours at 50° C., the course of the reaction being monitored by GLC. The solvent of the resulting clear solution is distilled off by means of a rotary evaporator to afford a white solid (2.65 g).

MS (pos. APCI), m/z (%). found 1431.59 (100), 1152.49 (30), 874.33 (25). calcd. 1429 ($C_{61}H_{107}NO_{22}Si_8$; title compound), 1151 ($C_{46}H_{89}NO_{17}Si_8$; product derived from mono-addition of acrylic acid 2-[4-(2-hydroxy-2-methyl-propionyl)-phenoxy]-ethyl ester to $(^iBu)_7$-$T_8$-$(CH_2CH_2CH_2NH_2)$), 873 ($C_{31}H_{71}NO_{12}Si_8$-; $(^iBu)_7$-T8-$(CH_2CH_2CH_2NH_2)$).

[Compound of formula (1); seven A=isobutyl; one A=formula (2); L=propylene; E=direct bond; $R_1$=$R_2$=Q; Q=formula (3); p=0; $R_{10}$=$R_9$=methyl; X=$OR_5$; $R_5$=hydrogen; $Z_1$=**Opentylene interrupted by two O and substituted by $OR_6$; $R_6$=hydrogen]

A suspension of $(^iBu)_7$-$T_8$-$(CH_2CH_2CH_2NH_2)$ (AM0265, 0.84 meq N/g; 1.81 g, 1.5 mmol) and 2-hydroxy-2-methyl-1-[4-(2-oxiranylmethoxy-ethoxy)-phenyl]-propan-1-one (92%; 0.97 g, 3.2 mmol) in a mixture of ethanol (16 ml) and chloroform (4 ml) is stirred 24 hours at 50° C., the course of the reaction being monitored by GLC. The solvent of the resulting clear solution is distilled off by means of a rotary evaporator to afford a white solid.

MS (pos. APCI), m/z (%). found 1436.14 (100). calcd. 1433 ($C_{61}H_{111}NO_{22}Si_8$; title compound).

Example 2

Preparation of

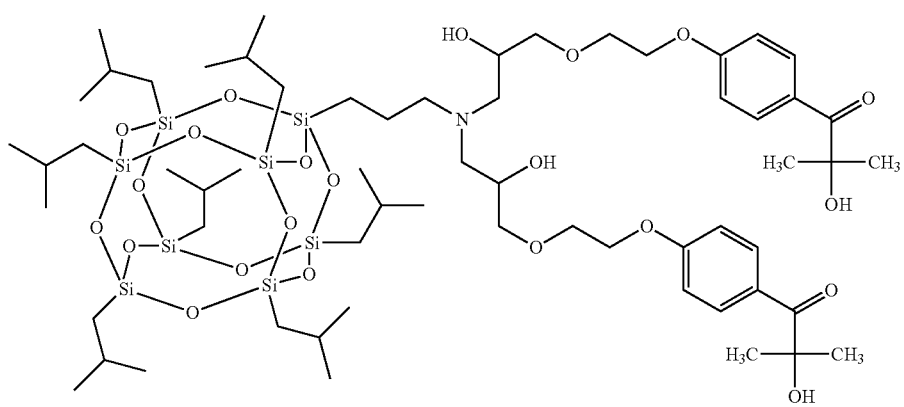 [SMILES: CC(C)C[Si]12O[Si]3(CCCN(CC(O)COCCOc4ccc(C(=O)C(C)(C)O)cc4)CC(O)COCCOc4ccc(C(=O)C(C)(C)O)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

Example 3

Preparation of

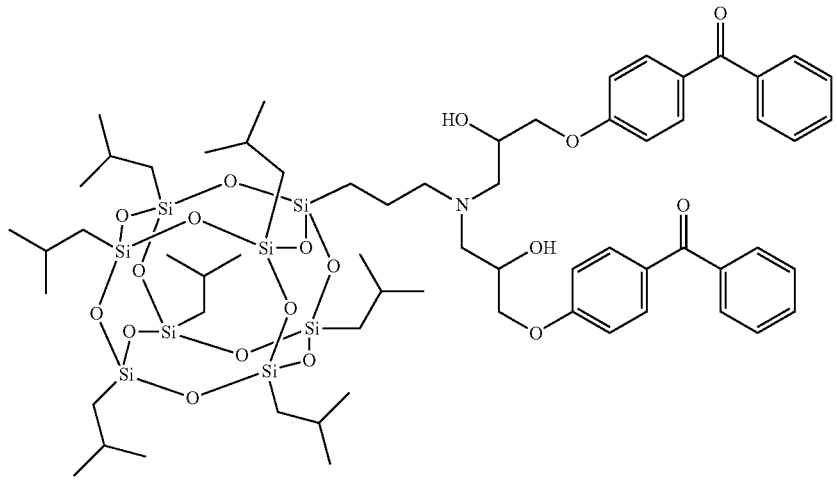 [SMILES: CC(C)C[Si]12O[Si]3(CCCN(CC(O)COc4ccc(C(=O)c5ccccc5)cc4)CC(O)COc4ccc(C(=O)c5ccccc5)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

[Compound of formula (1); seven A=isobutyl; one A=formula (2); L=propylene; E=direct bond; $R_1$=$R_2$=Q; Q=formula (4); $R_{12}$=$R_{13}$=$R_{14}$=hydrogen; $Z_2$=**Oproplene substituted by $OR_6$; $R_6$=hydrogen]

A suspension of ($^i$Bu)$_7$-T$_8$-(CH$_2$CH$_2$CH$_2$NH$_2$) (AM0265, 0.84 meq N/g; 1.18 g, 1.0 mmol) and (4-oxiranylmethoxy-phenyl)-phenyl-methanone (95%; 0.53 g, 2.0 mmol) in ethanol (20 ml) is stirred 24 hours at reflux, the course of the reaction being monitored by GLC. The solvent of the resulting clear solution is distilled off by means of a rotary evaporator to afford a white solid (1.75 g). MS (pos. APCI), m/z (%). found 1382.61 (100). calcd. 1381 ($C_{63}H_{99}NO_{18}Si_8$; title compound).

Example 4

Preparation of

[Compound of formula (1); seven A=isobutyl; one A=formula (2); L=propylene; E=direct bond; $R_1$=Q; Q=formula (3); p=0; $R_{10}$=$R_9$=methyl; X=$OR_5$; $R_5$=hydrogen; $Z_1$=**Opentylene interrupted by O and substituted by $OR_6$; $R_6$=hydrogen; $R_2$=heptyl interrupted by one O and substituted by $OR_6$; $R_6$=hydrogen]

A suspension of ($^i$Bu)$_7$-T$_8$-(CH$_2$CH$_2$CH$_2$NH$_2$) (AM0265, 0.84 meq N/g; 0.59 g, 0.5 mmol), 2-hydroxy-2-methyl-1-[4-(2-oxiranylmethoxy-ethoxy)-phenyl]-propan-1-one (94%; 0.15 g, 0.5 mmol) and 2-butoxymethyl-oxirane (0.065 g, 0.5 mmol) in ethanol (5 ml) is stirred 24 hours at 50° C., the course of the reaction being monitored by GLC. The solvent of the resulting clear solution is distilled off by means of a rotary evaporator to afford 0.73 g of a white solid.

MS (pos. APCI), m/z (%). found 1435.70 (25), 1284.99 (100), 1135.03 (65). calcd. 1433. ($C_{61}H_{111}NO_{22}Si_8$; compound 2), 1283 ($C_{53}H_{105}NO_{19}Si_8$, title compound), 1133 ($C_{45}H_{99}NO_{16}Si_8$, product derived from double-addition of 2-butoxymethyl-oxirane to ($^i$Bu)$_7$-T$_8$-(CH$_2$CH$_2$CH$_2$NH$_2$)).

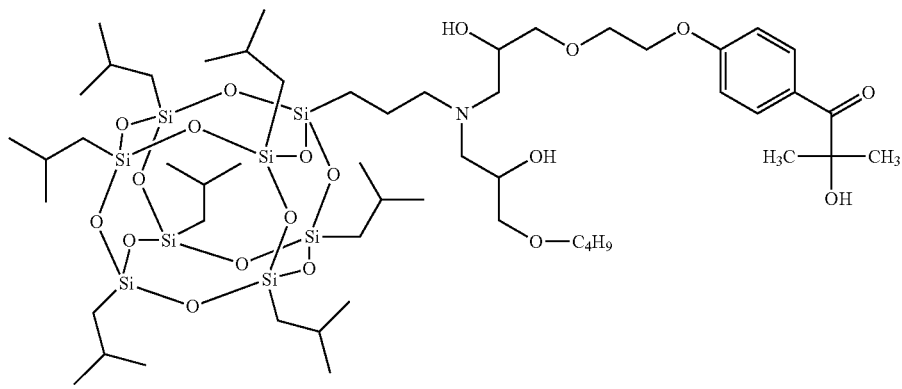

Example 5

Preparation of

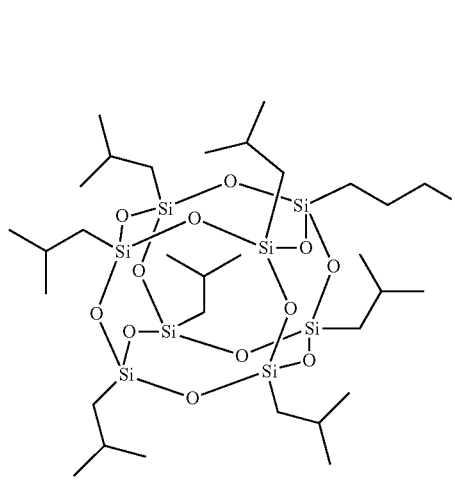
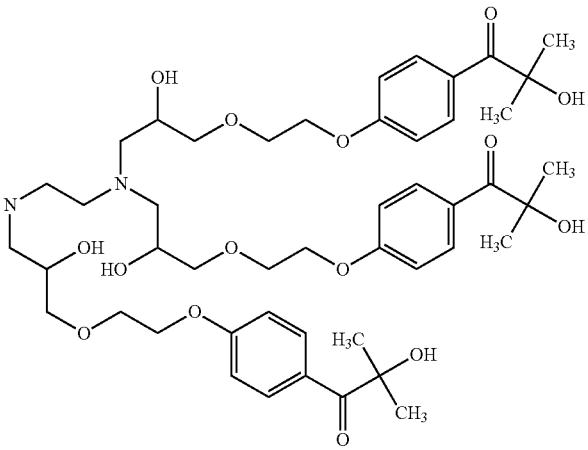

[Compound of formula (1); seven A=isobutyl; one A=formula (2); L=propylene; E=ethyleneNR$_3$; R$_3$=R$_1$=R$_2$=Q; Q=formula (3); p=0; R$_{10}$=R$_9$=methyl; X=OR$_5$; R$_5$=hydrogen; Z$_1$=**Opentylene interrupted by O and substituted by OR$_6$; R$_6$=hydrogen]

A suspension of ($^i$Bu)$_7$-T$_8$-(CH$_2$CH$_2$CH$_2$NHCH$_2$CH$_2$NH$_2$) (AM0275, 2.11 meq N/g; 0.47 g, 1.0 mmol) and 2-hydroxy-2-methyl-1-[4-(2-oxiranylmethoxy-ethoxy)-phenyl]-propan-1-one (94%; 0.89 g, 3.0 mmol) in ethanol (20 ml) is stirred 24 hours at reflux, the course of the reaction being monitored by GLC. The solvent of the resulting clear solution is distilled off by means of a rotary evaporator to afford a colourless resin (1.15 g).

MS (pos. APCI), m/z (%). found 1758.79 (100). calcd. 1756 (C$_{78}$H$_{136}$N$_2$O$_{27}$Si$_8$; title compound).

Example 6

Preparation of a Mixture of Silsequioxanes

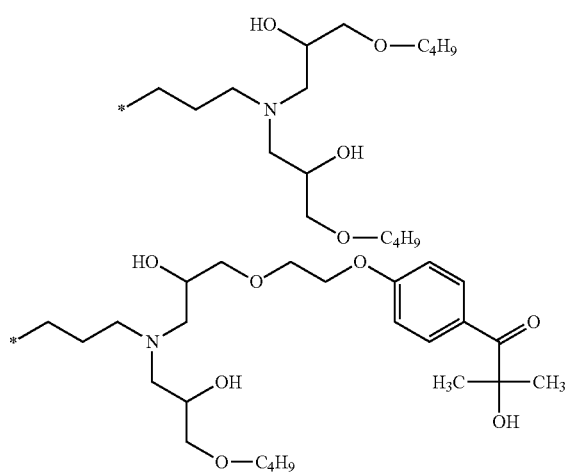

[wherein the asterisk * denotes the silsequioxane basic structure, which is composed of a mixture of polyhedral oligomeric silsesquioxanes containing silicon compounds according to formula (1) in which n=6, 8, 10, 12.

Different A are a group of formula (2) wherein
(i) L=propylene, E=direct bond, R$_1$=R$_2$=heptylene interrupted by O and substituted by OR$_6$, R$_6$=hydrogen;
(ii) L=propylene, E=direct bond, R$_1$=heptylene interrupted by O and substituted by OR$_6$, R$_6$=hydrogen; R$_2$=Q, Q=formula (3); p=0; R$_9$=R$_{10}$=methyl; X=OR$_5$; R$_5$=H; Z$_1$=Opentylene interrupted by O and substituted by OR$_6$, R$_6$=hydrogen;
(iii) L=propylene, E=direct bond, R$_1$=R$_2$=Q, Q=formula (3); p=0; Z$_1$=O-pentylene interrupted by 0 and substituted by OR$_6$, R$_6$=hydrogen]

The mixture is obtained by ring opening addition of 2-hydroxy-2-methyl-1-[4-(2-oxiranylmethoxy-ethoxy)-phenyl]-propan-1-one (0.5 eq) and 2-butoxymethyl-oxirane (1.5 eq) to hydrolyzed 3-(trimethoxysilyl)-1-propanamine.

6.a) 3-(Trimethoxysilyl)-1-propanamine (97%; 22.2 g, 0.12 mol) is slowly added to stirred ethanol (190 ml) containing water (21 ml, 1.17 mol). The mixture is brought to 50° C. and stirring continued for 20 hours. The solution is carefully concentrated on a rotary evaporator such as to avoid gelling, re-dissolved in ethanol (50 ml) and re-concentrated.

$^{29}$Si NMR: T3; MS (pos. ESI), m/z (%). found 1322.4 (11), 1101.3 (49), 881.2 (69), 661.3 (12). calcd. 1320 ($C_{36}H_{96}N_{12}O_{18}Si_{12}$; $T_{12}$-($CH_2CH_2CH_2NH_2$)$_{12}$), 1100 ($C_{30}H_{80}N_{10}O_{15}Si_{10}$; $T_{10}$-($CH_2CH_2CH_2NH_2$)$_{10}$), 880 ($C_{24}H_{64}N_8O_{12}Si_8$; $T_8$-($CH_2CH_2CH_2NH_2$)$_8$), 660 ($C_{18}H_{48}N_6O_9Si_6$; $T_6$-($CH_2CH_2CH_2NH_2$)$_6$).

6.b) The concentrated solution is diluted with ethanol (150 ml) followed by slow addition of a solution of 2-hydroxy-2-methyl-1-[4-(2-oxiranylmethoxy-ethoxy)-phenyl]-propan-1-one (98%; 17.2 g, 0.06 mol) in ethanol (50 ml). The mixture is brought to 50° C. and stirred for 4 hours, the course of the reaction being monitored by GLC. 2-Butoxymethyl-oxirane (90%; 26 g, 0.18 mol) is added at once and the solution stirred at 50° C. overnight to afford the title compound as a slightly yellow ethanolic solution (216.7 g).

The photoinitiator concentration of the solution as determined by UV-VIS is equivalent to 5.3% w/w 2-hydroxy-1-[4-(2-hydroxy-ethoxy)-phenyl]-2-methyl-propan-1-one (Irgacure® 2959); the solid content of the dispersion, obtained by evaporation of the solvent, is 24.8%; elemental analysis (%). found C, 55.70; H, 9.14. N, 2.79. thermogravimetric analysis (TGA; % residue). found 15.8.

Example 7

Preparation of the Compound as Described in Example 6

To prepare the compound the same procedure as described in example 6 is followed, except that in step 6.b) the final solution is concentrated using a rotary evaporator. The photoinitiator concentration of the solution as determined by UV-VIS is equivalent to 14.1% w/w 2-hydroxy-1-[4-(2-hydroxy-ethoxy)-phenyl]-2-methyl-propan-1-one (Irgacure® 2959); the solid content of the dispersion, obtained by evaporation of the solvent, is 61.7%; elemental analysis (%): found N 2.83 (combustion), N 2.71 (perchloric acid titration).

$^{29}$Si NMR: T3; MS (pos. MALDI), m/z: distribution curve ranging from 2'000 (ca) to 6'000 (ca) with a broad maximum at 3'800 (ca); GPC (PS calibration; molecular weight peak). found 3'675; ($^iBu$)$_7$-$T_8$-($CH_2CH_2CH_2NH_2$) (comparison). found 714. calcd. 874.60 ($C_{31}H_{71}NO_{12}Si_8$).

Example 8

Preparation of the Compound as Described in Example 6, Except that the Amount of 2-hydroxy-2-methyl-1-[4-(2-oxiranylmethoxy-ethoxy)-phenyl]-propan-1-one (1.0 eq) is Increased at the Expense of 2-butoxymethyl-oxirane (1.0 Eq).

8.a) 3-(Trimethoxysilyl)-1-propanamine (97%; 1.9 g, 0.01 mol) is slowly added to stirred ethanol (16 ml) containing water (1.7 ml, 0.09 mol). The mixture is brought to 50° C. and stirring continued for 20 hours. The solution is then treated as described for 6.a).

8.b) The concentrated solution is diluted with ethanol (12 ml) followed by slow addition of a solution of 2-hydroxy-2-methyl-1-[4-(2-oxiranylmethoxy-ethoxy)-phenyl]-propan-1-one (98%; 2.9 g, 0.01 mol) in ethanol (4 ml). The mixture is brought to 50° C. and stirred for 3 hours, the course of the reaction being monitored by GLC. 2-Butoxymethyl-oxirane (95%; 1.37 g, 0.01 mol) is added at once and the solution stirred at 50° C. overnight to afford the title compound as a slightly yellow ethanolic solution (15.9 g).

The photoinitiator concentration of the solution as determined by UV-VIS is equivalent to 12.1% w/w 2-hydroxy-1-[4-(2-hydroxy-ethoxy)-phenyl]-2-methyl-propan-1-one (Irgacure® 2959); the solid content of the dispersion, obtained by evaporation of the solvent, is 38.7%; elemental analysis (%). found C, 56.21; H, 8.68. N 2.42. TGA (% residue). found 19.4.

$^{29}$Si NMR: T3; MS (pos. MALDI), m/z: distribution curve ranging from 2'600 (ca) to 6'600 (ca) with a broad maximum at 4'400 (ca).

Example 9

The compound as described in example 8 is prepared via premature ring opening addition of 2-hydroxy-2-methyl-1-[4-(2-oxiranylmethoxy-ethoxy)-phenyl]-propan-1-one (leg) and 2-butoxymethyl-oxirane (1 eq) to (non-hydrolyzed) 3-(triethoxysilyl)-1-propanamine followed by hydrolysis of the mixture of alkylated 3-(triethoxysilyl)-1-propanamines thus obtained.

9.a) 2-Hydroxy-2-methyl-1-[4-(2-oxiranylmethoxy-ethoxy)-phenyl]-propan-1-one (95%; 2.95 g, 0.01 mol) is slowly added to a stirred solution of (triethoxysilyl)-1-propanamine (2.21 g, 0.01 mol) in ethanol (16 ml). The solution is brought to 50° C. and stirred for 20 hours, the reaction being monitored by GLC. 2-Butoxymethyl-oxirane (95%; 1.37 g, 0.01 mol) is added at once and the solution stirred at 50° C. for 24 hours to afford a mixture of (triethoxysilyl)-1-propanamines 9a-(I), 9a-(II) and 9a-(III):

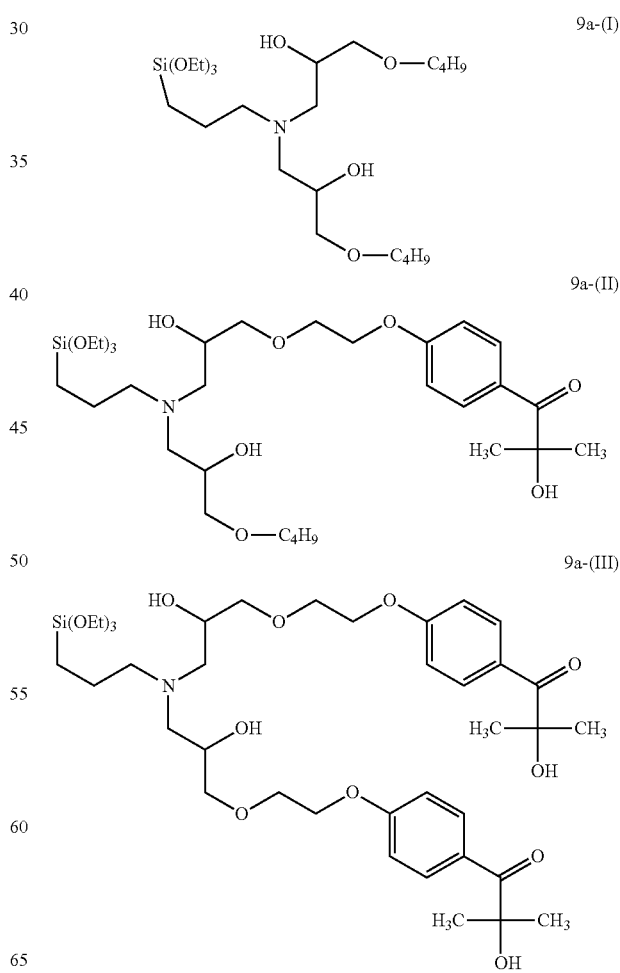

$^{29}$Si NMR: TO; MS (pos. APCI), m/z (%). found 782.53 (90), 632.48 (100), 482.44 (100); calcd. 781 ($C_{39}H_{63}NO_{13}Si$; 9a-(III)), 631 ($C_{31}H_{57}NO_{10}Si$; 9a-(II)), 481 ($C_{23}H_{51}NO_7Si$; 9a-(I)).

9.b) The solution is slowly added to stirred ethanol (12 ml) containing water (1.3 ml, 0.07 mol). The mixture is brought to 50° C. and stirred for 20 hours. Evaporation of the solvent leaves a mixture containing the title compound as slightly yellow resin (5.2 g).

$^{29}$Si NMR: T0, T3; MS (pos. MALDI), m/z: distribution curve ranging from 2'600 (ca) to 6'600 (ca) with a broad maximum at 4'400 (ca).

Example 10

Preparation of a Mixture of Silsequioxanes

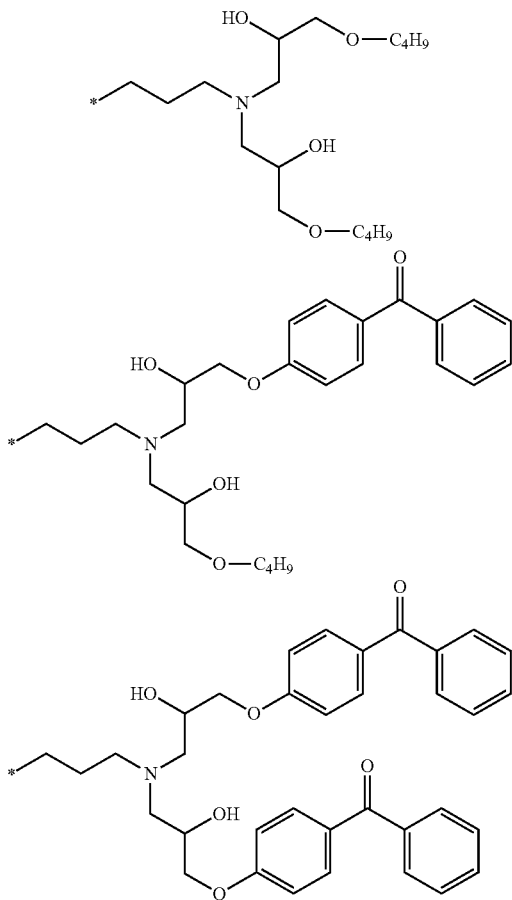

[wherein the asterisk * denotes the silsequioxane basic structure, which is composed of a mixture of polyhedral oligomeric silsesquioxanes containing silicon compounds according to formula (1) in which n=6, 8, 10, 12.

Different A are a group of formula (2) wherein (i) L=propylene, E=direct bond, $R_1$=$R_2$=heptylene interrupted by O and substituted by $OR_6$, $R_6$, =hydrogen;

(ii) L=propylene, E=direct bond, $R_1$=heptylene interrupted by O and substituted by $OR_6$, $R_6$, =hydrogen; $R_2$=Q, Q=formula (4); $Z_1$=O-propylene substituted by $OR_6$, $R_6$=hydrogen; $R_{12}$, $R_{13}$, $R_{14}$=hydrogen;

(iii) L=propylene, E=direct bond, $R_1$=$R_2$=Q, Q=formula (4); $Z_1$=O-propylene substituted by $OR_6$, $R_6$=hydrogen; $R_{12}$, $R_{13}$, $R_{14}$=hydrogen]

The mixture is obtained by ring opening addition of (4-oxiranylmethoxy-phenyl)-phenyl-methanone (0.5 eq) and 2-butoxymethyl-oxirane (1.5 eq) to hydrolyzed 3-(trimethoxysilyl)-1-propanamine.

10.a) 3-(Trimethoxysilyl)-1-propanamine (97%; 37 g, 0.2 mol) is slowly added to stirred ethanol (320 ml) containing water (35 ml, 1.94 mol). The mixture is brought to 50° C. and stirring continued for 20 hours. The solution is then treated as described for 6a.

10.b) The concentrated solution is diluted with ethanol (200 ml) followed by slow addition of a solution of (4-oxiranylmethoxy-phenyl)-phenyl-methanone (98%; 26 g, 0.1 mol) in ethanol (100 ml). The mixture is brought to 50° C. and stirred for 3 hours, the course of the reaction being monitored by GLC. 2-Butoxymethyl-oxirane (95%; 41.4 g, 0.3 mol) is added at once and the solution stirred at 50° C. overnight to afford the title compound as a slightly yellow ethanolic solution (387.8 g).

The photoinitiator concentration of the solution as determined by UV-VIS is equivalent to 5.9% w/w (4-methoxy-phenyl)-phenyl-methanone; the solid content of the dispersion, obtained by evaporation of the solvent, is 16.8%; elemental analysis (%). found C, 57.08; H, 8.33; N 3.52. TGA (% residue). found 19.6.

Example 11

Preparation of the compound as described in example 10, except that in this batch the final solution is concentrated using a rotary evaporator. The photoinitiator concentration of the solution as determined by UV-VIS is equivalent to 15.4% w/w (4-methoxy-phenyl)-phenyl-methanone; the solid content of the dispersion, obtained by evaporation of the solvent, is 58.3%.

$^{29}$Si NMR: T3; MS (pos. MALDI), m/z: distribution curve ranging from 2'000 (ca) to 6'000 (ca) with a broad maximum at 3'700 (ca); GPC(PS calibration; molecular weight peak). found 3'000.

Example 12

Preparation of the compound as described in example 8, except prepared at larger scale.

12.a) 3-(Trimethoxysilyl)-1-propanamine (97%; 52.7 g, 0.28 mol) is slowly added to stirred ethanol (420 ml) containing water (48 ml, 2.67 mol). The mixture is brought to 50° C. and stirring continued for 20 hours. The solution is carefully concentrated on a rotary evaporator such as to avoid gelling, re-dissolved in ethanol (100 ml) and re-concentrated.

12.b) The concentrated solution is diluted with ethanol (320 ml) followed by slow addition of a solution of 2-hydroxy-2-methyl-1-[4-(2-oxiranylmethoxy-ethoxy)-phenyl]-propan-1-one (95%; 84 g, 0.28 mol) in ethanol (100 ml). The mixture is brought to 50° C. and stirred for 4 hours, the course of the reaction being monitored by GLC. 2-Butoxymethyl-oxirane (95%; 39 g, 0.28 mol) is added at once and the solution stirred at 50° C. for 20 hours to afford the title compound as a slightly yellow ethanolic solution (478 g).

The photoinitiator concentration of the solution as determined by UV-VIS is equivalent to 10.4% w/w 2-hydroxy-1-[4-(2-hydroxy-ethoxy)-phenyl]-2-methyl-propan-1-one (Irgacure® 2959); the solid content of the dispersion, obtained by evaporation of the solvent, is 34%.

Example 13

Preparation of

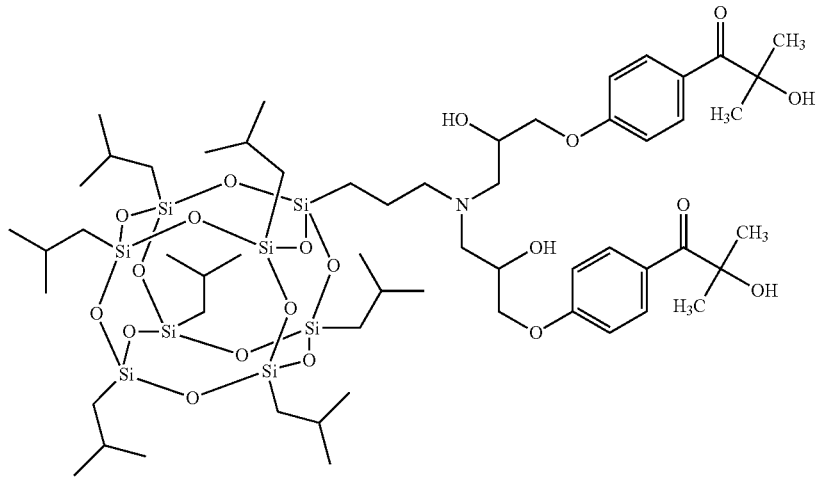 [SMILES: CC(C)C[Si]12O[Si]3(CCCN(CC(O)COc4ccc(C(=O)C(C)(C)O)cc4)CC(O)COc4ccc(C(=O)C(C)(C)O)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

[Compound of formula (1); seven A=isobutyl; one A=formula (2); L=propylene; E=direct bond; $R_1=R_2=Q$; Q=formula (3); p=0; $R_9=R_{10}$=methyl; X=OR$_5$; $R_5$=hydrogen; $Z_1$=**Opropylene substituted by OR$_6$; $R_6$=hydrogen]

A suspension of ($^i$Bu)$_7$-T$_8$-(CH$_2$CH$_2$CH$_2$NH$_2$) (AM0265, 0.84 meq N/g; 0.1205 g, 0.1012 mmol) and 2-hydroxy-2-methyl-1-(4-oxiranylmethoxy-phenyl)-propan-1-one (86%; 0.0612 g, 0.2228 mmol) in ethanol (4 ml) is stirred 24 hours at reflux, the course of the reaction being monitored by GLC. The solvent of the resulting clear solution is distilled off by means of a rotary evaporator to afford a white solid (0.2075 g).

MS (pos. APCI), m/z (%). found 1347.38 (100). calcd. 1345 (C$_{57}$H$_{103}$NO$_{20}$Si$_8$; title compound).

Example 14

Preparation of

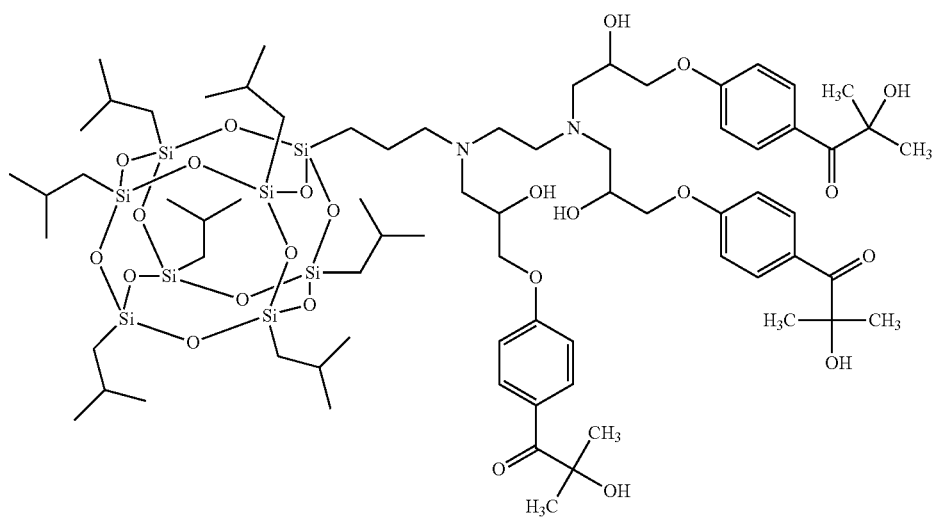 [SMILES: CC(C)C[Si]12O[Si]3(CCCN(CCN(CC(O)COc4ccc(C(=O)C(C)(C)O)cc4)CC(O)COc4ccc(C(=O)C(C)(C)O)cc4)CC(O)COc4ccc(C(=O)C(C)(C)O)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

[Compound of formula (1); seven A=isobutyl; one A=formula (2); L=propylene; E=ethylene NR$_3$; $R_3=R_1=R_2$=Q; Q=formula (3); p=0; $R_9=R_{10}$=methyl; X=OR$_5$; $R_5$=hydrogen;

$Z_1$=**Opropylene substituted by OR$_6$; $R_6$=hydrogen]

A suspension of ($^i$Bu)$_7$-T$_8$-(CH$_2$CH$_2$CH$_2$NHCH$_2$CH$_2$NH$_2$) (AM0275, 2.11 meq N/g; 0.0613 g, 0.1293 mmol) and 2-hydroxy-2-methyl-1-(4-oxiranylmethoxy-phenyl)-propan-1-one (86%; 0.0586 g, 0.2133 mmol) in ethanol (5 ml) is stirred 24 hours at reflux, the course of the reaction being monitored by GLC. The solvent of the resulting clear solution is distilled off by means of a rotary evaporator to afford a colourless, slightly opaque waxy solid (0.135 g).

MS (pos. APCI), m/z (%). found 1627.38 (100). calcd. 1624 ($C_{72}H_{124}N_2O_{24}Si_8$; title compound).

Example 15

Preparation of

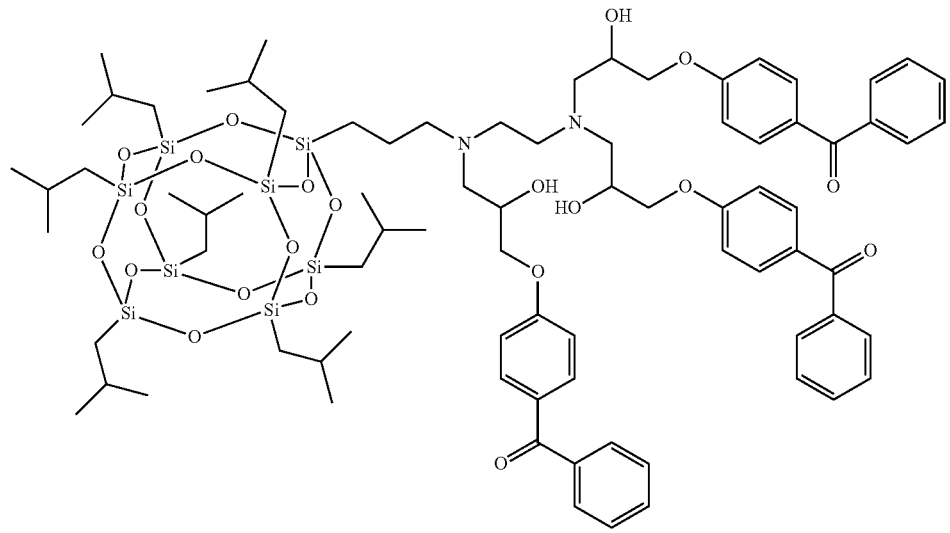 [SMILES: CC(C)C[Si]12O[Si]3(CCCN(CCN(CC(O)COc4ccc(C(=O)c5ccccc5)cc4)CC(O)COc4ccc(C(=O)c5ccccc5)cc4)CC(O)COc4ccc(C(=O)c5ccccc5)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

[Compound of formula (1); seven A=isobutyl; one A=formula (2); L=propylene; E=ethylene $NR_3$; $R_3=R_1=R_2=Q$; Q=formula (4); $R_{12}=R_{13}=R_{14}$=hydrogen; $Z_2$=**Opropylene substituted by $OR_6$; $R_6$=hydrogen]

A suspension of ($^iBu$)$_7$-$T_8$-($CH_2CH_2CH_2NHCH_2CH_2NH_2$) (AM0275, 2.11 meq N/g; 0.0573 g, 0.1209 mmol) and (4-oxiranylmethoxy-phenyl)-phenyl-methanone (95%; 0.0534 g, 0.1995 mmol) in ethanol (5 ml) is stirred 24 hours at reflux, the course of the reaction being monitored by GLC. The solvent of the resulting clear solution is distilled off by means of a rotary evaporator to afford a colourless, slightly opaque waxy solid (0.129 g).

MS (pos. APCI), m/z (%). found 1682.67 (100), 1427.82 (45). calcd. 1678 ($C_{81}H_{118}N_2O_{21}Si_8$; title compound), 1424 ($C_{65}H_{104}N_2O_{18}Si_8$; product derived from double-addition of (4-oxiranylmethoxy-phenyl)-phenyl-methanone to ($^iBu$)$_7$-$T_8$-($CH_2CH_2CH_2NHCH_2CH_2NH_2$).

Example 16

Preparation of

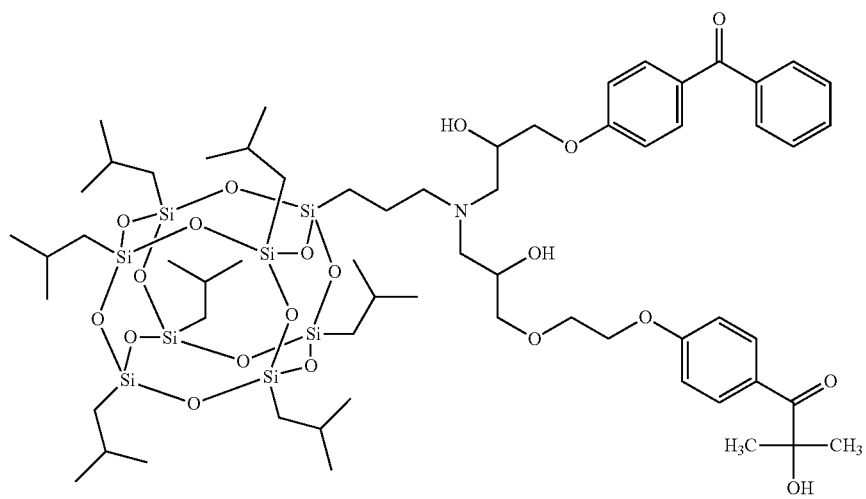 [SMILES: CC(C)C[Si]12O[Si]3(CCCN(CC(O)COCCOc4ccc(C(=O)C(C)(C)O)cc4)CC(O)COc4ccc(C(=O)c5ccccc5)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

[Compound of formula (1); seven A=isobutyl; one A=formula (2); L=propylene; E=direct bond; $R_1=Q$; Q=formula (3); p=0; $R_9=R_{10}$=methyl; $X=OR_5$;

$R_5$=hydrogen; $Z_1$=**Opentylene interrupted by O and substituted by $OR_6$; $R_6$=hydrogen;

$R_2$=Q; Q=formula (4); $R_{12}$=$R_{13}$=$R_{14}$=hydrogen; $Z_2$=**Opropylene substituted by $OR_6$; $R_6$=hydrogen]

A suspension of $(^iBu)_7$-$T_8$-$(CH_2CH_2CH_2NH_2)$ (AM0265, 0.84 meq N/g; 0.2233 g, 0.1876 mmol), (4-oxiranylmethoxyphenyl)-phenyl-methanone (95%; 0.0555 g, 0.2073 mmol) and 2-hydroxy-2-methyl-1-[4-(2-oxiranylmethoxy-ethoxy)-phenyl]-propan-1-one (95%; 0.0610 g, 0.2067 mmol) in ethanol (10 ml) is stirred 24 hours at reflux, the course of the reaction being monitored by GLC. The solvent of the resulting clear solution is distilled off by means of a rotary evaporator to afford a colourless, slightly opaque waxy solid (0.3767 g).

MS (pos. APCI), m/z (%). found 1383.60 (45), 1409.62 (100), 1434.57 (50). calcd. 1381. ($C_{63}H_{99}NO_{18}Si_8$; compound 3), 1407 ($C_{62}H_{105}NO_{20}Si_8$; title compound), 1433 ($C_{61}H_{111}NO_{22}Si_8$; compound 2).

Example 17

Preparation of

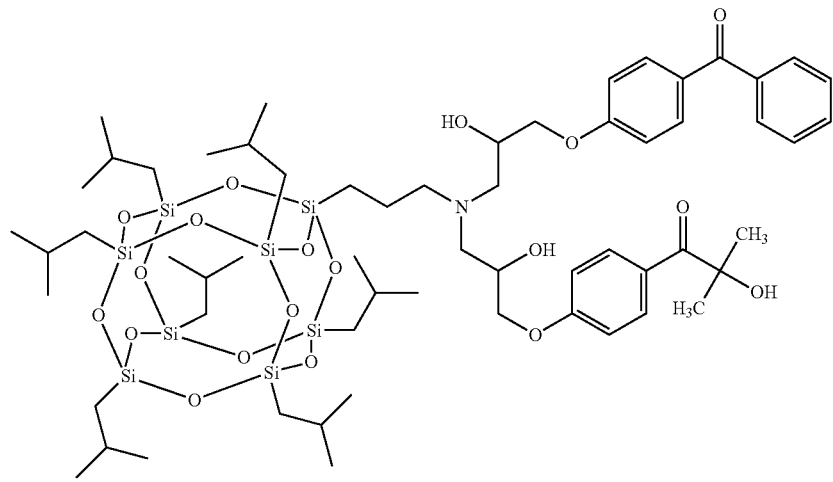 [SMILES: CC(C)C[Si]12O[Si]3(CCCN(CC(O)COc4ccc(C(=O)c5ccccc5)cc4)CC(O)COc4ccc(C(=O)C(C)(C)O)cc4)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

[Compound of formula (1); seven A=isobutyl; one A=formula (2); L=propylene; E=direct bond;

$R_1$=Q; Q=formula (3); p=0; $R_9$=$R_{10}$=methyl; X=$OR_5$; $R_5$=hydrogen; $Z_1$=Opropylene substituted by $OR_6$; $R_6$=Hydrogen $R_2$=Q; Q=formula (4); $R_{12}$=$R_{13}$=$R_{14}$=hydrogen; $Z_2$=Opropylene substituted by $OR_6$; $R_6$=Hydrogen]

A suspension of $(^iBu)_7$-$T_8$-$(CH_2CH_2CH_2NH_2)$ (AM0265, 0.84 meq N/g; 0.2027 g, 0.1703 mmol), (4-oxiranylmethoxyphenyl)-phenyl-methanone (95%; 0.0506 g, 0.1890 mmol) and 2-hydroxy-2-methyl-1-(4-oxiranylmethoxy-phenyl)-propan-1-one (86%; 0.0515 g, 0.1875 mmol) in ethanol (10 ml) is stirred 24 hours at reflux, the course of the reaction being monitored by GLC. The solvent of the resulting clear solution is distilled off by means of a rotary evaporator to afford a colourless, slightly opaque waxy solid (0.3637 g).

MS (pos. APCI), m/z (%). found 1347.56 (40), 1365.55 (100), 1382.49 (45). calcd. 1345. ($C_{57}H_{103}NO_{20}Si_8$; compound 13), 1363 ($C_{60}H_{101}NO_{19}Si_8$; title compound), 1381 ($C_{63}H_{99}NO_{18}Si_8$; compound 3).

Example 18

Same as example 6, except that the amount of 2-hydroxy-2-methyl-1-[4-(2-oxiranylmethoxyethoxy)-phenyl]-propan-1-one (1.9 eq) is increased at the expense of 2-butoxymethyl-oxirane (0.1 eq).

The compound is a mixture of polyhedral oligomeric silsesquioxanes containing silicon compounds according to formula (1) in which n=6, 8, 10, 12 and A is

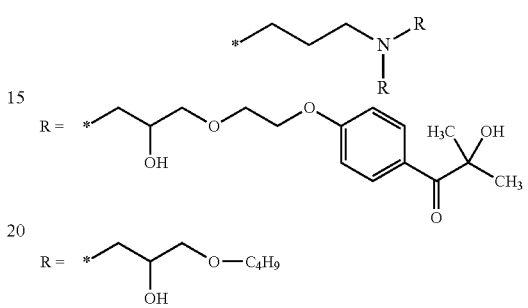

obtained by ring opening addition of 2-hydroxy-2-methyl-1-[4-(2-oxiranylmethoxy-ethoxy)phenyl]-propan-1-one (1.9 eq) and 2-butoxymethyl-oxirane (0.1 eq) to hydrolyzed 3-(trimethoxysilyl)-1-propanamine.

18.a) 3-(Trimethoxysilyl)-1-propanamine (97%; 1.9 g, 0.01 mol) is slowly added to stirred ethanol (16 ml) containing water (1.7 ml, 0.09 mol). The mixture is brought to 50° C. and stirring continued for 20 hours. The solution is carefully concentrated on a rotary evaporator such as to avoid gelling, re-dissolved in ethanol (10 ml) and re-concentrated.

18.b) The concentrated solution is diluted with ethanol (12 ml) followed by slow addition of a solution of 2-hydroxy-2-methyl-1-[4-(2-oxiranylmethoxy-ethoxy)-phenyl]-propan-1-one (94%; 5.6 g, 0.019 mol) in ethanol (4 ml). The mixture is brought to 50° C. and stirred for 24 hours, the course of the reaction being monitored by GLC. To complete the reaction stirring is continued over the weekend. 2-Butoxymethyl-oxirane (95%; 0.14 g, 0.001 mol) is added and the mixture stirred at 50° C. (20 hours) to afford the title compound as a slightly yellow ethanolic solution (19 g).

The photoinitiator concentration of the solution as determined by UV-VIS/by weight is equivalent to 18.6%/22.2% w/w 2-hydroxy-1-[4-(2-hydroxy-ethoxy)-phenyl]-2-methyl-propan-1-one (Irgacure® 2959); the solid content of the dispersion, obtained by evaporation of the solvent, is 35%; elemental analysis (%). found C, 58.09; H, 7.62. N, 2.10. TGA (% residue): found 10.5.

DLS (ethanol, 25° C.), z-average size [nm]/PDI: 6.05/0.183.

$^{29}$Si NMR: T3; MS (pos. MALDI), m/z: distribution curve ranging from 2'600 (ca) to 6'600 (ca) with a broad maximum at 4'700 (ca).

Example 19

Mixture of polyhedral oligomeric silsesquioxanes containing silicon compounds according to formula (1) in which n=6, 8, 10, 12 and A is

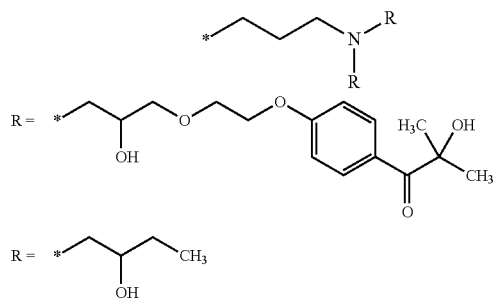

obtained by ring opening addition of 2-hydroxy-2-methyl-1-[4-(2-oxiranylmethoxy-ethoxy)phenyl]-propan-1-one (1.9 eq) and 1,2-epoxybutane (0.1 eq) to hydrolyzed 3-(trimethoxysilyl)-1-propanamine.

19.a) 3-(Trimethoxysilyl)-1-propanamine (97%; 1.84 g, 0.01 mol) is slowly added to stirred n-propanol (16 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (10 ml) and re-concentrated.

19.b) The concentrated solution is diluted with n-propanol (16 ml) followed by addition of 2-hydroxy-2-methyl-1-[4-(2-oxiranylmethoxy-ethoxy)-phenyl]-propan-1-one (94%; 5.7 g, 0.019 mol) dissolved in n-propanol (4 ml). The mixture is brought to 80° C. and stirred for 44 hours, the course of the reaction being monitored by GLC. 1,2-Epoxybutane (0.21 g, 0.003 mol) is added and the mixture stirred at 60° C. (4 hours). Volatiles are then removed using a rotary evaporator to afford a slightly yellow resin (6.9 g). The photoinitiator concentration as determined by weight is equivalent to 62.1% w/w 2-hydroxy-1-[4-(2-hydroxy-ethoxy)phenyl]-2-methyl-propan-1-one (IRGACURE® 2959).

GPC (polystyrene calibrated; RI detector, THF), $M_n/M_w$/PDI (% area): 5'021/6'598/1.31 (87.6).

An aliquot (6.6 g) is mixed with Sartomer SR344 (1.7 g) and IRGASTAB® UV22 (0.08 g) [IRGASTAB® UV22 is a polymerization inhibitor, a quinone derivative in propoxylated glycerol tri-acrylate, provided by Ciba Inc.] using chloroform as auxiliary solvent to afford, after removal of the solvent, a reduced viscosity-sample (8.38 g). The photoinitiator concentration as determined by weight is equivalent to 48.9% w/w 2-hydroxy-1-[4-(2-hydroxy-ethoxy)phenyl]-2-methyl-propan-1-one (IRGACURE® 2959).

Example 20

Mixture of polyhedral oligomeric silsesquioxanes containing silicon compounds according to formula (1) in which n=6, 8, 10, 12 and A is

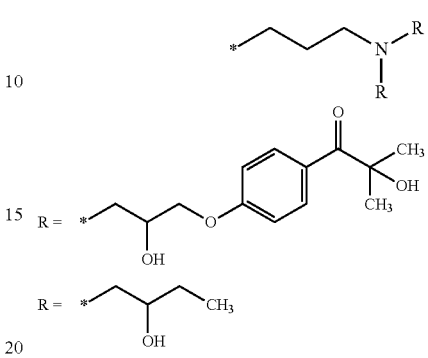

obtained by ring opening addition of 2-hydroxy-2-methyl-1-(4-oxiranylmethoxy-phenyl)-propan-1-one (1.9 eq) and 1,2-epoxybutane (0.1 eq) to hydrolyzed 3-(trimethoxysilyl)-1-propanamine.

20.a) 3-(Trimethoxysilyl)-1-propanamine (97%; 1.84 g, 0.01 mol) is slowly added to stirred ethanol (16 ml) containing water (1.8 ml, 0.1 mol). The mixture is brought to 60° C. and stirring continued for 20 hours. The solution is carefully concentrated on a rotary evaporator such as to avoid gelling. The obtained concentrate is twice subjected to a re-dissolution (ethanol; 10 ml)-re-concentration cycle.

20.b) The concentrated solution is diluted with ethanol (16 ml) followed by addition of 2-hydroxy-2-methyl-1-(4-oxiranylmethoxy-phenyl)-propan-1-one (4.48 g, 0.019 mol). The mixture is refluxed for 48 hours, the course of the reaction being monitored by GLC. 1,2-Epoxybutane (0.21 g, 0.003 mol) is added and the mixture stirred at 65° C. (5 hours). Volatiles are then removed using a rotary evaporator to afford a slightly yellow resin (5.45 g).

The photoinitiator concentration as determined by weight is equivalent to 78.0% w/w 2-hydroxy-1-[4-(2-hydroxy-ethoxy)-phenyl]-2-methyl-propan-1-one.

GPC (polystyrene calibrated; RI detector, THF), $M_n/M_w$/PDI (% area): 3'260/4'690/1.4 (81).

The product (5.45 g) is mixed with Sartomer SR344 (1.32 g) and IRGASTAB UV22 (0.05 g) using chloroform as auxiliary solvent to afford, after removal of the solvent, a reduced viscosity-sample (6.7 g).

The photoinitiator concentration as determined by weight is equivalent to 63.5% w/w 2-hydroxy-1-[4-(2-hydroxy-ethoxy)-phenyl]-2-methyl-propan-1-one.

Example 21

Same as example 10, except that the reaction is run in n-propanol and the final product dispersed in TPGDA.

Mixture of polyhedral oligomeric silsesquioxanes containing silicon compounds according to formula (1) in which n=6, 8, 10, 12 and A is

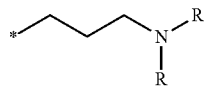

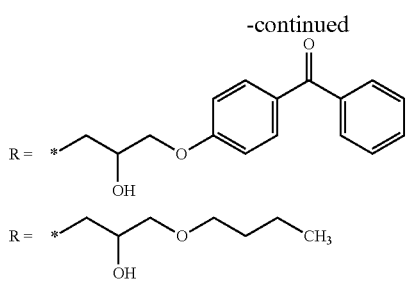

obtained by ring opening addition of (4-oxiranylmethoxy-phenyl)-phenyl-methanone (0.5 eq) and 2-butoxymethyl-oxirane (1.5 eq) to hydrolyzed 3-(trimethoxysilyl)-1-propanamine 21.a) 3-(Trimethoxysilyl)-1-propanamine (97%; 9.2 g, 0.05 mol) is slowly added to stirred n-propanol (78 ml) containing water (9 ml, 0.5 mol). The mixture is brought to 60° C. and stirring continued for 20 hours. The solution is carefully concentrated on a rotary evaporator such as to avoid gelling, re-dissolved in n-propanol (20 ml) and re-concentrated.

21.b) The concentrated solution is diluted with n-propanol (50 ml) followed by addition of (4-oxiranylmethoxy-phenyl)-phenyl-methanone (96%; 6.6 g, 0.025 mol). The mixture is brought to 80° C. and stirred for 3 hours, the course of the reaction being monitored by GLC. 2-Butoxymethyl-oxirane (95%; 10.3 g, 0.075 mol) is added and the solution stirred at 80° C. overnight to afford a clear solution (62.2 g). A sample is withdrawn, evaporated to dryness and characterized by GPC.

GPC (polystyrene calibrated; RI detector, THF), $M_n/M_w$/PDI (% area): 2'828/3'355/1.19 (83).

Tripropylene glycol diacrylate (4.14 g) is then added to the solution (ca. 60 g) and volatiles removed using a rotary evaporator to afford a slightly yellow resin (26.05 g). photoinitiator concentration as determined by weight is equivalent to 20.3% w/w (4-methoxy-phenyl)-phenyl-methanone.

Example 22

Same as example 21, except that the amount of (4-oxiranylmethoxy-phenyl)-phenyl-methanone (1.0 eq) is increased at the expense of 2-butoxymethyl-oxirane (1.0 eq). Mixture of polyhedral oligomeric silsesquioxanes containing silicon compounds according to formula (1) in which n=6, 8, 10, 12 and A is

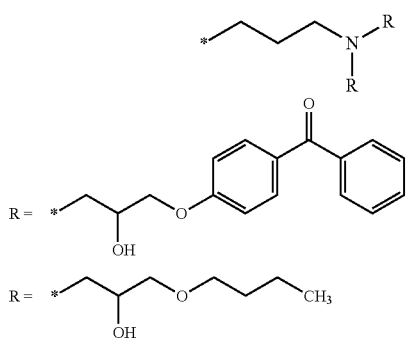

obtained by ring opening addition of (4-oxiranylmethoxy-phenyl)-phenyl-methanone (1 eq) and 2-butoxymethyl-oxirane (leg) to hydrolyzed 3-(trimethoxysilyl)-1-propanamine.

22.a) 3-(Trimethoxysilyl)-1-propanamine (97%; 7.4 g, 0.04 mol) is slowly added to stirred n-propanol (60 ml) containing water (6.6 ml, 0.37 mol). The mixture is brought to 60° C. and stirring continued for 20 hours. The solution is carefully concentrated on a rotary evaporator such as to avoid gelling, re-dissolved in n-propanol (20 ml) and re-concentrated.

22.b) The concentrated solution is diluted with n-propanol (50 ml) followed by addition of (4-oxiranylmethoxy-phenyl)-phenyl-methanone (95%; 10.7 g, 0.04 mol). The mixture is brought to 80° C. and stirred for 2.5 hours, the course of the reaction being monitored by GLC. 2-Butoxymethyl-oxirane (95%; 5.5 g, 0.04 mol) is added and the solution stirred at 80° C. for 20 hours to afford a slightly milky dispersion (58.3 g). A sample is withdrawn, evaporated to dryness and characterized by GPC.

GPC (polystyrene calibrated; RI detector, THF), $M_n/M_w$/PDI (% area): 3'387/3'917/1.16 (87.6).

Tripropylene glycol diacrylate (4.97 g) is then added to the dispersion (ca. 57 g) and volatiles removed using a rotary evaporator to afford a slightly yellow resin (25 g).

The photoinitiator concentration as determined by weight is equivalent to 33.9% w/w (4-methoxy-phenyl)-phenyl-methanone.

Example 23

Same as example 21, except that the amount of (4-oxiranylmethoxy-phenyl)-phenyl-methanone (1.5 eq) is increased at the expense of 2-butoxymethyl-oxirane (0.5 eq). Mixture of polyhedral oligomeric silsesquioxanes containing silicon compounds of formula (1) in which n=6, 8, 10, 12 and A is

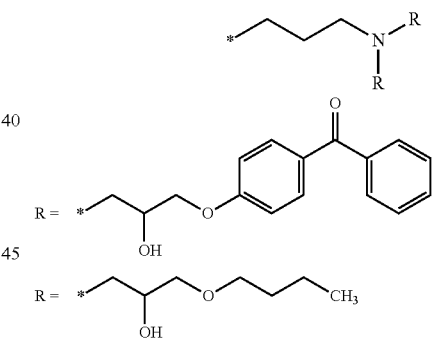

obtained by ring opening addition of (4-oxiranylmethoxy-phenyl)-phenyl-methanone (1.5 eq) and 2-butoxymethyl-oxirane (0.5 eq) to hydrolyzed 3-(trimethoxysilyl)-1-propanamine.

23.a) 3-(Trimethoxysilyl)-1-propanamine (97%; 3.7 g, 0.02 mol) is slowly added to stirred n-propanol (31 ml) containing water (3.6 ml, 0.2 mol). The mixture is brought to 60° C. and stirring continued for 20 hours. The solution is carefully concentrated on a rotary evaporator such as to avoid gelling, re-dissolved in n-propanol (15 ml) and re-concentrated.

23.b) The concentrated solution is diluted with n-propanol (30 ml) followed by addition of (4-oxiranylmethoxy-phenyl)-phenyl-methanone (96%; 7.9 g, 0.03 mol). The mixture is brought to 80° C. and stirred for 2.5 hours, the course of the reaction being monitored by GLC. 2-Butoxymethyl-oxirane (95%; 1.37 g, 0.01 mol) is added and the dispersion stirred at 80° C. overnight to afford a milky dispersion (32.3 g). A sample is withdrawn, evaporated to dryness and characterized by GPC.

GPC (polystyrene calibrated; RI detector, THF), $M_n/M_w$/PDI (% area): 3'193/3'593/1.13 (82).

Tripropylene glycol diacrylate (3.05 g) is then added to the dispersion (ca. 30 g) and volatiles removed using a rotary evaporator to afford a slightly yellow resin (14.45 g).

The photoinitiator concentration as determined by weight is equivalent to 43.8% w/w (4-methoxy-phenyl)-phenyl-methanone.

Example 24

Similar to example 21, except that the amount of (4-oxiranylmethoxy-phenyl)-phenyl-methanone (2 eq) is increased at the expense of 2-butoxymethyl-oxirane (0 eq).

Mixture of polyhedral oligomeric silsesquioxanes containing silicon compounds of formula (1) in which n=6, 8, 10, 12 and A is

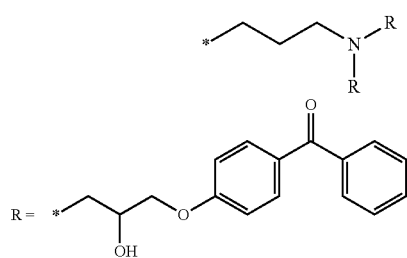

obtained by ring opening addition of (4-oxiranylmethoxy-phenyl)-phenyl-methanone (2 eq) to hydrolyzed 3-(trimethoxysilyl)-1-propanamine.

24.a) 3-(Trimethoxysilyl)-1-propanamine (97%; 3.7 g, 0.02 mol) is slowly added to stirred n-propanol (32 ml) containing water (3.6 ml, 0.2 mol). The mixture is brought to 60° C. and stirring continued for 20 hours. The solution is carefully concentrated on a rotary evaporator such as to avoid gelling, re-dissolved in n-propanol (15 ml) and re-concentrated.

24.b) The concentrated solution is diluted with n-propanol (32 ml) followed by addition of (4-oxiranylmethoxy-phenyl)-phenyl-methanone (96%; 10.6 g, 0.04 mol) and 1,4-dioxane (10 ml). The mixture is brought to 80° C. and stirred for 24 hours, the course of the reaction being monitored by GLC. Volatiles are then removed using a rotary evaporator to afford a slightly yellow resin (13.1 g).

The photoinitiator concentration as determined by weight is equivalent to 64.8% w/w (4-methoxy-phenyl)-phenyl-methanone.

GPC (polystyrene calibrated; RI detector, THF), $M_n/M_w$/PDI (% area): 4'125/4'404/1.07 (100).

The product (13.1 g) is mixed with Sartomer SR344 (2.3 g) and IRGASTAB UV22 (0.1 g) using 1,4-dioxane (15 ml) as auxiliary solvent to afford, after removal of the solvent, a reduced viscosity-sample (15.4 g).

The photoinitiator concentration as determined by weight is equivalent to 55.1% w/w (4-methoxy-phenyl)-phenyl-methanone.

Example 25

Similar to example 21, except that 2-butoxymethyl-oxirane is replaced by 1,2-epoxybutane. Mixture of polyhedral oligomeric silsesquioxanes containing silicon compounds of formula (1) in which n=6, 8, 10, 12 and A is

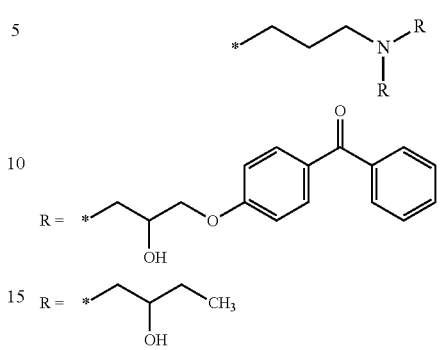

obtained by ring opening addition of (4-oxiranylmethoxy-phenyl)-phenyl-methanone (0.5 eq) and 1,2-epoxybutane (1.5 eq) to hydrolyzed 3-(trimethoxysilyl)-1-propanamine 25.a) 3-(Trimethoxysilyl)-1-propanamine (97%; 9.2 g, 0.05 mol) is slowly added to stirred n-propanol (78 ml) containing water (9 ml, 0.5 mol). The mixture is brought to 50° C. and stirring continued for 20 hours. The solution is carefully concentrated on a rotary evaporator such as to avoid gelling, re-dissolved in n-propanol (50 ml) and re-concentrated.

25.b) The concentrated solution is diluted with n-propanol (50 ml) followed by addition of (4-oxiranylmethoxy-phenyl)-phenyl-methanone (95%; 6.6 g, 0.025 mol). The mixture is brought to 50° C. and stirred for 2.5 hours, the course of the reaction being monitored by GLC. 1,2-Epoxybutane (5.4 g, 0.075 mol) is added and the solution stirred at 50° C. overnight to afford a dispersion (61.4 g). A sample is withdrawn, evaporated to dryness and characterized by GPC.

GPC (polystyrene calibrated; RI detector, THF), $M_n/M_w$/PDI (% area): 1'437/2'486/1.73 (100).

Tripropylene glycol diacrylate (3.3 g) is then added to the dispersion (ca. 60 g) and volatiles removed using a rotary evaporator to afford a slightly yellow resin (20.8 g).

The photoinitiator concentration as determined by weight is equivalent to 25.2% w/w (4-methoxy-phenyl)-phenyl-methanone.

Example 26

Similar to example 22, except that 2-butoxymethyl-oxirane is replaced by 1,2-epoxybutane. Mixture of polyhedral oligomeric silsesquioxanes containing silicon compounds of formula (1) in which n=6, 8, 10, 12 and A is

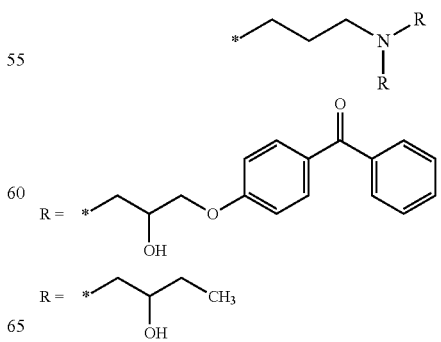

obtained by ring opening addition of (4-oxiranylmethoxy-phenyl)-phenyl-methanone (1 eq) and 1,2-epoxybutane (1eq) to hydrolyzed 3-(trimethoxysilyl)-1-propanamine 26.a) 3-(Trimethoxysilyl)-1-propanamine (97%; 7.4 g, 0.04 mol) is slowly added to stirred n-propanol (60 ml) containing water (6.6 ml, 0.37 mol). The mixture is brought to 60° C. and stirring continued for 20 hours. The solution is carefully concentrated on a rotary evaporator such as to avoid gelling, re-dissolved in n-propanol (20 ml) and re-concentrated.

26.b) The concentrated solution is diluted with n-propanol (50 ml) followed by addition of (4-oxiranylmethoxy-phenyl)-phenyl-methanone (95%; 10.7 g, 0.04 mol). The mixture is brought to 80° C. and stirred for 2.5 hours, the course of the reaction being monitored by GLC. 1,2-Epoxybutane (2.88 g, 0.04 mol) is added and the solution stirred at 80° C. for 20 hours to afford a dispersion (57.1 g). A sample is withdrawn, evaporated to dryness and characterized by GPC.

GPC (polystyrene calibrated; RI detector, THF), $M_n/M_w$/PDI (% area): 2'754/3'200/1.16 (87.5).

Tripropylene glycol diacrylate (3.85 g) is then added to the dispersion (ca. 55 g) and volatiles removed using a rotary evaporator to afford a slightly yellow resin (21.8 g).

The photoinitiator concentration as determined by weight is equivalent to 38.9% w/w (4-methoxy-phenyl)-phenyl-methanone.

Example 27

Similar to example 23, except that 2-butoxymethyl-oxirane is replaced by 1,2-epoxybutane. Mixture of polyhedral oligomeric silsesquioxanes containing silicon compounds of formula (1) in which n=6, 8, 10, 12 and A is

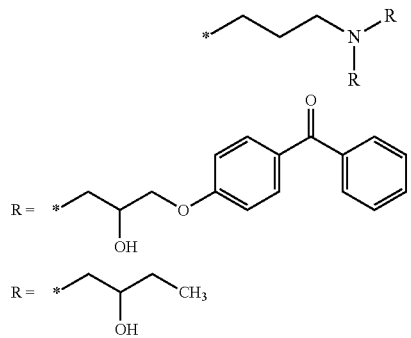

obtained by ring opening addition of (4-oxiranylmethoxy-phenyl)-phenyl-methanone (1.5 eq) and 1,2-epoxybutane (0.5 eq) to hydrolyzed 3-(trimethoxysilyl)-1-propanamine 27.a) 3-(Trimethoxysilyl)-1-propanamine (97%; 3.7 g, 0.02 mol) is slowly added to stirred n-propanol (32 ml) containing water (3.6 ml, 0.2 mol). The mixture is brought to 60° C. and stirring continued for 20 hours. The solution is carefully concentrated on a rotary evaporator such as to avoid gelling, re-dissolved in n-propanol (15 ml) and re-concentrated.

27.b) The concentrated solution is diluted with n-propanol (32 ml) followed by addition of (4-oxiranylmethoxy-phenyl)-phenyl-methanone (96%; 7.94 g, 0.03 mol). The mixture is brought to 80° C. and stirred for 2.5 hours, the course of the reaction being monitored by GLC. 1,2-Epoxybutane (1 g, 0.014 mol) is added and the solution stirred at 80° C. overnight to afford a milky dispersion. Volatiles are then removed using a rotary evaporator to afford a slightly yellow resin (12.6 g).

The photoinitiator concentration as determined by weight is equivalent to 50.5% w/w (4-methoxy-phenyl)-phenyl-methanone.

GPC (polystyrene calibrated; RI detector, THF), $M_n/M_w$/PDI (% area): 4'086/4'572/1.12 (100).

The product (12.6 g) is mixed with Sartomer SR344 (ca. 2.2 g) using chloroform as auxiliary solvent to afford, after removal of the solvent, a reduced viscosity-sample (ca. 14.8 g).

The photoinitiator concentration as determined by weight is equivalent to 43% w/w (4-methoxy-phenyl)-phenyl-methanone.

Example 28

Similar to example 26, except that 1,2-epoxybutane is replaced by 4-oxiranylmethyl-morpholine and 2-butoxymethyl-oxirane.

Mixture of polyhedral oligomeric silsesquioxanes containing silicon compounds of formula (1) in which n=6, 8, 10, 12 and A is

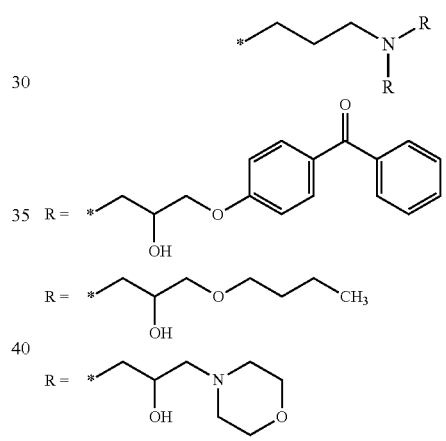

obtained by ring opening addition of (4-oxiranylmethoxy-phenyl)-phenyl-methanone (1 eq), 4-oxiranylmethyl-morpholine (0.8 eq) and 2-butoxymethyl-oxirane (0.2 eq) to hydrolyzed 3-(trimethoxysilyl)-1-propanamine 28.a) 3-(Trimethoxysilyl)-1-propanamine (97%; 1.85 g, 0.01 mol) is slowly added to stirred n-propanol (16 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (15 ml) and re-concentrated.

28.b) The concentrated solution is diluted with n-propanol (16 ml) followed by addition of (4-oxiranylmethoxy-phenyl)-phenyl-methanone (96%; 2.65 g, 0.01 mol). The mixture is brought to 60° C. and stirred for one hour, the course of the reaction being monitored by GLC. 4-Oxiranylmethyl-morpholine (98%; 1.17 g, 0.008 mol) is added and the solution stirred at 60° C. for 2.5 hours. 2-Butoxymethyl-oxirane (95%; 0.27 g, 0.002 mol) is then added and the reaction mixture stirred at 60° C. overnight. Volatiles are now removed using a rotary evaporator to afford a slightly yellow resin (5.2 g).

The photoinitiator concentration as determined by weight is equivalent to 40.8% w/w (4-methoxy-phenyl)-phenyl-methanone.

GPC (polystyrene calibrated; RI detector, THF), $M_n/M_w$/PDI (% area): 2'937/3'237/1.10 (84.4).

The product (5.2 g) is mixed with tripropylene glycol diacrylate (1 g) using 1,4-dioxane (20 ml) as auxiliary solvent to afford, after removal of the solvent, a reduced viscosity-sample (5.4 g). The photoinitiator concentration as determined by weight is equivalent to 39.3% w/w (4-methoxy-phenyl)-phenyl-methanone.

Example 29

Similar to example 26, except that 1,2-epoxybutane is replaced by acrylic acid 2-dimethylamino-ethyl ester and acrylic acid methyl ester.

Mixture of polyhedral oligomeric silsesquioxanes containing silicon compounds of formula (1) in which n=6, 8, 10, 12 and A is

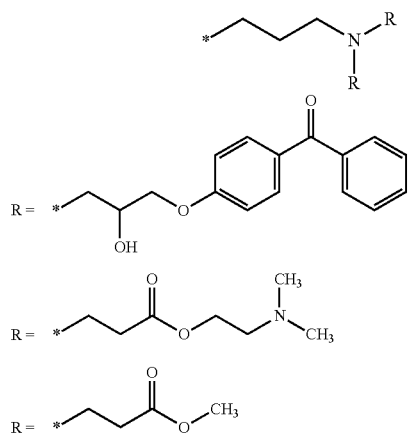

obtained by ring opening addition of (4-oxiranylmethoxy-phenyl)-phenyl-methanone (1 eq) and by Michael addition of acrylic acid 2-dimethylamino-ethyl ester (1 eq) to hydrolyzed 3-(trimethoxysilyl)-1-propanamine followed by post-treatment with (excess) acrylic acid methyl ester to ensure N-alkylation is complete.

29.a) 3-(Trimethoxysilyl)-1-propanamine (97%; 1.85 g, 0.01 mol) is slowly added to stirred ethanol (16 ml) containing water (1.8 ml, 0.1 mol). The mixture is brought to 60° C. and stirring continued for 20 hours. The solution is carefully concentrated on a rotary evaporator such as to avoid gelling, re-dissolved in ethanol (15 ml) and re-concentrated.

29.b) The concentrated solution is diluted with ethanol (20 ml) followed by addition of (4-oxiranylmethoxy-phenyl)-phenyl-methanone (96%; 2.65 g, 0.01 mol). The mixture is brought to 60° C. and stirred for 1.5 hours, the course of the reaction being monitored by GLC. 1,4-Dioxane (3 ml) is added and stirring continued for one hour. More 1,4-dioxane (20 ml) is added and the resulting solution concentrated such as to distill off the ethanol. Acrylic acid 2-dimethylamino-ethyl ester (98%; 1.46 g, 0.01 mol) is added and the solution stirred at 60° C. overnight. Acrylic acid methyl ester (2.06 g, 0.024 mol) is then added and stirring continued for 3 days at 60° C. and for one day at 80° C. Volatiles are now removed using a rotary evaporator to afford a slightly yellow resin (4.7 g).

The photoinitiator concentration as determined by weight is equivalent to 45.2% w/w (4-methoxy-phenyl)-phenyl-methanone.

GPC (polystyrene calibrated; RI detector, THF), $M_n/M_w$/PDI (% area): 4'142/6'582/1.59 (93.9).

The product (4.7 g) is mixed with tripropylene glycol diacrylate (1 g) using 1,4-dioxane (20 ml) as auxiliary solvent to afford, after removal of the solvent, a reduced viscosity-sample (5.35 g).

The photoinitiator concentration as determined by weight is equivalent to 39.7% w/w (4-methoxy-phenyl)-phenyl-methanone.

Example 30

Similar to example 23, except that 2-butoxymethyl-oxirane is replaced by 2-allyloxymethyl-oxirane and 1,2-epoxybutane.

Mixture of polyhedral oligomeric silsesquioxanes containing silicon compounds of formula (1) in which n=6, 8, 10, 12 and A is

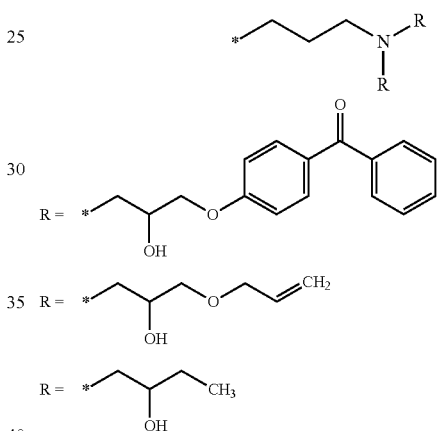

obtained by ring opening addition of (4-oxiranylmethoxy-phenyl)-phenyl-methanone (1.5 eq), 2-allyloxymethyl-oxirane (0.4 eq) and 1,2-epoxybutane (0.1 eq) to hydrolyzed 3-(trimethoxysilyl)-1-propanamine.

30.a) 3-(Trimethoxysilyl)-1-propanamine (97%; 3.68 g, 0.02 mol) is slowly added to stirred n-propanol (30 ml) containing water (3.6 ml, 0.2 mol). The mixture is brought to 60° C. and stirring continued for 20 hours. The solution is carefully concentrated on a rotary evaporator such as to avoid gelling, re-dissolved in n-propanol (15 ml) and re-concentrated.

30.b) The concentrated solution is diluted with n-propanol (30 ml) followed by addition of (4-oxiranylmethoxy-phenyl)-phenyl-methanone (96%; 7.94 g, 0.03 mol). The mixture is brought to 80° C. and stirred for 5 hours, the course of the reaction being monitored by GLC. 2-Allyloxymethyl-oxirane (97%; 0.94 g, 0.008 mol) is added and the milky dispersion stirred at 80° C. overnight. 1,2-Epoxybutane (0.43 g, 0.006 mol) is then added and stirring continued for 4 hours at 60° C. Volatiles are now removed using a rotary evaporator to afford a slightly yellow resin (11.5 g).

The photoinitiator concentration as determined by weight is equivalent to 55.3% w/w (4-methoxy-phenyl)-phenyl-methanone.

GPC (polystyrene calibrated; RI detector, THF), $M_n/M_w$/PDI (% area): 3'820/4'473/1.17 (88.6).

An aliquot (3.33 g) is mixed with Sartomer SR344 (0.79 g) and IRGASTAB® UV22 (0.04 g) using chloroform as auxiliary solvent to afford, after removal of the solvent, a reduced viscosity-sample (4.2 g).

The photoinitiator concentration as determined by weight is equivalent to 43.9% w/w (4-methoxy-phenyl)-phenyl-methanone.

Example 31

Similar to example 30, except that Sartomer SR344 (0.79 g) and IRGASTAB® UV22 are added to the crude reaction mixture prior to and followed by solvent evaporation.

Mixture of polyhedral oligomeric silsesquioxanes containing silicon compounds of formula (1) in which n=6, 8, 10, 12 and A is

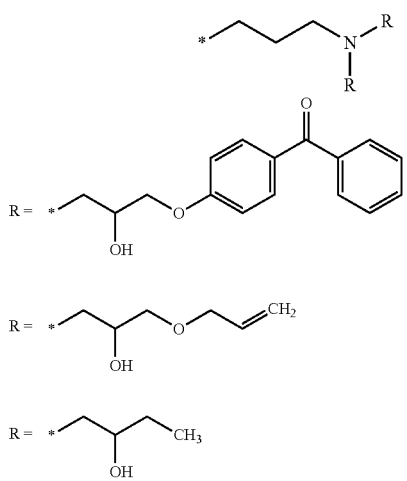

obtained by ring opening addition of (4-oxiranylmethoxy-phenyl)-phenyl-methanone (1.5 eq), 2-allyloxymethyl-oxirane (0.4 eq) and 1,2-epoxybutane (0.1 eq) to hydrolyzed 3-(trimethoxysilyl)-1-propanamine.

31.a) 3-(Trimethoxysilyl)-1-propanamine (97%; 1.84 g, 0.01 mol) is slowly added to stirred n-propanol (15 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (15 ml) and re-concentrated.

31.b) The concentrated solution is diluted with n-propanol (15 ml) followed by addition of (4-oxiranylmethoxy-phenyl)-phenyl-methanone (96%; 3.97 g, 0.015 mol). The mixture is brought to 80° C. and stirred for 7 hours, the course of the reaction being monitored by GLC. 2-Allyloxymethyl-oxirane (97%; 0.47 g, 0.004 mol) is added and the milky dispersion stirred at 80° C. overnight. 1,2-Epoxybutane (0.22 g, 0.003 mol) is then added and stirring continued for 4 hours at 60° C. A sample is withdrawn, evaporated to dryness and analyzed by GPC. GPC (polystyrene calibrated; RI detector, THF), $M_n/M_w$/PDI (% area): 3'747/4'639/1.24 (85.3).

After addition of Sartomer SR344 (1.36 g) and Irgastab UV22 (0.07 g) to the residual reaction mixture volatiles are removed using a rotary evaporator to afford a slightly yellow resin (7.05 g).

The photoinitiator concentration as determined by weight is equivalent to 45.1% w/w (4-methoxy-phenyl)-phenyl-methanone.

Example 32

Similar to example 31, except prepared at larger scale.

Mixture of polyhedral oligomeric silsesquioxanes containing silicon compounds of formula (1) in which n=6, 8, 10, 12 and A is

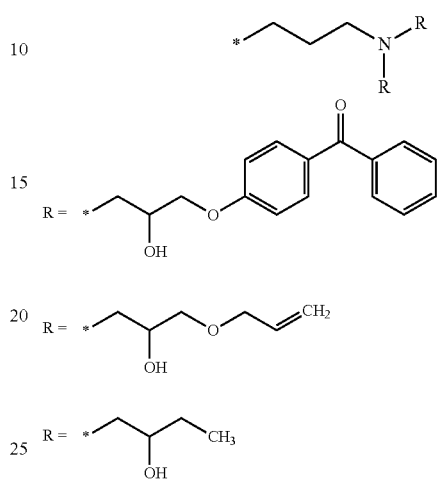

obtained by ring opening addition of (4-oxiranylmethoxy-phenyl)-phenyl-methanone (1.5 eq), 2-allyloxymethyl-oxirane (0.4 eq) and 1,2-epoxybutane (0.1 eq) to hydrolyzed 3-(trimethoxysilyl)-1-propanamine.

32.a) 3-(Trimethoxysilyl)-1-propanamine (97%; 31.4 g, 0.17 mol) is slowly added to stirred n-propanol (250 ml) containing water (30 ml, 1.7 mol). The mixture is brought to 60° C. and stirring continued for 17 hours. The solution is carefully concentrated on a rotary evaporator such as to avoid gelling, re-dissolved in n-propanol (100 ml) and re-concentrated.

32.b) The concentrated solution is diluted with n-propanol (250 ml) followed by addition of (4-oxiranylmethoxy-phenyl)-phenyl-methanone (96%; 67.5 g, 0.255 mol). The mixture is brought to 65° C. and stirred until epoxide conversion is complete (6 hours), the course of the reaction being monitored by GLC. 2-Allyloxymethyl-oxirane (97%; 8 g, 0.068 mol) is added and the milky dispersion stirred at 65° C. for 24 hours. 1,2-Epoxybutane (3.6 g, 0.05 mol) is then added and stirring continued for 16 hours at 65° C. A small sample is withdrawn, evaporated to dryness and characterized by GPC and HPLC.

GPC (polystyrene calibrated; RI detector, THF), $M_n/M_w$/PDI (% area): 3'646/4'252/1.17 (84).

HPLC (UV detector; column RP-C18, gradient methanol/THF, 0.5% trifluoroacetic acid), % area: 87.

After addition of Sartomer SR344 (23.5 g) and IRGASTAB® UV22 (1.2 g) to the reaction mixture volatiles are removed using a rotary evaporator to afford a slightly yellow resin (115.3 g). The photoinitiator concentration as determined by weight is equivalent to 46.9% w/w (4-methoxy-phenyl)-phenyl-methanone.

Example 33

Same as example 32, except that high purity (4-oxiranyl-methoxy-phenyl)-phenyl-methanone (99% area by HPLC) and 2-allyloxymethyl-oxirane (99% area by GLC) are used instead. Mixture of polyhedral oligomeric silsesquioxanes containing silicon compounds of formula (1) in which n=6, 8, 10, 12 and A is

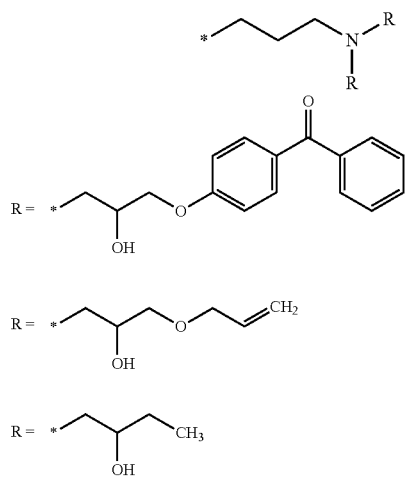

obtained by ring opening addition of (4-oxiranylmethoxy-phenyl)-phenyl-methanone (1.5 eq), 2-allyloxymethyl-oxirane (0.4 eq) and 1,2-epoxybutane (0.1 eq) to hydrolyzed 3-(trimethoxysilyl)-1-propanamine.

HPLC (UV detector; column RP-C18, gradient methanol/THF, 0.5% trifluoroacetic acid), % area: 95.

Example 34

Similar to example 30, except that (4-oxiranylmethoxy-phenyl)-phenyl-methanone is replaced by (4-chloro-phenyl)-(4-oxiranylmethoxy-phenyl)-methanone.

Mixture of polyhedral oligomeric silsesquioxanes containing silicon compounds of formula (1) in which n=6, 8, 10, 12 and A is

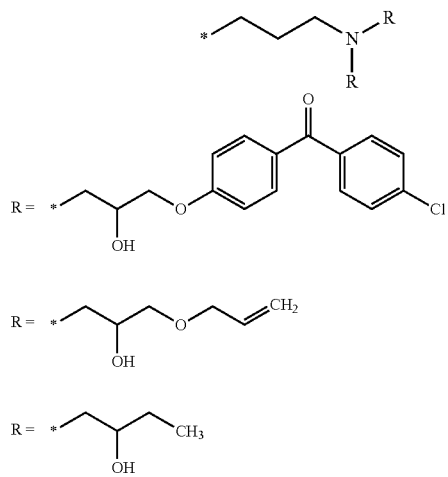

obtained by ring opening addition of (4-chloro-phenyl)-(4-oxiranylmethoxy-phenyl)methanone (1.5 eq), 2-allyloxymethyl-oxirane (0.4 eq) and 1,2-epoxybutane (0.1 eq) to hydrolyzed 3-(trimethoxysilyl)-1-propanamine.

34.a) 3-(Trimethoxysilyl)-1-propanamine (97%; 1.84 g, 0.01 mol) is slowly added to stirred n-propanol (15 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (15 ml) and re-concentrated.

34.b) The concentrated solution is diluted with n-propanol (15 ml) followed by addition of (4-chloro-phenyl)-(4-oxiranylmethoxy-phenyl)-methanone (98%; 4.4 g, 0.015 mol). The mixture is brought to 80° C. and stirred for 4 hours, the course of the reaction being monitored by GLC. 2-Allyloxymethyl-oxirane (97%; 0.47 g, 0.004 mol) is added and the dispersion stirred at 80° C. overnight. 1,2-Epoxybutane (0.22 g, 0.003 mol) is then added and stirring continued for 4 hours at 60° C. Volatiles are now removed using a rotary evaporator to afford a slightly yellow resin (5.7 g).

The photoinitiator concentration as determined by weight is equivalent to 64.6% w/w (4-chloro-phenyl)-(4-methoxy-phenyl)-methanone.

GPC (polystyrene calibrated; RI detector, THF), $M_n/M_w$/PDI (% area): 4'504/7'061/1.57 (93).

An aliquot (2.3 g) is mixed with Sartomer SR344 (0.58 g) and IRGASTAB® UV22 (0.03 g) using chloroform as auxiliary solvent to afford, after removal of the solvent, a reduced viscosity-sample (3 g).

The photoinitiator concentration as determined by weight is equivalent to 49.6% w/w (4-chloro-phenyl)-(4-methoxy-phenyl)-methanone.

Example 35

Mixture of polyhedral oligomeric silsesquioxanes containing silicon compounds of formula (1) in which n=6, 8, 10, 12 and A is

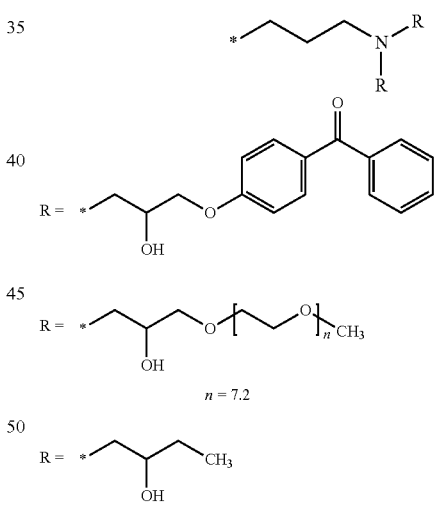

obtained by ring opening addition of (4-oxiranylmethoxy-phenyl)-phenyl-methanone (1.74 eq), MPEG 350 glycidyl ether (0.16 eq) and 1,2-epoxybutane (0.1 eq) to hydrolyzed 3-(trimethoxysilyl)-1-propanamine.

35.a) 3-(Trimethoxysilyl)-1-propanamine (97%; 3.7 g, 0.02 mol) is slowly added to stirred n-propanol (32 ml) containing water (3.6 ml, 0.2 mol). The mixture is brought to 60° C. and stirring continued for 20 hours. The solution is carefully concentrated on a rotary evaporator such as to avoid gelling, re-dissolved in n-propanol (15 ml) and re-concentrated.

35.b) The concentrated solution is diluted with n-propanol (32 ml) followed by addition of (4-oxiranylmethoxy-phenyl)- phenyl-methanone (96%; 8.9 g, 0.034 mol). The mixture is brought to 80° C. and stirred for 2.5 hours, the course of the reaction being monitored by GLC. MPEG 350 glycidyl ether (2.25 meq epoxide/g; 1.45 g, 0.003 mol epoxide) is added and the dispersion stirred at 80° C. overnight. 1,2-Epoxybutane (0.29 g, 0.004 mol) is then added and stirring continued for 4 hours at 60° C. Volatiles are now removed using a rotary evaporator to afford a slightly yellow resin (12.9 g).

The photoinitiator concentration as determined by weight is equivalent to 55.3% w/w (4-methoxy-phenyl)-phenyl-methanone.

GPC (polystyrene calibrated; RI detector, THF), $M_n/M_w$/PDI (% area): 5'015/5'810/1.16 (100).

Example 36

Mixture of polyhedral oligomeric silsesquioxanes containing silicon compounds of formula (1) in which n=6, 8, 10, 12 and A is

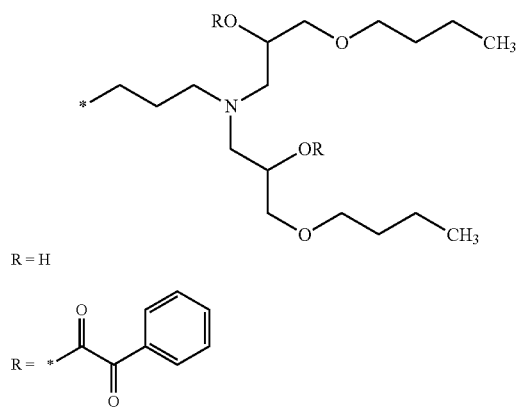

obtained by ring opening addition of 2-butoxymethyl-oxirane (2 eq) to hydrolyzed 3-(trimethoxysilyl)-1-propanamine followed by esterification with oxo-phenyl-acetyl chloride (2 eq).

36.a) 3-(Trimethoxysilyl)-1-propanamine (97%; 55.4 g, 0.3 mol) is slowly added to stirred ethanol (470 ml) containing water (53 ml, 2.94 mol). The mixture is brought to 50° C. and stirring continued for 20 hours. The solution is carefully concentrated on a rotary evaporator such as to avoid gelling, re-dissolved in ethanol (100 ml) and re-concentrated according to example 6a.

36.b) The concentrated solution is diluted with ethanol (90 ml) followed by slow addition of 2-butoxymethyl-oxirane (95%; 82.2 g, 0.6 mol). The mixture is brought to 50° C. and stirred overnight, the course of the reaction being monitored by GLC. The reaction mixture is then cooled down to afford a clear solution (209.5 g).

The solid content of the dispersion, obtained by evaporation of the solvent, is 52.8%; elemental analysis (%). found C, 54.78; H, 11.53; N, 3.76 (combustion), N 3.75 (perchloric acid titration of acetic anhydride-treated sample; indicative of tertiary amine nitrogen); thermogravimetric analysis (TGA; % residue). found 18.0.

$^{29}$Si NMR: T3; GPC (polystyrene calibrated; RI detector, THF), $M_n$ (n)/$M_w$/polydispersity index PDI (% area): 2'695 (7.3)/3'022/1.12 (86.6).

36.c) An aliquot (7.05 g, 0.01 mol N) is evaporated to dryness using a rotary evaporator and the residue re-dissolved in dichloromethane (20 ml) followed by sequential addition of triethylamine (2.02 g, 0.02 mol) and a solution of oxo-phenyl-acetyl chloride previously prepared in situ by stirring oxo-phenyl-acetic acid (3.75 g, 0.025 mol), oxalyl chloride (3.55 g, 0.028 mol) and a few drops of N,N-dimethylformamide in dichloromethane (10 ml) for two hours at 25° C. The resulting reaction mixture is kept stirring overnight at 25° C., poured onto water saturated with sodium hydrogen carbonate (50 ml) and the mixture kept stirring one hour at 25° C. The organic phase is separated off, brine-washed and evaporated to afford a slightly brownish viscous oil (5 g).

$^1$H NMR (CDCl$_3$): the ratio Si/(grafted) phenylglyoxylate is 1/1.6 (mol/mol), corresponding to a photoinitiator concentration equivalent to 52.5% w/w oxo-phenyl-acetic acid methyl ester (DAROCUR® MBF).

GPC (polystyrene calibrated; RI detector, THF), $M_n/M_w$/PDI (% area): 3'070/3'754/1.22 (67.8).

An aliquot (4.55 g) is mixed with Sartomer SR344 (1.13 g) and IRGASTAB® UV22 (0.05 g) using dichloromethane as auxiliary solvent to afford, after removal of the solvent, a reduced viscosity-sample (5.7 g).

The photoinitiator concentration is equivalent to 41.9% w/w oxo-phenyl-acetic acid methyl ester (DAROCUR® MBF).

Example 37

Mixture of polyhedral oligomeric silsesquioxanes containing silicon compounds of formula (1) in which n 10=and A is

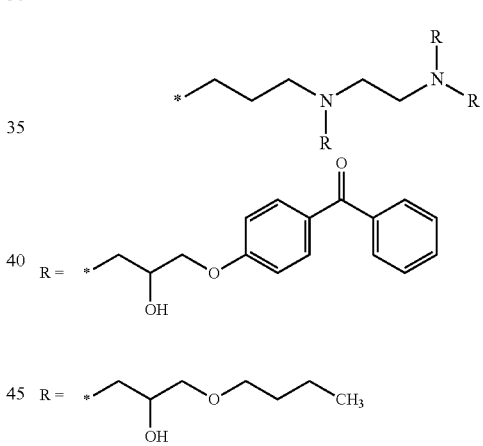

obtained by ring opening addition of (4-oxiranylmethoxy-phenyl)-phenyl-methanone (2 eq) and 2-butoxymethyl-oxirane (leg) to hydrolyzed N[3-(trimethoxysilyl)propyl]-1,2-ethanediamine.

37.a) N[3-(Trimethoxysilyl)propyl]-1,2-ethanediamine (98%; 2.27 g, 0.01 mol) is slowly added to stirred n-propanol (16 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (20 ml) and re-concentrated.

$^{29}$Si NMR: T3; MS (pos. MALDI), m/z (%): distribution curve ranging from 1'100 (ca) to 2'100 (ca) with a broad maximum at 1'600 (ca); found 1'532.3 (90). calcd. 1'530 ($C_{50}H_{130}N_{20}O_{15}Si_{10}$; $T_{10}$-($CH_2CH_2CH_2NHCH_2CH_2NH_2$)$_{10}$).

37.b) The concentrated solution is diluted with n-propanol (20 ml) followed by addition of (4-oxiranylmethoxy-phenyl)-phenyl-methanone (95%; 5.3 g, 0.02 mol). The mixture is brought to 80° C. and stirred for 17 hours, the course of the reaction being monitored by GLC. 2-Butoxymethyl-oxirane (95%; 1.37 g, 0.01 mol) is added and the mixture stirred another 20 hours at 80° C. Volatiles are then removed using a rotary evaporator to afford a slightly yellow resin (8.1 g).

The photoinitiator concentration as determined by weight is equivalent to 51.9% w/w (4-methoxy-phenyl)-phenyl-methanone.

GPC (polystyrene calibrated; RI detector, THF), $M_n/M_w$/PDI (% area): 4'177/5'052/1.21 (82).

The product (8.1 g) is mixed with tripropylene glycol diacrylate (1.8 g) using 1,4-dioxane as auxiliary solvent to afford, after removal of the solvent, a reduced viscosity-sample (9.3 g).

The photoinitiator concentration as determined by weight is equivalent to 45.2% w/w (4-methoxy-phenyl)-phenyl-methanone.

Example 38

Mixture of polyhedral oligomeric silsesquioxanes containing silicon compounds of formula (1) in which n=10 and A is

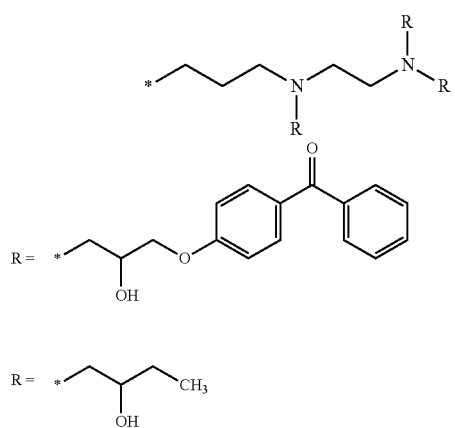

obtained by ring opening addition of (4-oxiranylmethoxy-phenyl)-phenyl-methanone (0.5 eq) and 1,2-epoxybutane (2.5 eq) to hydrolyzed N[3-(trimethoxysilyl)propyl]-1,2-ethanediamine.

38.a) N[3-(Trimethoxysilyl)propyl]-1,2-ethanediamine (98%; 6.8 g, 0.03 mol) is slowly added to stirred n-propanol (47 ml) containing water (5.3 ml, 0.29 mol). The mixture is brought to 60° C. and stirring continued for 20 hours. The solution is carefully concentrated on a rotary evaporator such as to avoid gelling.

38.b) The concentrated solution is diluted with n-propanol (20 ml) followed by addition of (4-oxiranylmethoxy-phenyl)-phenyl-methanone (95%; 4.0 g, 0.015 mol). The mixture is brought to 50° C. and stirred for 3 hours, the course of the reaction being monitored by GLC. 1,2-Epoxybutane (5.4 g, 0.075 mol) is added and the mixture stirred overnight at 50° C. Volatiles are then removed using a rotary evaporator to afford a slightly yellow resin (13.95 g). The photoinitiator concentration as determined by weight is equivalent to 22.8% w/w (4-methoxy-phenyl)-phenyl-methanone.

GPC (polystyrene calibrated; RI detector, THF), $M_n/M_w$/PDI (% area): 2'049/2'715/1.33 (89.1).

The product (13.95 g) is mixed with tripropylene glycol diacrylate (3.0 g) using 1,4-dioxane as auxiliary solvent to afford, after removal of the solvent, a reduced viscosity-sample (16.15 g). The photoinitiator concentration as determined by weight is equivalent to 19.7% w/w (4-methoxy-phenyl)-phenyl-methanone.

Example 39

Mixture of polyhedral oligomeric silsesquioxanes containing silicon compounds of formula (1) in which n 10=and A is

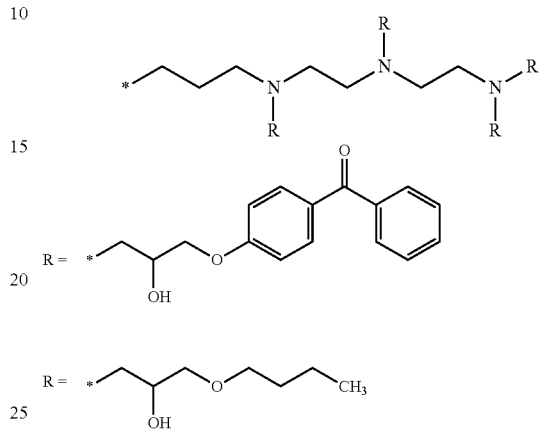

obtained by ring opening addition of (4-oxiranylmethoxy-phenyl)-phenyl-methanone (3 eq) and 2-butoxymethyl-oxirane (leg) to hydrolyzed N1-(2-aminoethyl)-N2-[3-(trimethoxysilyl)propyl]-1,2-ethanediamine.

39.a) N1-(2-aminoethyl)-N2-[3-(trimethoxysilyl)propyl]-1,2-ethanediamine (96%; 2.76 g, 0.01 mol) is slowly added to stirred n-propanol (16 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (20 ml) and re-concentrated.

$^{29}$Si NMR: T3; MS (pos. MALDI), m/z (%): distribution curve ranging from 1'200 (ca) to 2'400 (ca) with a broad maximum at 2'000 (ca); found 1'961.8 (70). calcd. 1'960 ($C_{70}H_{180}N_{30}C_{15}Si_{10}$; $T_{10}$-($CH_2CH_2CH_2NHCH_2CH_2NHCH_2CH_2NH_2)_{10}$).

39.b) The concentrated solution is diluted with n-propanol (30 ml) followed by addition of (4-oxiranylmethoxy-phenyl)-phenyl-methanone (95%; 8.0 g, 0.03 mol). The mixture is brought to 80° C. and stirred for 17 hours, the course of the reaction being monitored by GLC. 2-Butoxymethyl-oxirane (95%; 1.37 g, 0.01 mol) is added and the mixture stirred another 20 hours at 80° C. Volatiles are then removed using a rotary evaporator to afford a slightly yellow resin (8.5 g).

The photoinitiator concentration as determined by weight is equivalent to 74.6% w/w (4-methoxy-phenyl)-phenyl-methanone.

GPC (polystyrene calibrated; RI detector, THF), $M_n/M_w$/PDI (% area): 5'332/10'834/2.03 (85).

The product (8.5 g) is mixed with tripropylene glycol diacrylate (2.1 g) using 1,4-dioxane as auxiliary solvent to afford, after removal of the solvent, a reduced viscosity-sample (11.3 g). The photoinitiator concentration as determined by weight is equivalent to 56.1% w/w (4-methoxy-phenyl)-phenyl-methanone.

Example 40

Mixture of polyhedral oligomeric silsesquioxanes containing silicon compounds of formula (1) in which n=6, 8, 10, 12 and A is

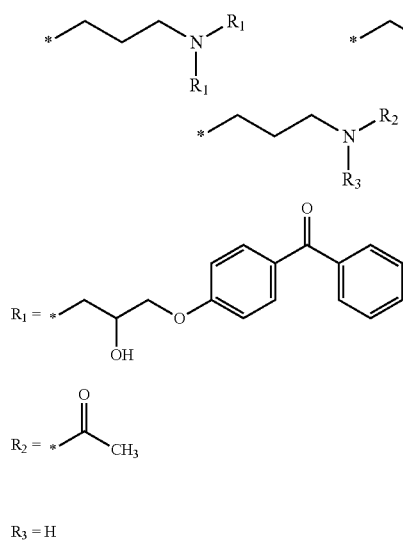

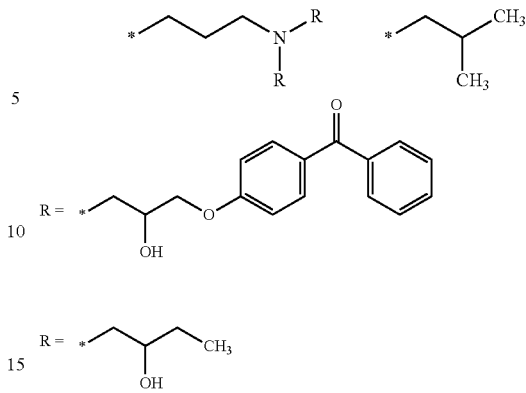

obtained by ring opening addition of (4-oxiranylmethoxy-phenyl)-phenyl-methanone (0.5 eq) to hydrolyzed 3-(tri-methoxysilyl)-1-propanamine followed by N-acetylation using acetic anhydride.

40.a) 3-(Trimethoxysilyl)-1-propanamine (97%; 5.55 g, 0.03 mol) is slowly added to stirred ethanol (44 ml) containing water (5 ml, 0.29 mol). The mixture is brought to 50° C. and stirring continued for 20 hours. The solution is carefully concentrated on a rotary evaporator such as to avoid gelling, re-dissolved in ethanol (50 ml) and re-concentrated.

40.b) The concentrated solution is diluted with ethanol (40 ml) followed by addition of (4-oxiranylmethoxy-phenyl)-phenyl-methanone (98%; 3.9 g, 0.015 mol). The mixture is brought to 50° C. and stirred for 3 hours, the course of the reaction being monitored by GLC. Acetic anhydride (4.59 g, 0.045 mol) is added and the solution stirred at 50° C. overnight. Volatiles are now removed using a rotary evaporator to afford a slightly yellow resin (10.0 g).

The photoinitiator concentration as determined by weight is equivalent to 31.9% w/w (4-methoxy-phenyl)-phenyl-methanone (1.5 meq/g).

Elemental analysis (%). found N 4.70 (by combustion; 3.35 meq/g), N 0.23 (by perchloric acid titration, indicative of tertiary amine nitrogen; 0.16 meq/g); TGA; (% residue). found 21.5.

MS (pos. MALDI), m/z: distribution curve ranging from 1'800 (ca) to 4'300 (ca) with a broad maximum at 2'800 (ca).

The resin (ca. 10 g) is dispersed in ethanol (ca. 10 g) to afford the title compound as an ethanolic dispersion (19.6 g).

The solid content of the dispersion, obtained by evaporation of the solvent, is 48.6%. The photoinitiator concentration as determined by UV-VIS/by weight is equivalent to 16.3 /15.5% w/w (4-methoxy-phenyl)-phenyl-methanone.

Example 41

Mixture of polyhedral oligomeric silsesquioxanes containing silicon compounds of formula (1) in which n=8, 10, 12 and A is obtained by ring opening addition of (4-oxiranylmethoxy-phenyl)-phenyl-methanone (0.95 eq) and 1,2-epoxybutane (0.05 eq) to a hydrolyzed mixture of 3-(trimethoxysilyl)-1-propanamine (0.5 eq) and isobutyltrimethoxysilane (0.5 eq).

41.a) 3-(Trimethoxysilyl)-1-propanamine (97%; 0.92 g, 0.005 mol) and isobutyltrimethoxysilane (97%; 0.92 g, 0.005 mol) are simultaneously and slowly added to stirred n-propanol (16 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (15 ml) and re-concentrated.

$^{29}$Si NMR: T3; MS (pos. APCI) m/z (%). found 876.5 (55), 1'087.6 (65) and 1'307.6 (85), revealing the presence of silsesquioxanes of the type ($^i$Bu)$_a$-T$_n$-(CH$_2$CH$_2$CH$_2$NH$_2$)$_{n-a}$ (n=8, 10, 12). calcd. 875 (C$_{29}$H$_{69}$N$_3$O$_{12}$Si$_8$; ($^i$Bu)$_5$-T$_8$-(CH$_2$CH$_2$CH$_2$NH$_2$)$_3$), 876 (C$_{28}$H$_{68}$N$_4$O$_{12}$Si$_8$; ($^i$Bu)$_4$-T$_8$-(CH$_2$CH$_2$CH$_2$NH$_2$)$_4$.

41.b) The concentrated solution is diluted with n-propanol (15 ml) followed by addition of (4-oxiranylmethoxy-phenyl)-phenyl-methanone (96%; 2.51 g, 0.0095 mol). The mixture is brought to reflux and stirred overnight, the course of the reaction being monitored by GLC. 1,2-Epoxybutane (0.14 g, 0.002 mol) is added and the mixture stirred another 2 hours at 50° C. Volatiles are then removed using a rotary evaporator to afford a slightly yellow resin (3.9 g). The photoinitiator concentration as determined by weight is equivalent to 51.6% w/w (4-methoxy-phenyl)-phenyl-methanone.

GPC (polystyrene calibrated; RI detector, THF), M$_n$/M$_w$/PDI (% area): 2'818/3'353/1.19 (90.4).

The product (3.9 g) is mixed with Sartomer SR344 (ca. 0.7 g) using chloroform as auxiliary solvent to afford, after removal of the solvent, a reduced viscosity-sample (4.6 g).

The photoinitiator concentration as determined by weight is equivalent to 43.7% w/w (4-methoxy-phenyl)-phenyl-methanone.

Example 42

Similar to example 30, except that the hydrolyzed 3-(trimethoxysilyl)-1-propanamine is treated with tetraethoxysilane after azeotropical removal of water and prior to N-alkylation. Mixture of polyhedral oligomeric silsesquioxanes containing silicon compounds of formula (1) in which n=8, 10, 12 and A is

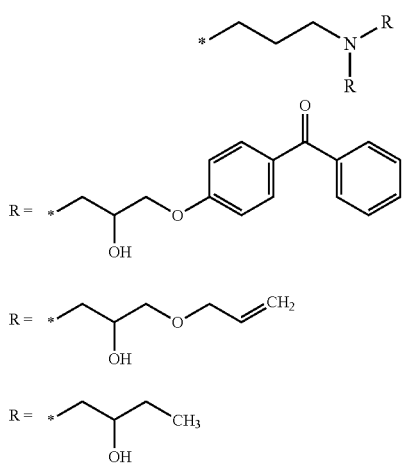

obtained by ring opening addition of (4-oxiranylmethoxy-phenyl)-phenyl-methanone (1.5 eq), 2-allyloxymethyl-oxirane (0.4 eq) and 1,2-epoxybutane (0.1 eq) to hydrolyzed 3-(trimethoxysilyl)-1-propanamine which previously has been treated with tetraethoxysilane (0.13 eq).

42.a) 3-(Trimethoxysilyl)-1-propanamine (97%; 1.85 g, 0.01 mol) is dissolved in 2-propanol (4 ml). A mixture of 2-propanol (0.5 ml) and water (0.45 ml, 0.025 mol) is slowly added, the resulting solution brought to reflux and stirred for 20 hours. The solution is carefully concentrated at ambient pressure such as to avoid gelling. 2-Propanol (4 ml) is added and the solution cooled to 35° C. Tetraethoxysilane (0.28 g, 0.0013 mol) is then added and the resulting solution refluxed for another 20 hours. The solution is now carefully concentrated at ambient pressure such as to avoid gelling and cooled to ambient temperature.

$^{29}$Si NMR: T3; MS (pos. APCI), m/z (%). found 1324.0 (5), 1102.6 (40), 881.4 (100). calcd. 1320 ($C_{36}H_{96}N_{12}O_{18}Si_{12}$; $T_{12}$-$(CH_2CH_2CH_2NH_2)_{12}$), 1100 ($C_{30}H_{80}N_{10}C_{15}Si_{10}$; $T_{10}$-$(CH_2CH_2CH_2NH_2)_{10}$), 880 ($C_{24}H_{64}N_8O_{12}Si_8$; $T_8$-$(CH_2CH_2CH_2NH_2)_8$).

42.b) The concentrated solution is diluted with 2-propanol (15 ml) followed by addition of (4-oxiranylmethoxy-phenyl)-phenyl-methanone (96%; 3.97 g, 0.015 mol). The mixture is brought to reflux and stirred for 5 hours, the course of the reaction being monitored by GLC. 2-Allyloxymethyl-oxirane (97%; 0.47 g, 0.004 mol) is added and the mixture stirred overnight at reflux. 1,2-Epoxybutane (0.22 g, 0.003 mol) is added and the mixture stirred another two hours at 60° C. Volatiles are now removed using a rotary evaporator to afford a slightly yellow resin (5.7 g).

The photoinitiator concentration as determined by weight is equivalent to 55.8% w/w (4-methoxy-phenyl)-phenyl-methanone.

GPC (polystyrene calibrated; RI detector, THF), $M_n/M_w$/PDI (% area): 2'099/4'056/1.93 (97.7).

HPLC (UV detector; column RP-C18, gradient methanol/THF, 0.5% trifluoroacetic acid), % area: 96.

An aliquot (4.6 g) is mixed with Sartomer SR344 (ca. 1.1 g) and IRGASTAB® UV22 (ca. 0.06 g) using chloroform as auxiliary solvent to afford, after removal of the solvent, a reduced viscosity-sample (5.8 g).

The photoinitiator concentration as determined by weight is equivalent to ca. 44% w/w (4-methoxy-phenyl)-phenyl-methanone.

Example 43

Mixture of polyhedral oligomeric silsesquioxanes containing silicon compounds of formula (1) in which n=8, 10, 12 and A is

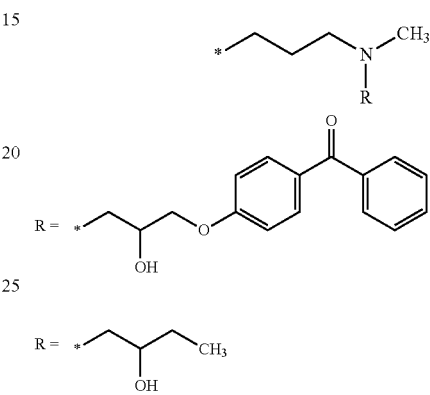

obtained by ring opening addition of (4-oxiranylmethoxy-phenyl)-phenyl-methanone (0.9 eq) and 1,2-epoxybutane (0.1 eq) to hydrolyzed N-methyl-3-(trimethoxysilyl)-1-propanamine.

43.a) N-Methyl-3-(trimethoxysilyl)-1-propanamine (97%; 1.99 g, 0.01 mol) is slowly added to stirred n-propanol (15 ml) containing water (1.8 ml, 0.1 mol). The mixture is brought to 60° C. and stirring continued for 20 hours. The solution is carefully concentrated on a rotary evaporator such as to avoid gelling, re-dissolved in n-propanol (20 ml) and re-concentrated. $^{29}$Si NMR: T3; MS (pos. MALDI), m/z. found 1'490.97, 1'242.87, 994.07. calcd. 1'488 ($C_{48}H_{120}N_{12}O_{18}Si_{12}$; $T_{12}$-$(CH_2CH_2CH_2NHCH_3)_{12}$), 1'240 ($C_{40}H_{100}N_{10}C_{15}Si_{10}$; $T_{10}$-$(CH_2CH_2CH_2NHCH_3)_{10}$), 992 ($C_{32}H_{80}N_8O_{12}Si_8$; $T_8$-$(CH_2CH_2CH_2NHCH_3)_8$); MS (pos. APCI), m/z (%): 1'490.8 (95), 1'242.7 (100), 993.6 (70).

43.b) The concentrated solution is diluted with n-propanol (13 ml) followed by addition of (4-oxiranylmethoxy-phenyl)-phenyl-methanone (95%; 2.5 g, 0.0093 mol). The mixture is brought to 70° C. and stirred for 4 hours, the course of the reaction being monitored by GLC. 1,2-Epoxybutane (0.14 g, 0.002 mol) is added and the mixture stirred another 16 hours at 70° C. Volatiles are then removed using a rotary evaporator to afford a slightly yellow resin (4.1 g). The photoinitiator concentration as determined by weight is equivalent to 48.3% w/w (4-methoxy-phenyl)-phenyl-methanone.

GPC (polystyrene calibrated; RI detector, THF), $M_n/M_w$/PDI (% area): 2'991/3'345/1.12 (73.2).

The product (4.1 g) is mixed with Sartomer SR344 (ca. 0.7 g) using chloroform as auxiliary solvent to afford, after removal of the solvent, a reduced viscosity-sample (4.8 g).

The photoinitiator concentration as determined by weight is equivalent to 41% w/w (4-methoxy-phenyl)-phenyl-methanone.

Example 44

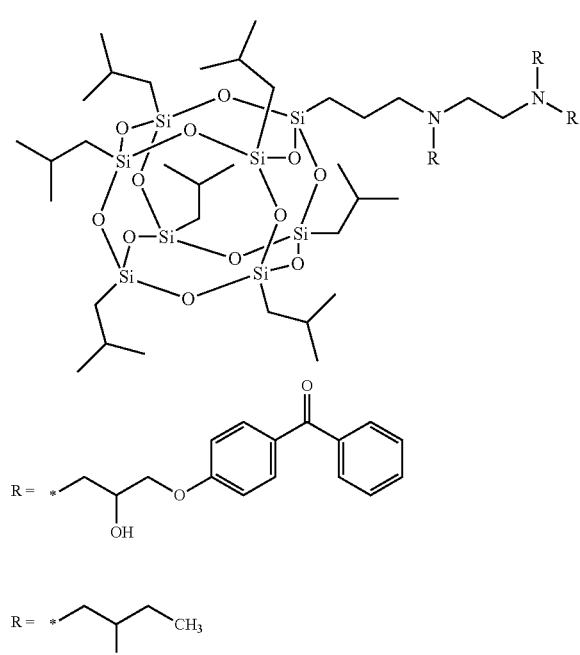

A suspension of ($^i$Bu)$_7$-T$_8$-(CH$_2$CH$_2$CH$_2$NHCH$_2$CH$_2$NH$_2$) (AM0275, 2.11 meq N/g; 0.71 g, 0.0015 mol N) and (4-oxiranylmethoxy-phenyl)-phenyl-methanone (0.53 g, 0.0021 mol) in n-propanol (12 ml) is stirred 28 hours at 80° C., the course of the reaction being monitored by GLC. After cooling down to 60° C. 1,2-epoxybutane (0.05 g, 0.0007 mol) is added and the reaction mixture stirred another 4 hours. Volatiles are now evaporated using a rotary evaporator to afford a colourless, slightly opaque waxy solid (1.2 g).

The photoinitiator concentration as determined by weight is equivalent to 36.9% w/w (4-methoxy-phenyl)-phenyl-methanone.

MS (pos. APCI), m/z (%). found 1680.7 (100), 1498.7 (5), 1426.8 (20). calcd. 1678 (C$_{81}$H$_{118}$N2O21Si$_8$; compound 15), 1496 (C$_{69}$H$_{112}$N$_2$O$_{19}$Si$_8$; product derived from addition of (4-oxiranylmethoxy-phenyl)-phenyl-methanone (2×) and 1,2-epoxybutane (1×) to ($^i$Bu)$_7$-T$_8$-(CH$_2$CH$_2$CH$_2$NHCH$_2$CH$_2$NH$_2$), 1424 (C$_{65}$H$_{104}$N$_2$O$_{18}$Si$_8$; product derived from addition of (4-oxiranylmethoxy-phenyl)-phenyl-methanone (2×) to ($^i$Bu)$_7$-T$_8$-(CH$_2$CH$_2$CH$_2$NHCH$_2$CH$_2$NH$_2$). GPC (polystyrene calibrated; RI detector, THF), M$_n$/M$_w$/PDI (% area): 1'472/1'839/1.25 (100).

An aliquot (0.95 g) is mixed with Sartomer SR344 (0.23 g) and IRGASTAB® UV22 (0.02 g) using chloroform as auxiliary solvent to afford, after removal of the solvent, a reduced viscosity-sample (1.2 g).

The photoinitiator concentration as determined by weight is equivalent to 29.2% w/w (4-methoxy-phenyl)-phenyl-methanone.

Example 45

Mixture of polyhedral oligomeric silsesquioxanes containing silicon compounds of formula (1) in which n=8, 10, 12 and A is

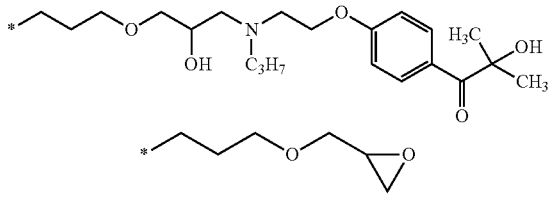

obtained by ring opening addition of Glycidyl POSS EP0409 to 2-hydroxy-2-methyl-1-[4-(2-propylamino-ethoxy)phenyl]-propan-1-one (0.5 eq per eq epoxide).

Glycidyl POSS EP0409 (1 g, 0.0059 mol epoxide) and 2-hydroxy-2-methyl-1-[4-(2-propylamino-ethoxy)-phenyl]-propan-1-one (0.78 g, 0.0029 mol) are dissolved in chloroform (15 ml) and the solution stirred at 60° C. during 20 hours. Ethanol (10 ml) is added and the resulting mixture stirred at 60° C. for another 48 hours, the course of the reaction being monitored by GLC. Volatiles are then removed using a rotary evaporator to afford a slightly yellow resin (1.78 g).

GPC (polystyrene calibrated; RI detector, THF), M$_n$/M$_w$/PDI (% area): 2'856/3'151/1.10 (64).

Example 46

Mixture of polyhedral oligomeric silsesquioxanes containing silicon compounds of formula (1) in which n=8, 10, 12 and A is

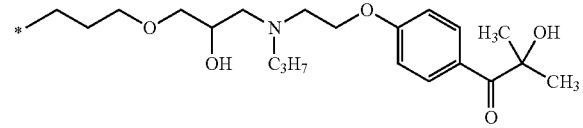

obtained by ring opening addition of Glycidyl POSS EP0409 to 2-hydroxy-2-methyl-1-[4-(2-propylamino-ethoxy)-phenyl]-propan-1-one (1eg per eq epoxide).

Glycidyl POSS EP0409 (1 g, 0.0059 mol epoxide) and 2-hydroxy-2-methyl-1-[4-(2-propylamino-ethoxy)-phenyl]-propan-1-one (1.69 g, 0.0064 mol) are dissolved in chloroform (15 ml) and the solution stirred at 60° C. during 20 hours. Ethanol (10 ml) is added and the resulting mixture stirred at 60° C. for another 48 hours, the course of the reaction being monitored by GLC. Volatiles are then removed using a rotary evaporator to afford a slightly yellow resin (2.4 g).

GPC (polystyrene calibrated; RI detector, THF), M$_n$/M$_w$/PDI (% area): 3'472/4'001/1.15 (63).

Example 47

Mixture of polyhedral oligomeric silsesquioxanes containing silicon compounds of formula (1) in which n=8, 10, 12 and A is

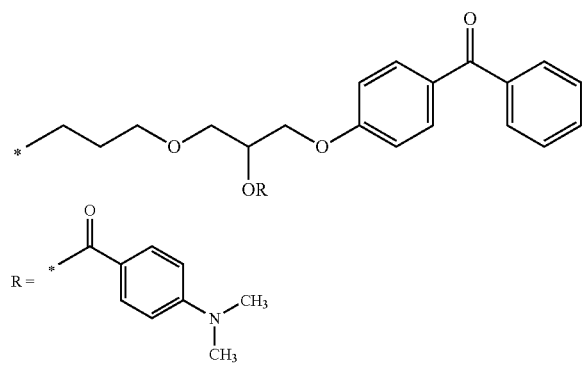

R =

R = H

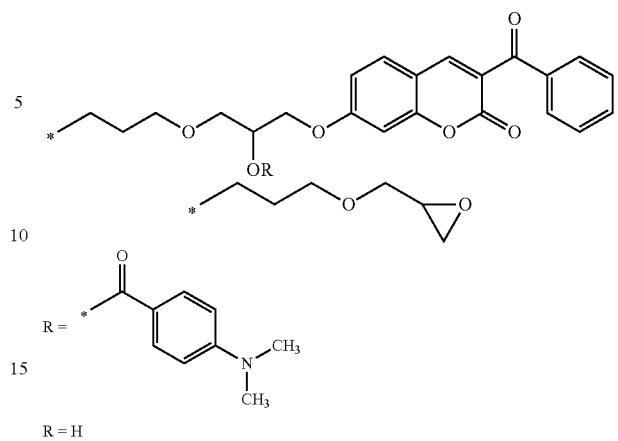

R =

R = H obtained by ring opening addition of Glycidyl POSS EP0409 to (4-hydroxy-phenyl)-phenyl-methanone (1 eq per eq epoxide) followed by esterification with 4-dimethylamino-benzoyl chloride (1 eq).

47.a) Glycidyl POSS EP0409 (1 g, 0.0059 mol epoxide) is dissolved in toluene (15 ml) followed by the addition of (4-hydroxy-phenyl)-phenyl-methanone (designated benzophenone; 1.26 g, 0.0064 mol) and benzyl-trimethyl-ammonium chloride (0.06 g, 0.0003 mol). The mixture is brought to 100° C. and stirred for 18 hours, the course of the reaction being monitored by GLC. The mixture is cooled down to 25° C. and volatiles removed using a rotary evaporator. The residue is dissolved in dichloromethane and the solution washed with aqueous NaOH (1 mol/L) and brine. The organic phase is separated off and the solvent distilled off to afford a colourless resin (1 g).

$^1$H NMR (CDCl$_3$): the ratio Si/(grafted) benzophenone is 1/0.91 (mol/mol). GPC (polystyrene calibrated; RI detector, THF), $M_n$/$M_w$/PDI (% area): 2'815/3'047/1.08 (67.4), 6'185/6'580/1.06 (32.6).

47.b) The resin (0.95 g. calcd. 2.7 meq OH/g, 0.0026 mol OH) and triethylamine (0.29 g, 0.0029 mol) are dissolved in dichloromethane (10 ml) followed by the addition of a suspension of 4-dimethylamino-benzoyl chloride (97%; 0.54 g, 0.0029 mol) in dichloromethane (3 ml). The mixture is stirred for 20 hours at 25° C. and then successively washed with aqueous solutions of NaHCO$_3$ (saturated), Na$_2$CO$_3$ (2 mol/L), NaOH (1 mol/L), HCl (1 mol/L), NaOH (1 mol/L) and brine to afford, after distilling off the solvent, a colorless resin (0.35 g).

$^1$H NMR (DMSO-d$_6$): the ratio Si/(grafted) benzophenone/(grafted) 4-dimethylamino-benzoate is 1/0.93/0.58 (mol/mol/mol).

GPC (polystyrene calibrated; RI detector, THF), $M_n$/$M_w$/PDI (% area): 3'484/3'755/1.08 (52.4), 7'494/7'932/1.06 (22.3).

Example 48

Mixture of polyhedral oligomeric silsesquioxanes containing silicon compounds of formula (1) in which n=8, 10, 12 and A is obtained by ring opening addition of Glycidyl POSS EP0409 to 3-benzoyl-7-hydroxy-1-benzopyran-2-one (1 eq per eq epoxide) followed by esterification with 4-dimethylamino-benzoyl chloride (1 eq).

48.a) A mixture of Glycidyl POSS EP0409 (1 g, 0.0059 mol epoxide), benzyl-trimethyl-ammonium chloride (0.06 g, 0.0003 mol), 3-benzoyl-7-hydroxy-1-benzopyran-2-one (designated ketocoumarin; 1.7 g, 0.0064 mol) and toluene (15 ml) is brought to 100° C. and stirred for 20 hours. The mixture is cooled down to 25° C. and concentrated on a rotary evaporator. The residue (2.5 g) is dissolved in dichloromethane (20 ml) and the solution successively washed with aqueous NaOH (1 mol/L) and brine. The organic phase is separated off and the solvent distilled off to afford an orange resin (0.5 g).

$^1$H NMR (DMSO-d$_6$): the ratio Si/epoxide/(grafted) ketocoumarin is 1/0.58/0.26 (mol /mol/mol).

GPC (polystyrene calibrated; RI detector, THF), $M_n$/$M_w$/PDI (% area): 2'842/3'646/1.28 (100).

48.b) The resin (0.38 g. calcd. 1.2 meq OH/g, 0.00046 mol OH) and triethylamine (0.05 g, 0.00049 mol) are dissolved in dichloromethane (10 ml) followed by the addition of 4-dimethylamino-benzoyl chloride (97%; 0.095 g, 0.0005 mol). The mixture is stirred for 20 hours at 25° C. and then successively washed with aqueous solutions of NaOH (1 mol/L) and brine to afford, after distilling off the solvent, a colorless resin (0.4 g).

$^1$H NMR (DMSO-d$_6$): the ratio Si/epoxide/(grafted) ketocoumarin/(grafted) 4-dimethylamino-benzoate is 1/0.52/0.26/0.21 (mol/mol/mol/mol).

GPC (polystyrene calibrated; RI detector, THF), $M_n$/$M_w$/PDI (% area): 2'957/3'517/1.19 (70.3).

Example 49

Similar as example 48, except that in the first step toluene is replaced by 1,4-dioxane.

Mixture of polyhedral oligomeric silsesquioxanes containing silicon compounds of formula (1) in which n=8, 10, 12 and A is

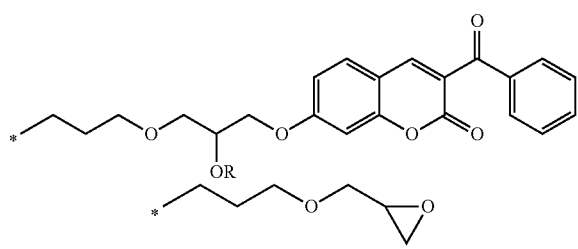

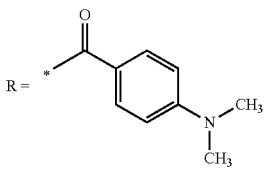

R = H obtained by ring opening addition of Glycidyl POSS EP0409 to 3-benzoyl-7-hydroxy-1-benzopyran-2-one (1 eq per eq epoxide) followed by esterification with 4-dimethylamino-benzoyl chloride (1 eq).

49.a) A mixture of Glycidyl POSS EP0409 (2 g, 0.0117 mol epoxide), benzyl-trimethyl-ammonium chloride (0.12 g, 0.0006 mol), 3-benzoyl-7-hydroxy-1-benzopyran-2-one (designated ketocoumarin; 3.4 g, 0.0128 mol) and 1,4-dioxane (40 ml) is brought to 100° C. and stirred for 20 hours. The mixture is cooled down to 25° C. and concentrated on a rotary evaporator. The residue (6.15 g) is dissolved in dichloromethane (80 ml) and the solution successively washed with aqueous NaOH (1 mol/L) and brine. The organic phase is separated off and the solvent distilled off to afford an orange resin (1.1 g).

$^1$H NMR (DMSO-d$_6$): the ratio Si/epoxide/(grafted) ketocoumarin is 1/0.24/0.56 (mol /mol/mol).

GPC (polystyrene calibrated; RI detector, THF), M$_n$/M$_w$/PDI (% area): 2'948/3'255/1.10 (100).

49.b) The resin (1 g. calcd. 2.8 meq OH/g, 0.0028 mol OH) and triethylamine (0.31 g, 0.0031 mol) are dissolved in dichloromethane (10 ml) followed by the addition of 4-dimethylamino-benzoyl chloride (97%; 0.59 g, 0.0031 mol). The mixture is stirred for 20 hours at 25° C. and then successively washed with aqueous solutions of NaOH (1 mol/L) and brine to afford, after distilling off the solvent, a yellow resin (1.1 g).

$^1$H NMR (DMSO-d$_6$): the ratio Si/epoxide/(grafted) ketocoumarin/(grafted) 4-dimethylamino-benzoate is 1/0.27/0.56/0.49 (mol/mol/mol/mol). GPC (polystyrene calibrated; RI detector, THF), M$_n$/M$_w$/PDI (% area): 3'398/3'849/1.13 (67).

Example 50

Mixture of polyhedral oligomeric silsesquioxanes containing silicon compounds of formula (1) in which n=8, 10, 12 and A is

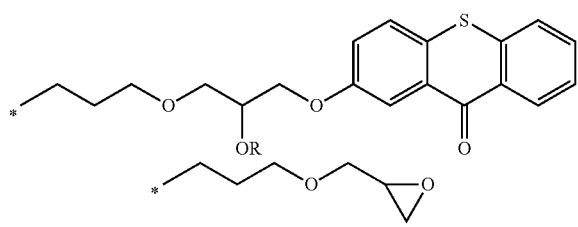

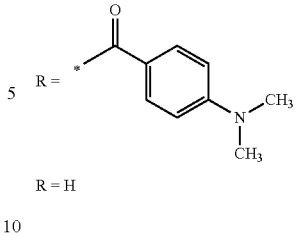

R = H obtained by ring opening addition of Glycidyl POSS EP0409 to 2-hydroxy-thioxanthen-9-one (1 eq per eq epoxide) followed by esterification with 4-dimethylamino-benzoyl chloride (1 eq).

50.a) A mixture of Glycidyl POSS EP0409 (1 g, 0.0059 mol epoxide), benzyl-trimethyl-ammonium chloride (0.06 g, 0.0003 mol), 2-hydroxy-thioxanthen-9-one (designated thioxanthone; 1.46 g, 0.0064 mol) and toluene (15 ml) is brought to 100° C. and stirred for 22 hours. The mixture is cooled down to 25° C. and concentrated on a rotary evaporator. The residue (2.65 g) is dissolved in dichloromethane (20 ml) and the solution successively washed with aqueous NaOH (1 mol/L) and brine. The organic phase is separated off and the solvent distilled off to afford an orange resin (1 g).

$^1$H NMR (DMSO-d$_6$): the ratio Si/epoxide/(grafted) thioxanthone is 1/0.19/0.73 (mol/mol/mol).

GPC (polystyrene calibrated; RI detector, THF), M$_n$/M$_w$/PDI (% area): 2'592/2'788/1.08 (72.3), 5'643/5'903/1.05 (23.2).

50.b) The resin (0.7 g. calcd. 2.9 meq OH/g, 0.002 mol OH) and triethylamine (0.22 g, 0.0022 mol) are dissolved in dichloromethane (10 ml) followed by the addition of 4-dimethylamino-benzoyl chloride (97%; 0.4 g, 0.0021 mol). The mixture is stirred for 20 hours at 25° C. and then successively washed with aqueous solutions of NaOH (1 mol/L) and brine to afford, after distilling off the solvent, an orange resin (0.65 g).

$^1$H NMR (DMSO-d$_6$): the ratio Si/(grafted) thioxanthone/(grafted) 4-dimethylamino-benzoate is 1/0.66/0.32 (mol/mol/mol).

GPC (polystyrene calibrated; RI detector, THF), M$_n$/M$_w$/PDI (% area): 2'862/3'082/1.08 (48), 6'157/6'461/1.05 (14.1).

Example 51

Mixture of polyhedral oligomeric silsesquioxanes containing silicon compounds of formula (1) in which n=8, 10, 12 and A is

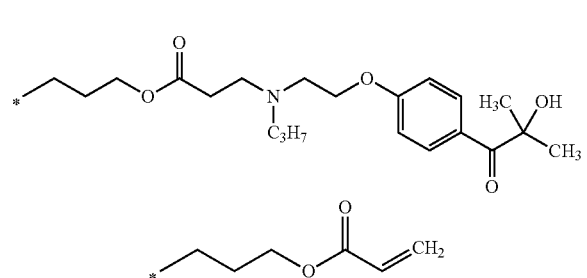

obtained by Michael addition of Acrylo POSS MA0736 to 2-hydroxy-2-methyl-1-[4-(2-propylamino-ethoxy)-phenyl]-propan-1-one (0.5 eq per eq acrylate); conditions (bismuth (III) trifluoromethanesulfonate/acetonitrile) published by. R. Varala et al., *Synlett*. 2003, 5, 720-722 adapted.

Acrylo POSS MA0736 (1 g, 0.0053 mol acrylate) and 2-hydroxy-2-methyl-1-[4-(2-propylaminoethoxy)-phenyl]-propan-1-one (designated alpha hydroxyketone; 0.78 g, 0.0029 mol) are dissolved in tetrahydrofuran (15 ml) and the solution stirred at reflux for 140 hours. Volatiles are removed using a rotary evaporator and the residue dissolved in acetonitrile (3 ml). Bismuth (III) trifluoromethanesulfonate (0.07 g, 0.0001 mol) is added and the resulting mixture stirred at 25° C. for 20 hours, the reaction being monitored by GLC. The suspension is filtered through a plug of hyflo and the filtrate concentrated using a rotary evaporator. Dichloromethane (4 ml) is added and the resulting mixture filtrated again. The filtrate is then evaporated to afford a slightly brownish resin (0.96 g).

$^1$H NMR (CDCl$_3$): the ratio Si/(grafted) alpha hydroxyketone/acrylate is 1/0.44/0.55 (mol/mol/mol).

GPC (polystyrene calibrated; RI detector, THF), $M_n/M_w$/PDI (% area): 2'617/3'019/1.15 (93.8).

Example 52

Mixture of polyhedral oligomeric silsesquioxanes containing silicon compounds of formula (1) in which n=8, 10, 12 and A is

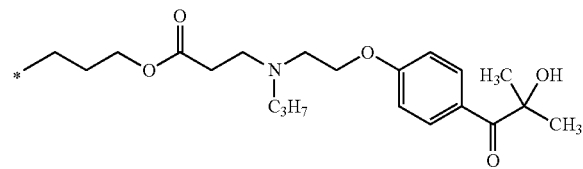

obtained by Michael addition of Acrylo POSS MA0736 to 2-hydroxy-2-methyl-1-[4-(2-propylamino-ethoxy)-phenyl]-propan-1-one (1eg per eq acrylate).

Acrylo POSS MA0736 (1 g, 0.0053 mol acrylate) and 2-hydroxy-2-methyl-1-[4-(2-propylaminoethoxy)-phenyl]-propan-1-one (designated alpha hydroxyketone; 1.4 g, 0.0053 mol) are dissolved in acetonitrile (10 ml). Bismuth (III) trifluoromethanesulfonate (0.07 g, 0.0001 mol) is added and the resulting mixture stirred at 25° C. for 44 hours, the reaction being monitored by GLC. The suspension is filtered through a plug of hyflo and the filtrate concentrated using a rotary evaporator to afford a slightly brownish resin (2 g).

$^1$H NMR (CDCl$_3$): the ratio Si/(grafted) alpha hydroxyketone/acrylate is 1/0.89/0.09 (mol/mol/mol).

GPC (polystyrene calibrated; RI detector, THF), $M_n/M_w$/PDI (% area): 3'778/4'116/1.09 (93.8).

APPLICATION EXAMPLES

Example A1

Formulation 1 is prepared by mixing the following components:

| Part in % | Trade name | Product type | Supplier |
|---|---|---|---|
| 46.0% | EBECRYL 605 | Bisphenol A epoxyacrylate diluted with 25% of tri-propylene glycol diacrylate (TPGDA) | Cytec |
| 13.2% | EBECRYL 40 | propoxylated/ethoxylated pentaerythritol tetraacrylate | Cytec |
| 39.5% | OTA 480 | propoxylated glycerol tri-acrylate | Cytec |
| 0.65% | EBECRYL 1360 | silicone hexaacrylate | Cytec |
| 0.65% | Dow Corning 57 | silicone additive | Dow Corning |

The following formulations A-E, employing formulation 1 as described above, contain 8% active photoinitiator, calculated on the amount of resin:

Formulation A:
 11.3 g of the compound of example 6
 7.2 g of Formulation 1
Formulation B:
 8.50 g of the compound of example 7
 14.75 g or Formulation 1
Formulation C:
 9.9 g of the compound of example 8
 16.2 g of Formulation 1
Formulation D:
 10.2 g of the compound of example 10
 8.3 g of Formulation 1
Formulation E:
 7.80 g of the compound of example 11
 15.46 g of Formulation 1

Samples are prepared by applying Formulations A to E onto a coilcoat by means of a bar coater. The samples are dried for 10 minutes at 60° C. to provide a dry film thickness around 6 µm and are then exposed to a medium pressure mercury lamp at 200 W/cm and 50 m/min under air. Chemical modifications resulting from acrylate crosslinking are monitored by IR spectroscopy with an ATR unit for surface measurements (Digital FTIR Excalibur Spectrometer FTS 3000 MX). The reaction of the acrylate double bonds is determined quantitatively by monitoring the disappearance of the IR band at 810 cm$^{-1}$ characteristic of the acrylate double bond.

The results are collected in table 1.

TABLE 1

| Formulation | Remaining acrylate (%) |
|---|---|
| A | 8% |
| B | 10% |
| C | 14% |
| D | 20% |
| E | 20% |

Example A2

UV-Curing of Clear Epoxy-Acrylate Coatings

A UV-curable paint is prepared using the following formulation 2:
 89.0% by weight of unsaturated epoxy-acrylate (approx. 80% in hexanediol diacrylate; EBECRYL 604, provided by Cytec Surface Specialities)
 10.0% by weight of polyethylene clycol (400) diacrylate (SR 344, provided by Sartomer)
 1.0% by weight of unsaturated silicone acrylate (EBECRYL 350, provided by Cytec Surface Specialties)
 10 g of the above formulation 2 are mixed with:
  (F) 2.2 g of the compound of example 7 and 6.8 g ethanol
  (G) 5.1 g of the compound of example 10 and 6.4 g ethanol (H) 2.3 g of the compound of example 11 and 6.8 g ethanol
(I) 2.9 g of the compound of example 12 and 5.6 g ethanol
(J) 0.3 g 2-hydroxy-1-[4-(2-hydroxyethoxy)phenyl]-2-methyl-1-propanone* and 7.5 g ethanol
(K) 0.3 g benzophenone* and 7.5 g ethanol
   * DAROCUR® BP, provided by Ciba Inc.
   ** IRGACURE® 2959, provided by Ciba Inc.

The samples contain an equivalent amount of photoinitiator by weight on formulation and an equivalent amount of ethanol.

The samples are applied onto white pre-coated aluminium panels using a wire-wound draw down bar with WFT 100 μm. The solvent is flashed off for 10 min at 60° C. and irradiated on IST laboratory UV-curing equipment using 1 Hg bulb at 100 W/cm and a line speed of 10 m/min.

The pendulum hardness (PH) according to Koenig in seconds (DIN 53157) of the cured films is measured and is shown in table 2. The higher the value, the harder the cured film.

TABLE 2

| Sample | (F) | (G) | (H) | (I) | (J) | (K) |
|---|---|---|---|---|---|---|
| PH [s] | 83 | 51 | 63 | 101 | 99 | Not cured |

Example A3

UV-Curing of Clear Epoxy-Acrylate Coatings

A coatings formulation according to example A2 is prepared. The following UV-curable samples containing the photoinitiator are prepared:
(L) 2% by weight of the compound of example 32
(M) 4% by weight of the compound of example 32

The samples are applied onto white pre-coated aluminium panels using a wire-wound draw down bar with WFT 60 μm. The sample is irradiated on IST laboratory UV-curing equipment using 2 Hg bulb at 100 W/cm and a line speed of 10 m/min.

The pendulum hardness (PH) according to Koenig in seconds (DIN 53157) of the cured films is measured and is shown in table 3. The higher the value, the harder the cured film.

TABLE 3

| Sample | (L) | (M) |
|---|---|---|
| PH [s] | 91 | 91.7 |

Example A4

UV-Curing of a Blue Flexo Ink

The following examples have been performed in a blue flexo ink with the following composition:
15.0 wt.-% hexafunctional polyester acrylate (Ebecryl 450, provided by Cytec)
20.0 wt.-% tetrafunctional polyester acrylate (Ebecryl 812, provided by Cytec)
15.0 wt.-% amine modified polyether acrylate (Ebecryl 83, provided by Cytec)
33.3 wt.-% monofunctional acrylate (Ebecryl 160, provided by Cytec)
0.7 wt.-% silicone additive (DC57, provided by Dow Corning)
16.0 wt.-% pigment (IRGALITER Blue GLO, provided by Ciba Inc.)

The photoinitiators are dissolved for each trial in a blue flexo ink with aminoacrylate during 2 h, water bath at 65° C. with magnetic stirrer 500 rpm.

The formulations to be tested are applied using a Prufbau machine onto a corona treated polymeric white foil. The samples are exposed to a medium pressure mercury lamp with a power of 200 W/cm under air at different belt speeds.

Polymerization efficiency is assessed by transfer test. Here, the printed ink is laminated after UV-exposure by a second white polymer foil and the system is submitted to a pressure of 200N. The transfer of the ink from the exposed surface to the laminating foil characterizes a poor curing of the ink surface. Reactivity is measured by the cure speed defined as the maximum belt speed required to get proper cure at a constant light intensity. The results are collected in table 4.

TABLE 4

| Cure speed of a blue flexo ink containing 5% wt PI and 1% wt IRGACURE ® 369* | |
|---|---|
| SAMPLE | Cure speed (m/min) |
| Compound of example 31 | 65 |
| Compound of example 42 | 65 |
| Compound of example 33 | 65 |
| Compound of example 19 | 65 |
| Compound of example 20 | 90 |

*IRGACURE ® 369 is 2-benzyl-2-(dimethylamino)-1-[4-(4-morpholinyl)phenyl]-1-butanone Example A5

UV-Curing of an Over Print Varnish

Following examples are performed in an overprint varnish with the following composition:
30.0 wt.-% Bisphenol A epoxyacrylate diluted with 25% of TPGDA (Ebecryl 605, provided by Cytec)
10.0 wt.-% amine modified acrylate (Ebecryl 7100, provided by Cytec)
5.0 wt.-% propoxylated/ethoxylated pentaerythritol tetraacrylate (Ebecryl 40, provided by Cytec)
30 wt.-% propoxylated glycerol triacrylate (OTA 480, provided by Cytec)
24 wt.-% tripropyleneglycol diacrylate
0.5 wt.-% silicone hexaacrylate (Ebecryl 1360, provided by Cytec)
0.5 wt.-% silicone additive (Dow Corning 57)

Formulations are applied onto an aluminum foil by means of a bar coater and dried for 10 minutes at 60° C. to provide a dry film thickness around 4 μm. Films are further exposed to a medium pressure mercury lamp at 200 W/cm under air and at 80 W/cm under nitrogen.

Polymerization efficiency is assessed by rubbing the surface with a Tela tissue. A visible damage at the surface of the film characterizes a poor curing of the ink surface.

Reactivity is measured by the cure speed defined as the maximum belt speed required to achieve proper cure at a constant light intensity. The results are collected in table 5.

TABLE 5

| SAMPLE | ATMOSPHERE | Cure speed (m/min) |
|---|---|---|
| 10% of the compound of example 32 | AIR | 40 |
| 10% of the compound of example 32 | NITROGEN | 130 |

The invention claimed is:

1. A photoinitiator compound comprising both a photoactive moiety and a tertiary amino group, bonded to a polyhedral oligomeric silsesquioxane, which is represented by formula (1) or (1')

$$[A\text{—}SiO_{1.5}]_n, \quad (1)$$

$$[(A\text{—}SiO_{1.5})_{n'}(A\text{—}R_{24}O)SiO_{1.0})_a], \quad (1')$$

wherein
n is 2m;
m is an integer of 2 to 30;
the sum of n'+ a is an integer 4-60;
n' is an even-numbered integer, except zero;
a is an even-numbered integer or uneven-numbered integer, except zero;
different A independently of each other are linear or branched $C_1$-$C_{12}$alkyl, $C_2$-$C_{20}$alkyl interrupted by one or more O, cyclopentyl, cyclohexyl, vinyl,

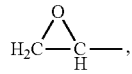

glycidyl-O-L-, $CH_2$=$C(R_5)$—(CO)O-L-,

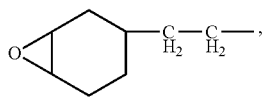

phenyl, halogen-L-, NC-L-, HS-L-, phenyl-L-, $C_5$-$C_6$cycloalkenyl-L-, $C_5$-$C_6$cycloalkyl-L-,

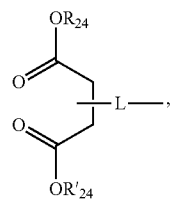

$C(R'_{24})_2$=$C(R_{24})$-L-, $R_{24}O$(CO)-L-, $OR_{24}$ or a photoactive moiety Q1, or different A independently of each other are a group of formula (2)

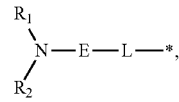

wherein the asterisk * denotes the bond to the silicon;
E is a direct bond, linear or branched $C_2$-$C_6$alkylene-O or linear or branched $C_2$-$C_6$alkylene-S which $C_2$-$C_6$alkylene-O and $C_2$-$C_6$alkylene-S are unsubstituted or substituted by one or more $OR_6$,
or E is linear or branched $C_1$-$C_6$alkylene(CO)O,
or E is

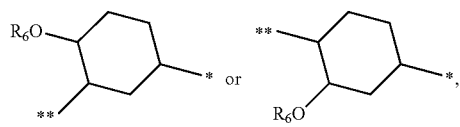

wherein the asterisk * denotes the bond to L and the double asterix ** denotes the bond to the N-atom,
or E is linear or branched $C_2$-$C_6$alkyleneN($R_3$) or linear or branched $C_2$-$C_6$alkylene(NR$_3$)$C_2$-$C_6$alkyleneN($R_4$);
L is linear or branched $C_1$-$C_4$alkylene, or is linear or branched $C_2$-$C_4$alkylene which is substituted by $OR_6$;
or L, if E is a direct bond or linear or branched $C_2$-$C_6$alkyleneN($R_3$), additionally is linear or branched $C_2$-$C_4$alkylene which is interrupted by phenylene;
or L, if E is a direct bond, additionally is phenylene;
$R_1$ and $R_2$ independently of each other are a photoactive moiety Q, hydrogen, $C_6$-$C_{14}$aryl which is unsubstituted or is substituted by one or more $R_{32}$, or $R_1$ and $R_2$ are linear or branched $C_1$-$C_6$alkyl which is unsubstituted or substituted by one or more $OR_6$, $SR_{29}$, $NR_7R_8$, (CO)$R_{24}$, (CO)O$R_{24}$ (CO)N($R_{16}$)(R'$_{16}$), CN, C($R_{24}$)=C(R'$_{24}$)$_2$ or by $C_6$-$C_{14}$aryl or by O $C_6$-$C_{14}$aryl both of which aryl are unsubstituted or substituted by $R_{32}$;
or $R_1$ and $R_2$ independently of each other are linear or branched $C_2$-$C_{26}$alkyl which is interrupted by one or more O, O(CO), (CO)O, C($R_{24}$)=C(R'$_{24}$), or $R_{16}$N(CO) and which interrupted $C_2$-$C_{26}$alkyl is unsubstituted or substituted by one or more $OR_6$, $SR_{29}$, $NR_7R_8$, (CO)$R_{24}$, (CO)O$R_{24}$, (CO)N($R_{16}$)(R'$_{16}$), C($R_{24}$)=C(R'$_{24}$)$_2$ or by CN;
or $R_1$ and $R_2$ independently of each other are $C_5$-$C_6$cycloalkyl which is unsubstituted or substituted by one or more $OR_6$ or $SR_{29}$;
or $R_1$ and $R_2$ independently of each other are (CO)$C_1$-$C_3$alkylene-$OR_{25}$,

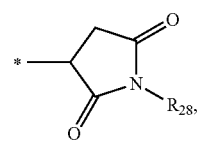

(CO)$R_{15}$, (CO)N($R_{16}$)($R_{30}$), (CO)O$R_{30}$, (PO)(O$R_{30}$)$_2$ or $R_{30}$(SO$_2$);
or $R_1$ and $R_2$ together with the nitrogen atom to which they are bonded form a group

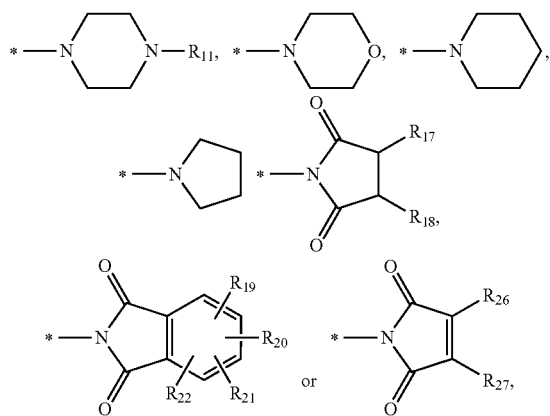

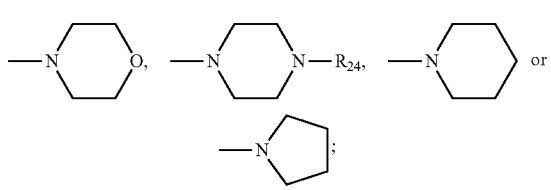

Q is a group of formula (3), (4), (5), (6), (6a) or (7)

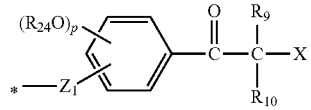     (3)

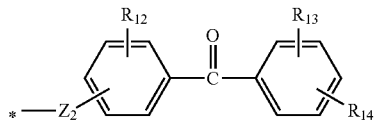     (4)

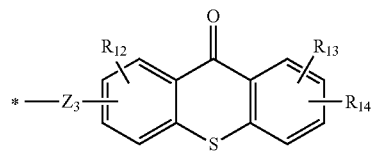     (5)

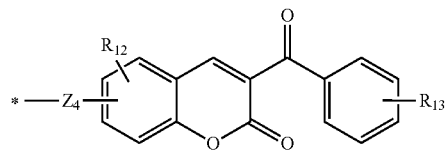     (6)

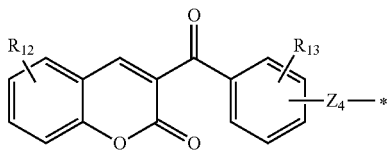     (6a)

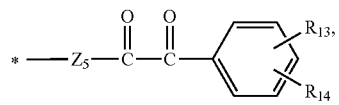     (7)

wherein the asterisk * denotes the bond to E;

$R_3$ and $R_4$ independently of each other are a photoactive moiety Q, hydrogen, $C_6$-$C_{14}$aryl which is unsubstituted or is substituted by one or more $R_{32}$, linear or branched $C_1$-$C_6$alkyl which is unsubstituted or substituted by one or more $OR_6$, $SR_{29}$, $NR_7R_8$, $(CO)R_{24}$, $(CO)OR_{24}$, $(CO)N(R_{16})(R'_{16})$, $C(R_{24})\!\!=\!\!C(R'_{24})_2$, CN or by $C_6$-$C_{14}$aryl which optionally is substituted by $R_{32}$;

or $R_3$ and $R_4$ independently of each other are linear or branched $C_2$-$C_{26}$alkyl which is interrupted by one or more O, O(CO), (CO)O, $C(R_{24})\!\!=\!\!C(R_{24})$ or $R_{16}N(CO)$ and which interrupted $C_2$-$C_{26}$alkyl is unsubstituted or substituted by one or more $OR_6$, $SR_{29}$, $NR_7R_8$, $(CO)R_{24}$, $(CO)OR_{24}$, $(CO)N(R_{16})(R'_{16})$, $C(R_{24})\!\!=\!\!C(R'_{24})_2$ or by CN;

or $R_3$ and $R_4$ independently of each other are $C_5$-$C_6$cycloalkyl which is unsubstituted or substituted by one or more $OR_6$ or $SR_{29}$;

or $R_3$ and $R_4$ independently of each other are $(CO)C_1$-$C_3$alkylene-$OR_{25}$,

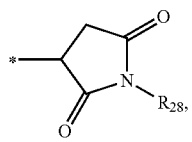

$(CO)R_{15}$, $(CO)N(R_{16})(R'_{16})$, $(CO)OR_{30}$, $(PO)(OR_{30})_2$ or $R_{30}(SO_2)$;

$R_5$ is hydrogen or linear or branched $C_1$-$C_6$alkyl;

$R_6$ is hydrogen, $C_1$-$C_8$alkyl, $Si(CH_3)_3$, $(CO)R_{15}$, $(CO)N(R_{16})(R_{30})$,

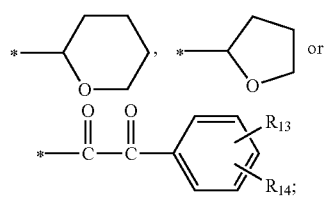

$R_7$ and $R_8$ independently of each other are linear or branched $C_1$-$C_6$alkyl or phenyl, or $R_7$ and $R_8$ together with the nitrogen atom to which they are bonded form a group in which formulae (3), (4), (5), (6), (6a) and (7) the asterisk * denotes the bonding to the nitrogen in formula (2);

Q1 is a group of formula (8), (9), (10), (11), (11a) or (12)

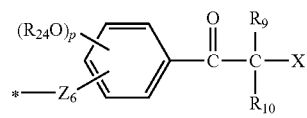     (8)

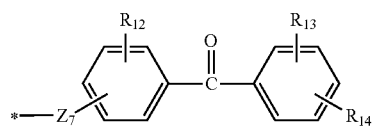     (9)

-continued

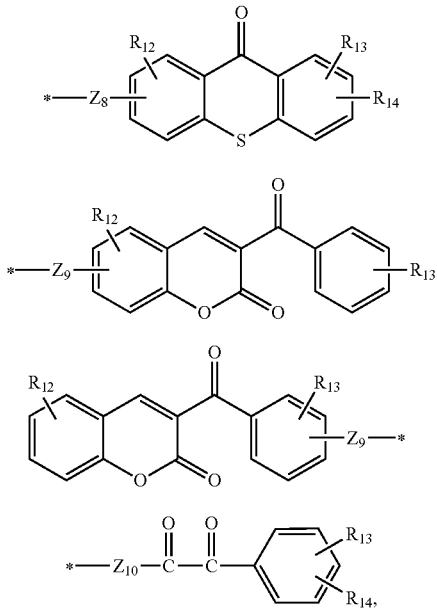

(10)

(11)

(11a)

(12)

in which formulae (8), (9) (10), (11), (11a) and (12) the asterisk * denotes the bonding to the silicon atom;

p is an integer 0, 1, 2, 3 or 4;

$Z_1$, $Z_2$, $Z_3$ and $Z_4$ independently of each other denote a direct bond, CO, $C_1$-$C_6$alkylene which is unsubstituted or substituted by one or more $OR_6$, or independently of each other are $C_2$-$C_6$alkylene which is interrupted by one or more O or O(CO) and which is unsubstituted or substituted by one or more $OR_6$, or independently of each other are $OC_1$-$C_6$alkylene which is unsubstituted or substituted by one or more $OR_6$, or independently of each other are $OC_2$-$C_{12}$alkylene which is interrupted by one or more O,(CO)O or O(CO) and which is unsubstituted or substituted by one or more $OR_6$, or independently of each other are $SC_1$-$C_{12}$alkylene which is unsubstituted or substituted by one or more $OR_6$, or independently of each other are $SC_2$-$C_{12}$alkylene which is interrupted by one or more O or O(CO), or are O—$C_1$-$C_6$alkylene-(CO) or S—$C_1$-$C_6$alkylene-(CO);

in which definitions the double asterisk ** denotes the bonding to the phenyl ring;

$Z_5$ is a direct bond, linear or branched O—$C_2$-$C_6$alkylene which is unsubstituted or substituted by one or more $OR_6$;

or is linear or branched O—$C_2$-$C_8$alkylene interrupted by one or more O and which is unsubstituted or substituted by one or more $OR_6$;

$Z_6$, $Z_7$, $Z_8$ and $Z_9$ independently of each other are linear or branched -$C_1$-$C_3$alkylene-, -O-L-,-O-E1-L-, $C_1$-$C_6$alkylene-O-L-, —O—$C_2$-$C_6$alkylene-O-L-, **—O—$C_2$-$C_6$alkylene-S-L-,
—O—$C_2$-$C_6$alkylene-S-E1-L-, -S-L-,-S-E1-L-, $C_1$-$C_6$alkylene-S-L-, $C_1$-$C_6$alkylene-S-E1-L-, —S—$C_2$-$C_6$alkylene-S-L-, —S—$C_2$-$C_6$alkylene-S-E1-L-, —S—$C_2$-$C_6$alkylene-O-L-, —(CO)—O-L-, —(CO)—O-E2-L-*, $C_1$-$C_6$alkylene-(CO)—O-L-, $C_1$-$C_6$alkylene-(CO)—O-E2-L-, O—$C_1$-$C_6$alkylene-(CO)—O-L-, O—$C_1$-$C_6$alkylene-(CO)—O-E2-L-, S—$C_1$-$C_6$alkylene-(CO)—O-L- or S—$C_1$-$C_6$alkylene-(CO)—O-E2-L-, in which definitions the double asterisk ** denotes the bonding to the phenyl ring;

$Z_{10}$ is -O-L- or —O-E2-L-, in which definitions the double asterisk ** denotes the bonding to the phenyl ring;

E1 is

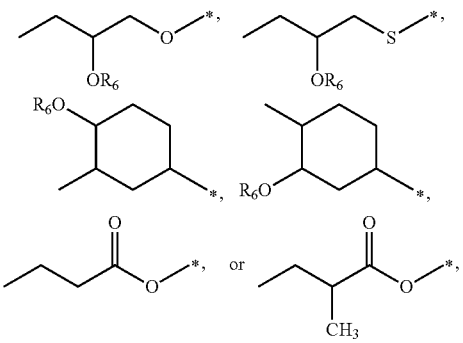

in which definitions the asterisk * denotes the bonding to L;

E2 is

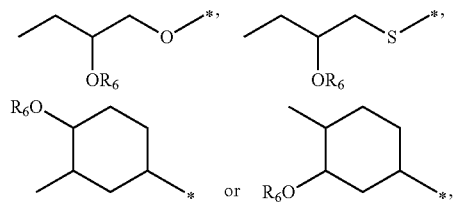

in which definitions the asterisk * denotes the bonding to L;

X is $OR_5$ or $NR_7R_8$;

$R_9$ and $R_{10}$ independently of each other are $C_1$-$C_6$alkyl, $C_2$-$C_{12}$alkenyl or phenyl$C_1$-$C_3$alkyl which is unsubstituted or substituted by one or more $C_1$-$C_6$alkyl;

$R_{11}$ has one of the definitions given for $R_1$ and $R_2$;

$R_{12}$, $R_{13}$ and $R_{14}$ independently of each other are hydrogen, linear or branched $C_1$-$C_{12}$alkyl which is unsubstituted or substituted by one or more OH, $C_1$-$C_4$alkoxy, phenyl, halogen or by CN; or $R_{12}$, $R_{13}$ and $R_{14}$ independently of each other are $C_2$-$C_{12}$alkyl which is interrupted by one or more non-consecutive O; or $R_{12}$, $R_{13}$ and $R_{14}$ are halogen, OH, $NR_7R_8$, (CO)$R_{23}$, $C_1$-$C_{12}$alkoxy, $C_1$-$C_{12}$alkylthio, -($C_1$-$C_6$alkyl)-$NR_7R_8$ or —O—($C_1$-$C_6$alkyl)$NR_7R_8$;

$R_{15}$ is hydrogen, linear or branched $C_1$-$C_{20}$alkyl which unsubstituted or substituted by C($R_{24}$)=C($R_{24}$)$_2$ or N($R_7$)($R_8$), or is $C_2$-$C_{20}$alkyl which is interrupted by one or more O or C($R_{24}$)=C($R_{24}$); or is phenyl which is unsubstituted or is substituted by one or more $C_1$-$C_4$alkyl, halogen, $C_1$-$C_4$alkoxy, N($R_7$)($R_8$) or $C_1$-$C_4$alkylthio, or $R_{15}$ is $C_5$-$C_6$-cycloalkyl,

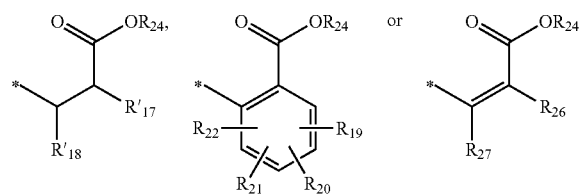

wherein the asterisk * represents the bond to the C-atom of the carbonyl group of $(CO)R_{15}$;

$R_{16}$ and $R'_{16}$ independently of one another are hydrogen, phenyl or linear or branched $C_1$-$C_6$alkyl;

$R_{17}$, $R'_{17}$, $R_{18}$ and $R'_{18}$ independently of one another are hydrogen, linear or branched $C_1$-$C_{20}$alkyl which is unsubstituted or substituted by one or more $C(R_{24})$=C$(R_{24})_2$, or is linear or branched $C_2$-$C_{20}$alkyl which is interrupted by $C(R_{24})$=C$(R_{24})$;

or $R_{17}$ and $R_{18}$ together with the C-atoms to which they are bonded form

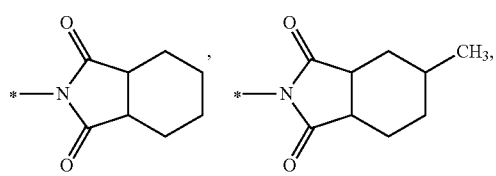
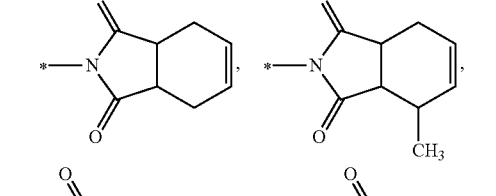
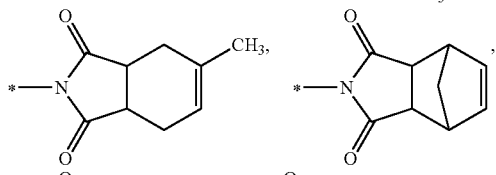
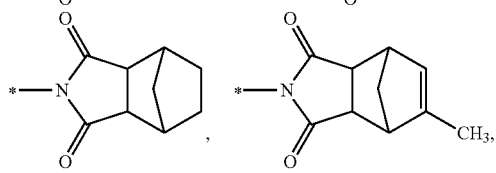
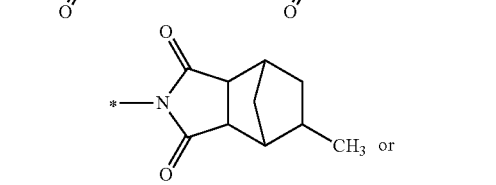
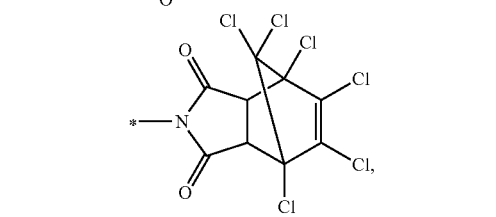

wherein the asterisk * denotes the bond to E, or $R'_{17}$ and $R'_{18}$ together with the C-atoms to which they are bonded form

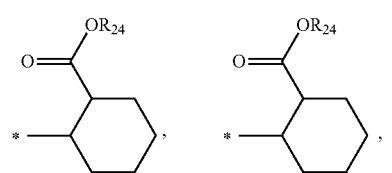
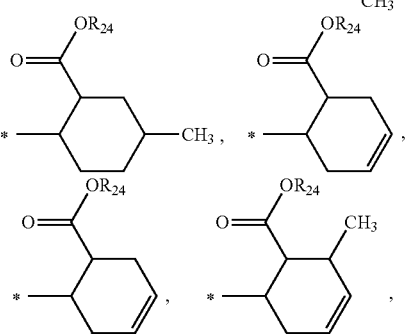
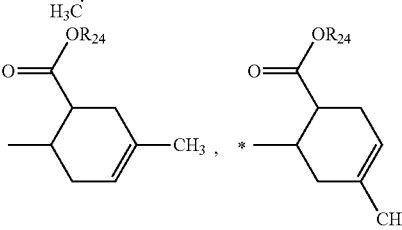
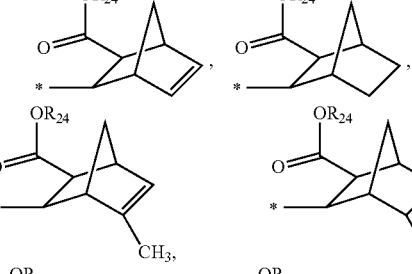
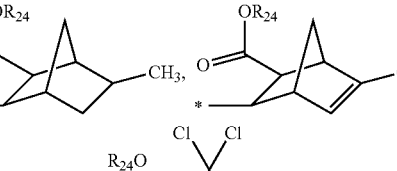
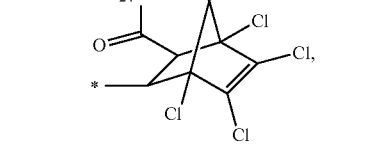
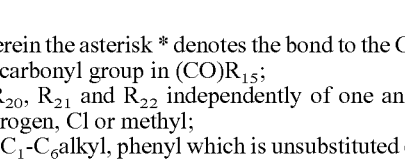
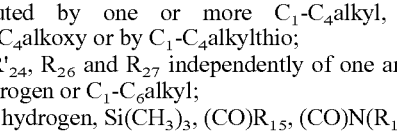

wherein the asterisk * denotes the bond to the C-atom of the carbonyl group in $(CO)R_{15}$;

$R_{19}$, $R_{20}$, $R_{21}$ and $R_{22}$ independently of one another are hydrogen, Cl or methyl;

$R_{23}$ is $C_1$-$C_6$alkyl, phenyl which is unsubstituted or is substituted by one or more $C_1$-$C_4$alkyl, halogen, $C_1$-$C_4$alkoxy or by $C_1$-$C_4$alkylthio;

$R_{24}$, $R'_{24}$, $R_{26}$ and $R_{27}$ independently of one another are hydrogen or $C_1$-$C_6$alkyl;

$R_{25}$ is hydrogen, $Si(CH_3)_3$, $(CO)R_{15}$, $(CO)N(R_{16})(R_{30})$,

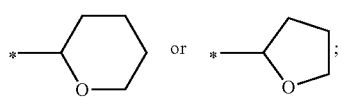

$R_{28}$ is hydrogen, linear or branched $C_1$-$C_6$alkyl which is unsubstituted or is substituted by phenyl; or is $C_5$-$C_6$cycloalkyl or phenyl which is unsubstituted or substituted by one or more $C_1$-$C_4$alkyl or by halogen;

$R_{29}$ is hydrogen, linear or branched $C_1$-$C_6$alkyl which is unsubstituted or substituted by one or more OH, $NR_7R_8$, $(CO)R_{24}$, $(CO)OR_{24}$, $(CO)N(R_{16}(R'_{16})$ or by CN, or $R_{29}$ is linear or branched $C_2$-$C_{20}$alkyl which is interrupted by one or more O, O(CO) or $N(R_{16})(CO)$ and which interrupted $C_2$-$C_{20}$alkyl is unsubstituted or is substituted by one or more OH, $NR_7R_8$, $(CO)R_{24}$, $(CO)OR_{24}$ or by $(CO)N(R_{16}(R'_{16})$, or $R_{29}$ is

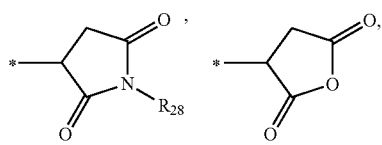

$Si(CH_3)_3$,
$(CO)R_{31}$, $(CO)N(R_{16})(R_{30})$,

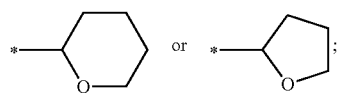

$R_{30}$ phenyl or linear or branched $C_1$-$C_6$alkyl;

$R_{31}$ is hydrogen, linear or branched $C_1$-$C_{20}$alkyl which unsubstituted or substituted by $C(R_{24})=C(R_{24})_2$, or is $C_2$-$C_{20}$alkyl which is interrupted by one or more O or $C(R_{24})=C(R_{24})$; or is phenyl which is unsubstituted or is substituted by one or more $C_1$-$C_4$alkyl, halogen, $C_1$-$C_4$alkoxy or by $C_1$-$C_4$alkylthio, or $R_{31}$ is $C_5$-$C_6$-cycloalkyl,

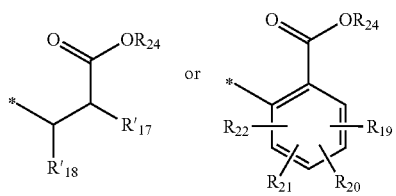

wherein the asterisk * represents the bond to the C-atom of the carbonyl group of $(CO)R_{31}$; and $R_{32}$ is halogen, CN, OH, $C_1$-$C_4$alkoxy, $(CO)OR_{24}$, $NR_7R_8$, vinyl or $C_1$-$C_6$alkyl which is unsubstituted or is substituted by one or more CN, OH, $(CO)R_{24}$ or by $NR_8R_9$;

provided that at least one Q and at least one amine functionality via a group of the formula (2) are present in the photoinitiator compound.

2. A photoinitiator compound according to claim 1, of the formula (1), wherein n is 2m;
m is an integer of 3 to 6;
different A independently of each other are linear or branched $C_1$-$C_{12}$alkyl, glycidyl-O-L-, $CH_2=C(R_5)$—(CO)O-L-, or a photoactive moiety Q1,
or different A independently of each other are a group of formula (2)

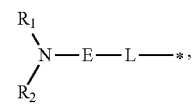

wherein the asterisk * denotes the bond to the silicon;

E is a direct bond, linear or branched $C_2$-$C_6$alkylene-O which is unsubstituted or substituted by one or more $OR_6$, or E is linear or branched $C_1$-$C_6$alkylene(CO)O, or E is linear or branched $C_2$-$C_6$alkyleneN($R_3$) or linear or branched $C_2$-$C_6$alkylene($NR_3$)$C_2$-$C_6$alkyleneN($R_4$);

L is linear or branched $C_1$-$C_4$alkylene;

$R_1$ and $R_2$ independently of each other are a photoactive moiety Q, hydrogen, or $R_1$ and $R_2$ are linear or branched $C_1$-$C_6$alkyl which is unsubstituted or substituted by one or more $OR_6$, $NR_7R_8$ or by $(CO)OR_{24}$;

or $R_1$ and $R_2$ independently of each other are linear or branched $C_2$-$C_{26}$alkyl which is interrupted by one or more O or (CO)O and which interrupted $C_2$-$C_{26}$alkyl is unsubstituted or substituted by one or more $OR_6$, $NR_7R_8$ or by $C(R_{24})=C(R'_{24})_2$;

or $R_1$ and $R_2$ independently of each other are $(CO)R_{15}$;

$R_3$ and $R_4$ independently of each other are a photoactive moiety Q, hydrogen, linear or branched $C_1$-$C_6$alkyl which is unsubstituted or substituted by one or more $OR_6$;

or $R_3$ and $R_4$ independently of each other are linear or branched $C_2$-$C_{26}$alkyl which is interrupted by one or more O, and which interrupted $C_2$-$C_{26}$alkyl is unsubstituted or substituted by one or more $OR_6$;

$R_5$ is hydrogen;

$R_6$ is hydrogen, $C_1$-$C_4$alkyl or $(CO)R_{15}$;

$R_7$ and $R_8$ independently of each other are linear or branched $C_1$-$C_6$alkyl, or $R_7$ and $R_8$ together with the nitrogen atom to which they are bonded form a group

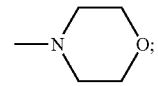

Q is a group of formula (3), (4) or (7);
Q1 is a group of formula (9), (10) or (11);
p is 0;
$Z_1$ and $Z_2$ independently of each other are **$OC_1$-$C_6$alkylene which is unsubstituted or substituted by one or more $OR_6$,
or independently of each other are **$OC_2$-$C_{12}$alkylene which is interrupted by one or more O or O(CO) and which is unsubstituted or substituted by one or more $OR_6$;
$Z_5$ is linear or branched O-$C_2$-$C_8$alkylene interrupted by one or more O;
$Z_7$, $Z_8$ and $Z_9$ independently of each other are **—O-E1-L-;

E1 is

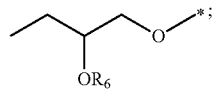

X is $OR_5$;

$R_9$ and $R_{10}$ independently of each other are $C_1$-$C_6$alkyl;

$R_{12}$, $R_{13}$ and $R_{14}$ independently of each other are hydrogen or halogen;

$R_{15}$ is linear or branched $C_1$-$C_{20}$alkyl or is phenyl which is unsubstituted or is substituted by one or more $N(R_7)(R_8)$; and $R_{24}$ and $R'_{24}$ are hydrogen.

3. A mixture of photoinitiator compounds of the formula (1) or (1') as defined in claim 1.

4. A mixture of photoinitiator compounds according to claim 3 wherein the compounds of the formula (1') are selected from the group consisting of compounds of formula (W1), (W2), (W3) and (W4), wherein
(W1) the sum of n' and a is an integer 6, 8, 10 or 12;
n' is an integer 4, 6, 8 or 10; and
a is 2;
(W2) the sum of n' and a is an integer 6, 8, 10 or 12;
n' is an integer 2, 4, 6 or 8; and
a is 4;
(W3) the sum of n' and a is an integer 7, 9 or 11;
n' is an integer 6, 8 or 10; and
a is 1;
(W4) the sum of n' and a is an integer 7, 9 or 11;
n' is an integer 4, 6 or 8; and
a is 3.

5. A mixture according to claim 1, wherein (i) compounds of the formula (1) are present wherein n is 6 and (ii) compounds of the formula (1) are present wherein n is 8 and (iii) compounds of the formula (1) are present wherein n is 10 and (iv) compounds of the formula (1) are present wherein n is 12.

6. A photopolymerizable composition comprising (A) at least one ethylenically unsaturated photopolymerizable compound and (B) at least one photoinitiator or photoinitiator mixtuer according to claim 1.

7. A photopolymerizable composition according to claim 6, which additionally to the component (B) comprises at least one further photoinitiator (C), and/or further coinitiators (D) and/or other additives.

8. A polymerizable composition according to claim 6, which comprises 0.05 to 15% by weight, of the photoinitiator or photoinitiator mixture compound based on the total composition.

9. A process for the photopolymerization of monomeric, oligomeric or polymeric compounds containing at least one ethylenically unsaturated double bond, which comprises adding to the abovementioned compounds at least one photoinitiator or photoinitiator mixture according to claim 1 and irradiating the resulting composition with electromagnetic radiation.

10. A method of using a photoinitiator or photoinitiator mixture as defined in claim 1, the method comprising: photopolymerizing monomeric, oligomeric or polymeric compounds containing at least one ethylenically unsaturated double bond.

11. A process according to claim 9 for the preparation of pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

12. A coated substrate coated on at least one surface with a composition according to claim 6.

13. A polymerized or crosslinked composition obtained by curing a polymerizable composition according to claim 6.

* * * * *